(12) United States Patent
Conrad

(10) Patent No.: US 9,907,833 B2
(45) Date of Patent: *Mar. 6, 2018

(54) USE OF RELAXIN TO TREAT PLACENTAL SYNDROMES

(71) Applicant: UNIVERSITY OF FLORIDA RESEARCH FOUNDATION, INC., Gainesville, FL (US)

(72) Inventor: Kirk P. Conrad, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 82 days.

This patent is subject to a terminal disclaimer.

(21) Appl. No.: 14/340,858

(22) Filed: Jul. 25, 2014

(65) Prior Publication Data

US 2015/0031616 A1    Jan. 29, 2015

Related U.S. Application Data

(60) Provisional application No. 61/858,282, filed on Jul. 25, 2013.

(51) Int. Cl.
*A61K 38/22* (2006.01)
*C12Q 1/68* (2006.01)
*G01N 33/68* (2006.01)

(52) U.S. Cl.
CPC ........ *A61K 38/2221* (2013.01); *C12Q 1/6876* (2013.01); *G01N 33/6893* (2013.01); *C12Q 2600/106* (2013.01); *C12Q 2600/158* (2013.01); *C12Q 2600/16* (2013.01); *G01N 2800/368* (2013.01)

(58) Field of Classification Search
None
See application file for complete search history.

(56) References Cited

U.S. PATENT DOCUMENTS

| | | |
|---|---|---|
| 3,991,174 A | 11/1976 | Grundman |
| 4,208,187 A | 6/1980 | Givner |
| 4,981,785 A | 1/1991 | Nayak et al. |
| 5,166,191 A | 11/1992 | Cronin et al. |
| 5,358,691 A | 10/1994 | Clark et al. |
| 5,599,677 A | 2/1997 | Dowell et al. |
| 5,672,480 A | 9/1997 | Dowell et al. |
| 5,759,807 A | 6/1998 | Breece et al. |
| 5,811,395 A | 9/1998 | Schwabe et al. |
| 5,885,530 A | 3/1999 | Babson et al. |
| 6,159,750 A | 12/2000 | Edmonds |
| 6,234,974 B1 | 5/2001 | Catt et al. |
| 6,451,619 B1 | 9/2002 | Catt et al. |
| 7,044,919 B1* | 5/2006 | Catt .................. A61B 10/0012 436/65 |
| 8,026,215 B2 | 9/2011 | Unemori |
| 2006/0247163 A1* | 11/2006 | Unemori ............ A61K 38/2221 514/5.3 |
| 2011/0171650 A1 | 7/2011 | Conrad et al. |
| 2011/0281801 A1 | 11/2011 | Stewart et al. |

FOREIGN PATENT DOCUMENTS

| | | | |
|---|---|---|---|
| WO | WO 2005/115435 A2 | 12/2005 | |
| WO | WO 2009/007848 A2 | 1/2009 | |
| WO | WO2010/033553 | * 3/2010 | ............... C21Q 1/68 |

OTHER PUBLICATIONS

Liu et al., Nucleic Acids Research, 2003; 31: 82-86.*
Found, Seminars in Nephrology, 2011; 31: 15-32.*
PCT/US2009/044251, Nov. 19, 2009, Corthera, Inc.
Aryee, Martin J et al. "An improved empirical bayes approach to estimating differential gene expression in microarray time-course data: BETR (Bayesian Estimation of Temporal Regulation)," *BMC Bioinformatics*, 2009, 10:409.
Büllesbach, Erika E. et al, "Total Synthesis of Human Relaxin and Human Relaxin Derivatives by Solid-phase Peptide Synthesis and Site-directed Chain Combination," *Journal of Biological Chemistry*, 1991, 266(17):10754-10761.
Burney, Richard et al. "Gene Expression Analysis of Endometrium Reveals Progesterone Resistance and Candidate Susceptibility Genes in Women with Endometriosis," *Endocrinology*, 2007, 148(8):3814-3826.
Conrad, Kirk P., "Unveiling the Vasodilatory Actions and Mechanisms of Relaxin," *Journal of the American Heart Association*, 2010, 56(1):2-9.
Duncan, W. Colin et al. "Ectopic Pregnancy as a Model to Identify Endometrial Genes and Signaling Pathways Important in Decidualization and Regulated by Local Trophoblast," *PLoS ONE*, 2011, 6(8):e23595.
Elder, Murdoch et al., "Is Pre-eclampsia Preventable?" *Annals of Medicine*, 1991, 23(6):Abstract.
Founds, S.A et al., "Altered Global Gene Expression in First Trimester Placentas of Women Destined to develop Preeclampsia," *Placenta*, 2009, 30:15-24.
Giudice Linda. Application of functional genomics to primate endometrium: insights into biological processes. *Reproductive Biology and Endocrinology*, 2006, 4:1-12.
Giudice, Linda et al., "Steroid and peptide regulation of insulin-like growth factor-binding proteins secreted by human endometrial stromal cells is dependent on stromal differentiation," *Journal of Clinical Endocrinology and metabolism*, 1992, 75(5):1235-1241.
Hess, A.P. et al. "Decidual Stromal Cell Response to Paracrine Signals from the Trophoblast: Amplification of Immune and Angiogenic Modulators," *Biology of Reproduction*, 2007, 76:102-117.
Hornik, et al., "Open-source machine learning: R meets Weka," *Computational Statistics*, 2009, 24:225-232.

(Continued)

*Primary Examiner* — Christina M Borgeest

(74) *Attorney, Agent, or Firm* — Saliwanchik, Lloyd & Eisenschenk

(57) ABSTRACT

The subject application relates to methods for treating a placental syndrome, wherein relaxin is administered during the late secretory/luteal (LS) phase of the menstrual cycle in women who have a propensity for developing the placental syndrome. In certain embodiments, administration of relaxin continues beyond the LS phase and into pregnancy.

23 Claims, 22 Drawing Sheets

(56) References Cited

OTHER PUBLICATIONS

Irwin, Juan et al., "Hormonal regulation of human endometrial stromal cells in culture: an in vitro model for decidualization," *Fertility and Sterility*, 1989, 52(5):761-768.

Koopman, Louise, "Human Decidual Natural Killer Cells Are a Unique NK Cell Subset with Immunomodulatory Potential," *The Journal of Experimental Medicine*, 2003, 198(8):1201-1212.

Kopcow, A.D et al., "Human Decidual NK Cells from Gravid Uteri and NK Cells from Cycling Endometrium are Distinct NK cell Subsets," *Placenta*, 2010, 31:334-338.

Langfelder, Peter. et al. "WGCNA: an R package for weighted correlation network analysis," *BMC Bioinformatics*, 2008, 9:559.

Popovici, Roxana et al., "Discovery of New Inducible Genes in In Vitro Decidualized Human Endometrial Stromal Cells Using Microarray Technology," *Endocrinology*, 2000, 141(9):3510-3513.

Rabaglino, M.B et al., "A Systems Biology Approach Reveals Evidence for Defective Endometrial Maturation in Women Destined to Develop Preeclampsia," 2014, is Manuscript.

Savaris, Ricardo et al., "Endometrial Gene Expression in Early Pregnancy: Lessons From Human Ectopic Pregnancy," *Reproductive Sciences*, 2008, 15(8):797-816.

Smyth, Gordon., "Linear Models and Empirical Bayes Methods for Assessing Differential Expression in Microarray Experiments," *Statistical Applications in Genetics and Molecular Biology*, 2004, 3(1):1-27.

Talbi, S et al., "Molecular Phenotyping of Human Endometrium Distinguishes Menstrual Cycle Phases and Underlying Biological Processes in Normo-Ovulatory Women," *Endocrinology*, 2006, 147(3):1097-1121.

Tseng, Linda et al., "Progesterone Receptor (hPR) Upregulates the Fibronectin Promoter Activity in Human Decidual Fibroblasts," *DNA and Cell Biology*, 2003, 22(10):633-640.

Xiao, J et al., "Identification and optimization of small-molecule agonists of the human hormone receptor RXFP1," *National Communications*, 2013, 4:Abstract.

Zhang, et al., "A General Framework for Weighted Gene Co-Expression Network Analysis," *Statistical Applications in Genetics and Molecular Biology*,2005, 4(17).

* cited by examiner

FIGURE 2

Spontaneously Conceived Pregnancies

- 160 surplus CVS specimens (~11.5 weeks)
- N=4 developed preeclampsia* matched with N=8 with normal pregnancy outcome
- Affymetrix GeneChips
- 168 dysregulated genes by J5 or fold-change analysis

*Preeclampsia definition is based on the National High Blood Pressure Education Program Working Group

FIGURE 3

- Investigation of 26 proven hypoxia regulated genes (oxygen supply, cellular metabolism, growth and apoptosis, other) revealed no differences between CVS from normal and PE pregnancies.
- Investigation of 12 oxidative stress genes revealed no differences between CVS from normal and PE pregnancies.

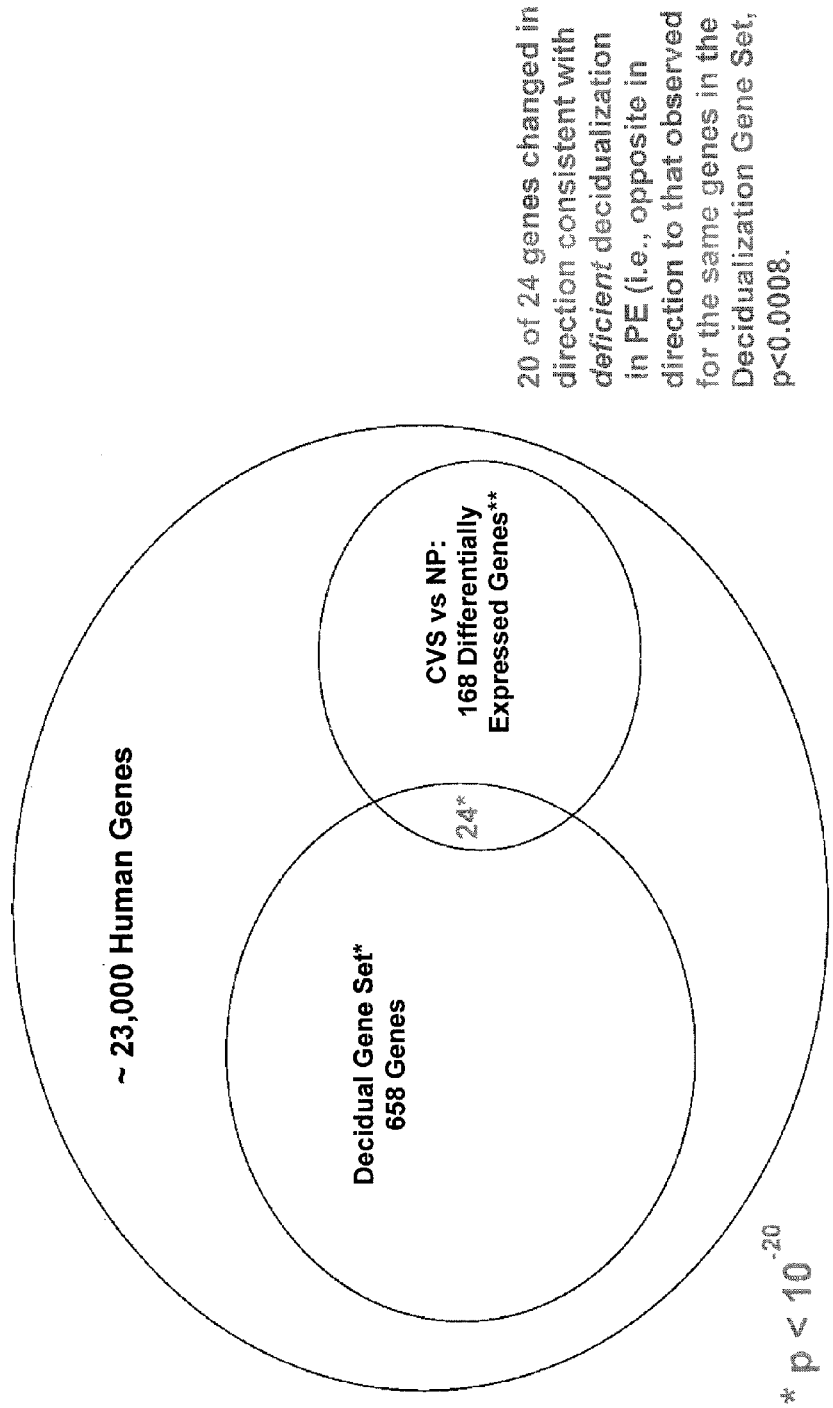

FIGURE 5

Spontaneously Conceived Pregnancies

*"Decidualopathy" may be etiological in the development of preeclampsia*

- An additional 21 of the 168 dysregulated genes in the CVS study (not represented in the "Decidual Gene Set" of Duncan et al.) were previously identified in the literature to be associated with (pre)decidualization bringing the total number to 45 genes.

- e.g., PRL -7.65, IGFBP-1 -10.35, Glycodelin -15.64.

- 38 of these 45 genes changed in direction opposite to that observed for the biological process of decidualization ($p<0.00001$).

- Ingenuity Pathway Analysis further revealed "Lack of NK Cells" ($p=0.00092$) and deficient "Activation of NK Cells" ($p=0.00096$).

Prospective Study
Endometrial Antecedents of Preeclampsia

USE OF RELAXIN TO TREAT PLACENTAL SYNDROMES

CROSS-REFERENCE TO A RELATED APPLICATION

This application claims the benefit of U.S. provisional application Ser. No. 61/858,282 filed Jul. 25, 2013, which is incorporated herein by reference in its entirety.

The subject invention was made with government support under Grant Nos. RO1 HD030325; RO1 HL067937; RO1 DK063321; PO1 HD030367; and PO1 HD065647 research projects supported by the National Institute of Health (NIH). The government has certain rights in the invention.

BACKGROUND OF INVENTION

Preeclampsia (also known as toxemia and referred to herein as PE) is a dangerous and volatile hypertensive disease that affects pregnant women, usually late in the second or third trimester, and postnatal women in the first six weeks after delivery. It is a leading cause of maternal, fetal and neonatal, morbidity and mortality. Further, both women and their children who survive PE are at greater risk for future adverse cardiovascular events.

The condition affects the kidneys, liver, brain, heart and placenta of the pregnant woman. PE occurs in approximately three to five percent of pregnancies and is only alleviated by ending the pregnancy, either by induction of labor or cesarean. PE most commonly occurs during a first pregnancy. The risk for preeclampsia is also known to be moderately increased for certain groups of pregnant women, including women who are over 35 years of age or under 18 years of age; women who are genetically predisposed to this condition; women who suffer from preexisting hypertension, diabetes, autoimmune diseases like lupus, various inherited thrombophilias like Factor V Leiden, or renal disease; obese women, and in women with multiple gestations (twins, triplets, and more). The single most significant risk for developing preeclampsia is having had preeclampsia in a previous pregnancy.

PE can develop either gradually or suddenly, and may remain mild throughout the pregnancy or become severe. PE is diagnosed by new onset protein in the urine (proteinuria) and high blood pressure. Common symptoms in addition to high blood pressure and proteinuria are elevated uric acid, vision problems such as blinking lights or blurry vision, persistent headaches, extreme swelling of hands and feet, fluid retention, pain in the upper right abdomen. If untreated, preeclampsia can damage the mother's liver or kidneys, cause pulmonary edema, deprive the fetus of oxygen, and cause eclampsia (seizures). A pregnant woman with signs of preeclampsia must be closely monitored by a physician. Moderate to severe preeclampsia is often treated in the hospital with bed rest, magnesium sulfate, and medication for high blood pressure. Unfortunately, delivery is still the only true "cure" for preeclampsia. In fact, when a woman has severe preeclampsia or is near term with mild to moderate preeclampsia, delivery is still the best remedy to date. Labor is then started with medication, unless a cesarean section is deemed necessary. Within the first few days following delivery, the mother's blood pressure usually returns to normal; however, with severe preeclampsia, it may take several weeks for blood pressure to return to normal.

The pathogenesis of PE has been investigated in the last decade, e.g., circulating factors emanating from the placenta have been identified in the blood that injure the endothelium, thereby producing maternal symptoms including hypertension and proteinuria. In contrast, PE etiology remains uncertain and infrequently addressed. One reason why so little is known about what causes PE is that the disease likely begins in early pregnancy, secondary in large measure to "shallow" placentation, i.e., deficient trophoblast (Tr) invasion of uterine spiral arteries, which starts in the 1st trimester. Normally, placental cells called Tr invade the endometrium, inner ⅓ of the myometrium and the uterine spiral arteries, ultimately remodeling the latter, which allows for large increases of blood flow, oxygen and nutrients to the developing placenta and fetus. In PE, Tr invasion is impaired and hence blood flow and oxygen delivery to the placenta and fetus is compromised, leading to release of factors from the placenta that circulate and injure the maternal endothelium, thereby producing disease manifestations. Thus, the Tr ("seed") has been the focus of much investigative attention. In contrast, the uterine milieu ("soil") has been less explored.

Endometrial maturation is a necessary precursor for healthy placentation. Stromal cells, uterine and glandular epithelial cells, as well as spiral arteries undergo distinct morphologic and functional changes, which begin before pregnancy in the late secretory/luteal (LS) phase of the menstrual cycle ("pre-decidualization") continuing after conception ("decidualization"). Unfortunately, little data is available regarding whether certain elements in the LS endometrium (i.e., before conception) play a role in the later development of PE during pregnancy.

Because of the current lack of effective treatments for placental syndromes (i.e., PE and IUGR), there is a strong need to develop new therapeutic approaches for protecting both mother and child from the harmful effects of placental syndromes.

BRIEF SUMMARY

The present invention provides methods for treatment, diagnosis and/or prevention of placental syndromes including, but not limited to, PE, deficient Tr invasion of uterine spiral arteries, defective decidualization, compromised endometrial maturation (e.g., pre-decidualization) in the LS phase of the menstrual cycle and inadequate placentation. Advantageously, the present invention facilitates treating woman in a timely fashion to decrease the risk for developing placental syndromes, such as PE, following conception.

In one embodiment, the invention provides a method for treating and/or reducing the likelihood of development of a placental syndrome comprising the steps of: (a) determining whether a woman has experienced a placental syndrome during a previous pregnancy; (b) if the woman has experienced a placental syndrome during a previous pregnancy, determining the late secretory/luteal (LS) phase of the menstrual cycle; and (c) administering a therapeutically effective amount of relaxin to the woman during the LS phase of menstruation to treat and/or reduce the likelihood of development of the placental syndrome. Preferably, the placental syndrome is PE and/or IUGR.

In a related embodiment, the method further comprises administering relaxin from the LS phase of the menstrual cycle throughout a portion or entirety of the first trimester of pregnancy. In another embodiment, the method further comprises administering relaxin from the LS phase of the menstrual cycle throughout a portion or entirety of the second trimester of pregnancy. In yet another embodiment, the method further comprises administering relaxin from the LS phase of the menstrual cycle throughout a portion or entirety of the third trimester of pregnancy. In another embodiment, the method further comprises administering relaxin from the LS phase of the menstrual cycle throughout pregnancy and following delivery.

In another embodiment, the invention provides methods comprising the steps of: (a) determining whether the woman is at risk for developing a placental syndrome; (b) if the woman is at risk, determining the late secretory/luteal (LS) phase of the menstrual cycle; and (c) administering natural or exogenous relaxin to the woman during the LS phase of menstruation. In a related embodiment, step (a) comprises obtaining a biological sample from the woman (such as blood, urine, uterine tissue (e.g., endometrial biopsy) or secretions) and measuring in the sample biomarker(s) that reflect endometrial maturation (pre-decidualization) or a deficiency thereof.

In certain related embodiments, the step of determining whether the woman is at risk for developing a placental syndrome comprises diagnosing whether the woman has a genetic predisposition or propensity for impaired relaxin production and/or activity. For example, this determination may comprise determining the nucleotide sequence of at least a portion of a gene that is involved with deficient decidualization in PE.

The subject invention is directed to addressing PE disease etiology that starts in the first trimester with antecedents before conception. In certain embodiments, the method of the subject invention can be used to (1) correct deficient endometrial maturation ("(pre)decidualization"), thereby improving histiotrophic nutrition of the placenta and fetus before 10 weeks; (2) promote trophoblast invasion and physiological remodeling of uterine spiral arteries, and hence, fetoplacental blood flow after 10 weeks; and (3) directly stimulate survival and invasion of trophoblast, and thus, improve placentation and placental function; and augment maternal circulatory adaptations to pregnancy, which are deficient in women destined to develop severe preeclampsia or intrauterine growth restriction, particularly in the first trimester. The treatments described herein promote proper endometrial maturation prior to conception, which is beneficial in obviating PE development, as well as intrauterine growth restriction (IUGR) during pregnancy Relaxin employed by the subject invention can be, for example, synthetic or recombinant relaxin, or a pharmaceutically effective relaxin agonist or mimetic. In one embodiment of the invention, relaxin is H1 human relaxin. In another embodiment, relaxin is H2 human relaxin. In yet another embodiment, relaxin is H3 human relaxin. In a further embodiment, relaxin is synthetic or recombinant human relaxin, or a pharmaceutically effective relaxin agonist or relaxin mimetic. Thus, a non-pregnant female at risk for preeclampsia can be treated with a pharmaceutical formulation of isolated, synthetic or recombinant human relaxin or relaxin agonist or mimetic during the LS phase of menstruation and potentially throughout pregnancy (vide supra).

In one embodiment, a human female is treated with synthetic human relaxin at least during the LS phase of menstruation, preferably through the end of the first trimester. In another embodiment, a human female is treated with recombinant human relaxin at least during the LS phase of menstruation, preferably through the end of the first trimester. In yet another embodiment, a human female is treated with a pharmaceutically effective relaxin agonist or mimetic during the LS phase of menstruation, preferably through the end of the first trimester. Relaxin or mimetics can be administered to the female through a number of different routes, including but not limited to, subcutaneously, intramuscularly, intravenously, sublingually, intranasally, orally, topically (e.g., by dermal patch) or via inhalation. One preferred route of administration is subcutaneous (SQ) administration

BRIEF DESCRIPTION OF DRAWINGS

FIG. 2 is a slide highlighting the analysis of genes isolated from CVS tissues in spontaneously conceived pregnancies to determine dysregulated genes associated with PE.

FIG. 3 is a slide regarding the analysis of the dysregulated genes to determine whether hypoxia or oxidative stress regulated genes were upregulated.

FIG. 4 is a venn diagram highlighting the twenty-four (24) genes associated with both deficient decidualization and PE.

FIG. 5 is a slide regarding the identification of additional genes associated with both deficient decidualization and PE.

FIG. 7B demonstrates the inhibition of rhRLX stimulated invasion by GM6001 (25 mM). Data from 2 experiments, 2 or 3 replicate wells per treatment, and one 20× magnification field per well. Expressed as number of counted cells with values presented as mean±SEM. *$p<0.05$ and *$p<0.001$ vs VEH in FIG. 7A; *$p<0.001$ vs all other treatments in FIG. 7B by Newman-Keuls Multiple Comparison test.

FIG. 9A are images of total nuclei stained with Hoechst for normoxia cells (1), hypoxia non-treated cells (2) and hypoxia rhRLX-treated cells (3). Note that the number of rhRLX-treated adherent cells (3) is similar to control (1) demonstrating the anti-apoptotic effect of the hormone. FIG. 9B is a graph illustrating the average of three separate experiments. In FIG. 9C, each experiment (1-3) is shown. The different treatments were normoxia (n=3 dishes per experiment), hypoxia untreated (n=2-3), and hypoxia with 300 ng/mL rhRLX (n=2-3). FIG. 9D are images depicting total nuclei stained with Hoechst dye (1); apoptotic nuclei stained with TUNEL reagent (2); and (3) the merged images. ImageJ software and a ratio of TUNEL positive to total nuclei was calculated to determine percent apoptosis.

FIG. 10A depicts the effect of recombinant human relaxin-2 (rhRLN) on HTR-8/SVneo cell death following serum starvation and hypoxia-reoxygenation injury as measured by PI staining and flow cytometry. FIG. 10B illustrates the concentration dependence of rhRLN (1, 3, 10, 30, 100 and 300 ng/mL) compared to vehicle (VEH) and 5% fetal bovine serum as a positive control. P<0.001 by ANOVA.* P<0.05, §P<0.1 vs VEH.

FIG. 11A is a Venn Diagram showing significant overlap (*P<0.0001 by Pearson's chi-square test) between DEG down-regulated in PE-CVS and DEG up-regulated in LSE (38 DEG, Table 10). FIG. 11B is a Venn Diagram showing significant overlap (*P<0.0001 by Pearson's chi-square test) between DEG down-regulated in PE-CVS and DEG up-regulated in endometrium with intDEC changes from EP, which lacks local trophoblast influence (32 DEG, Table 11). FIG. 11C is a Venn Diagram showing significant overlap (*P<0.0001 by Pearson's chi-square test) between DEG down-regulated in PE-CVS and DEG up-regulated in intDEC-EP endometrium and LSE (16 DEG, Table 12). There is also significant overlap between DEG up-regulated in intDEC-EP endometrium and LSE (382 DEG; *p<0.0001).

FIG. 12A is a Venn Diagram showing significant overlap (*P<0.0001 by Pearson's chi-square test) between DEG down-regulated in PE-CVS and DEG up-regulated in intDEC endometrium (37 DEG, Table 13). FIG. 12B is a Venn Diagram showing significant overlap (*P<0.0001 by Pearson's chi-square test) between DEG down-regulated in PE-CVS and DEG up-regulated in confDEC endometrium (46 DEG, Table 14) both from IUP with local trophoblast present. FIG. 12C is a Venn Diagram showing significant overlap (*P<0.0001 by Pearson's chi-square test) between DEG down-regulated in PE-CVS and DEG up-regulated in intDEC-EP endometrium (local trophoblast absent; also see FIG. 11B), and in intDEC-IUP endometrium (local trophoblast present). The majority of these DEG, in turn, are overlapping (30 DEG, Table 15; *p<0.0001) suggesting minimal trophoblast contribution to the overlap. There is also significant overlap between DEG up-regulated in intDEC-EP and intDEC-IUP endometrium (689 genes, *p<0.0001). FIG. 12D is a Venn Diagram showing no significant association (n=4 DEG, p=0.5) between DEG down-regulated in PE-CVS and DEG up-regulated by exposure of DEC stromal cells in culture to trophoblast conditioned medium (TrCM). There is significant overlap with DEG down-regulated in PE-CVS and up-regulated in confDEC-IUP endometrium (46 DEG), as well as 69 DEG in common between DEG up-regulated in TrCM and confDEC-IUP endometrium (both *p<0.0001). For abbreviations, also see Legend to FIG. 11.

FIG. 14A illustrates the average expression of 20 DEG down-regulated in chorionic villous samples obtained from women ~11 gestational weeks who developed preeclampsia 5-6 months later (PE-CVS; relative to CVS from normal pregnancy) and up-regulated in mid and late secretory endometrium (MSE and LSE, respectively; relative to proliferative phase endometrium, PrE). FIG. 14B illustrates the average expression of 13 DEG down-regulated in PE-CVS and up-regulated in intermediate (intDEC-IUP and -EP) and confluent decidualized (confDEC-IUP) endometrium, but not LSE. FIG. 14C illustrates the average expression for 16 DEG down-regulated in PE-CVS and upregulated in LSE, intDEC-IUP and -EP and confDEC-IUP endometrium (16 DEG). FIG. 14D is a heat map corresponding to FIG. 14C. The individual DEG in FIGS. 14A, 14B and 14C are listed in Table 16. nonDEC (non-decidualized endometrium from EP); for more abbreviations, see also Legends to previous figures. Significantly different (p<0.05) from: a, PrE; b, ESE; c, MSE; d, LSE; e, intDEC-EP; f, intDEC-IUP; g, nonDEC; h, PE-CVS.

FIG. 16A illustrates the intersection of differentially expressed genes (DEG) down-regulated in chorionic villous samples obtained from women ~11 gestational weeks who developed preeclampsia 5-6 months later (PE-CVS; relative to CVS from women with normal pregnancy) and in 93 DEG up-regulated in dNK, and in intDEC- and confDEC-IUP (p<0.0001). Seventy-four of these 112 and 93 DEG are in common (p<0.0001, Table 17). In FIGS. 16A and 16B (yellow shading), 16 DEG up-regulated in dNK are down-regulated in PE-CVS (p<0.0001). The gene symbols of these 16 DEG are listed in panel of FIG. 16C.

BRIEF DESCRIPTION OF THE TABLES

Figure 1:
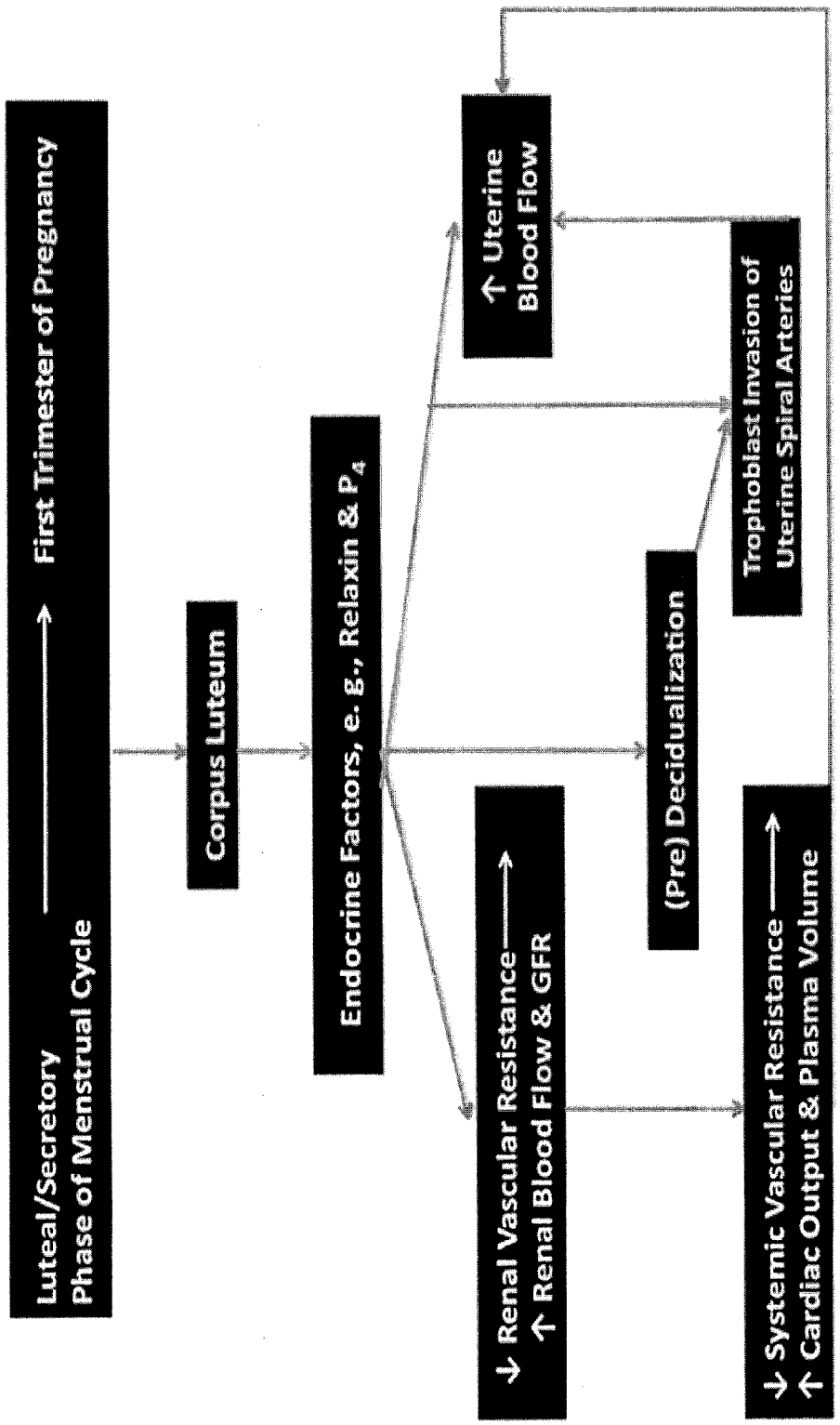
FIG. 1 is a flow diagram illustrating factors involved in endometrial and placental maturation.

Table 1. Genes differentially expressed in first trimester PE: Fold change data for CVS microarray.

Tables 2-6. Genes expressed in decidualization.

Table 7. DEG up-regulated in PE-CVS compared to NP-CVS.

Table 8. DEG down-regulated in PE-CVS compared to NP-CVS.

Table 9. Enriched Biological processes for DEG down-regulated in PE-CVS compared to NP-CVS (DAVID Bioinformatics Resources 6.7).

Table 10. Overlap of DEG down-regulated in PE-CVS and up-regulated in LSE.

Table 11. Overlap of DEG down-regulated in PE-CVS and up-regulated in intDEC-EP.

Table 12. Overlap of DEG down-regulated in PE-CVS and up-regulated in intDEC-EP & LSE.

Table 13. Overlap of DEG down-regulated in PE-CVS and up-regulated in intDEC-IUP.

Table 14. Overlap of DEG down-regulated in PE-CVS and up-regulated in confDEC-IUP.

Table 15. Overlap of DEG down-regulated in PE-CVS and up-regulated in intDEC-IUP and intDEC-EP.

Table 16. PE-CVS down-regulated genes linked to decidualization.

Table 17. Overlap of DEG up-regulated in dbNK and LSE plus intDEC-EP and intDEC-IUP plus confDEC-IUP (74 genes).

Table 18. Class prediction applying the k-Nearest Neighbors (kNN) algorithm for classification and the K-fold cross validation method as classifier.

DETAILED DISCLOSURE

The invention provides methods for treating and/or reducing the likelihood of development of a placental syndrome. In certain embodiments, the method for treating and/or reducing the likelihood of development of a placental syndrome comprises the steps of: (a) determining whether a woman has experienced a placental syndrome during a previous pregnancy; (b) if the woman has experienced a placental syndrome during a previous pregnancy, determining the late secretory/luteal (LS) phase of the menstrual cycle; and (c) administering a therapeutically effective amount of relaxin to the woman during the LS phase of menstruation to treat the placental syndrome.

In other embodiments, the methods for treating a placental syndrome comprise the steps of: (a) determining whether the woman is at risk for developing a placental syndrome; (b) if the woman is at risk, determining the late secretory/luteal (LS) phase of the menstrual cycle; and (c) administering natural or exogenous relaxin to the woman during the LS phase of menstruation. In a related embodiment, step (a) comprises obtaining a biological sample from the woman (such as blood, urine, uterine tissue (e.g., endometrial biopsy) or secretions) and measuring in the sample biomarker(s) that reflect endometrial maturation (pre-decidualization) or a deficiency thereof.

Abnormalities in (Pre)Decidualization and Disposition to PE

As described herein, numerous genes of putative decidual and NK cell origin being mostly downregulated in CVS from women who later developed PE (vide supra; Example 1 and Table 1) have been discovered. Some of the dysregulated genes identified as decidual in origin may also be expressed by Tr, e.g., EPAS1 or HIF-2α.

(pre)Decidualization begins in the LS phase. Abnormalities in decidual gene expression, as observed in the 1st trimester CVS of women who developed PE, may have commenced before conception. Thus, dysregulated gene expression in the LS endometrium appears to be an important factor in PE disease etiology.

According to the subject invention, supplemental hormonal support with relaxin, congener or mimetic during the LS phase, and in certain instances into early pregnancy, will improve endometrial maturation, thereby improving the uterine environment for Tr invasion and spiral artery remodeling, and thus treat and/or reduce the likelihood of development of placental syndromes, including PE.

Definitions

The terms "endogenous relaxin" or "natural relaxin" are used interchangeably herein and refer to the naturally occurring peptide hormone relaxin, which is well known in the art. Examples of endogenous relaxin include, but are not limited to, proteins associated with Relaxin 1 (RLN-1), Relaxin 2 (RLN-2), and Relaxin 3 (RLN-3) as well as with Relaxin/Insulin-Like Family Peptide Receptor (RXFP1) activity. In women, relaxin is produced by the corpus luteum of the ovary, the breast and, during pregnancy, also by the placenta, chorion, and decidua. Endogenous relaxin levels rise after ovulation as a result of its production by the corpus luteum and peak in the mid and late luteal phase of the menstrual cycle. If the cycle is nonconceptive, relaxin concentrations decline to undetectable. However, if the cycle is conceptive, relaxin concentrations rapidly increase and peak in the first trimester. Relaxin concentrations then begin a slow decline but remain elevated throughout gestation. The term relaxin (natural relaxin and endogenous relaxin) as used herein in reference to human subjects refers to H2 relaxin, unless otherwise specified.

The term "exogenous relaxin", as used herein, means non-endogenous human relaxin, including intact full length human relaxin or a portion of the relaxin molecule that retains biological activity. The term "exogenous relaxin" encompasses human H1 preprorelaxin, prorelaxin, and relaxin; H2 preprorelaxin, prorelaxin, and relaxin; and H3 preprorelaxin, prorelaxin, and relaxin. The term "relaxin" further includes biologically active (also referred to herein as "pharmaceutically active") relaxin from recombinant, synthetic or native sources as well as relaxin variants, such as amino acid sequence variants. As such, the term encompasses synthetic human relaxin and recombinant human relaxin, including synthetic H1, H2 and H3 human relaxin and recombinant H1, H2 and H3 human relaxin. The term further encompasses active agents with relaxin-like activity, such as relaxin agonists, relaxin mimetics and/or relaxin analogs and portions thereof that retain biological activity, including all agents that competitively displace bound relaxin from a relaxin receptor (e.g., LGR7 receptor, LGR8 receptor, GPCR135, GPCR142, etc.). Thus, a pharmaceutically effective relaxin agonist or mimetic is any agent with relaxin-like activity that is capable of binding to a relaxin receptor to elicit a relaxin-like response. In addition, the nucleic acid sequence of human relaxin as used herein does not necessarily have to be 100% identical to nucleic acid sequence of human relaxin (e.g., H1, H2 and/or H3) but may be at least about 40%, 50%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the nucleic acid sequence of human relaxin. Relaxin, as used herein, can be made by any method known to those skilled in the art. Examples of such methods are illustrated, for example, in U.S. Pat. No. 5,759,807 as well as in Bullesbach et al. (1991) The Journal of Biological Chemistry 266(17):10754-10761. Examples of relaxin molecules and analogs are illustrated, for example, in U.S. Pat. No. 5,166,191.

Naturally occurring biologically active relaxin may be derived from human, murine (i.e., rat or mouse), porcine, or other mammalian sources. Also encompassed is relaxin modified to increase in vivo half life, e.g., PEGylated relaxin (i.e., relaxin conjugated to a polyethylene glycol), modifications of amino acids in relaxin that are subject to cleavage by degrading enzymes, and the like. The term also encompasses relaxin comprising A and B chains having N- and/or C-terminal truncations. In general, in H2 relaxin, the A chain can be varied from A(1-24) to A(10-24) and the B chain from B(1-33) to B(10-22); and in H1 relaxin, the A chain can be varied from A(1-24) to A(10-24) and the B chain from B(1-32) to B(10-22). Also included within the scope of the term "relaxin" are other insertions, substitutions, or deletions of one or more amino acid residues, glycosylation variants, unglycosylated relaxin, organic and inorganic salts, covalently modified derivatives of relaxin, preprorelaxin, and prorelaxin. Also encompassed in the term is a relaxin analog having an amino acid sequence which differs from a wild-type (e.g., naturally-occurring) sequence, including, but not limited to, relaxin analogs disclosed in U.S. Pat. No. 5,811,395. Possible modifications to relaxin amino acid residues include the acetylation, formylation or similar protection of free amino groups, including the N-terminal, amidation of C-terminal groups, or the formation of esters of hydroxyl or carboxylic groups, e.g., modification of the tryptophan (Trp) residue at B2 by addition of a formyl group. The formyl group is a typical example of a readily-removable protecting group. Other possible modifications include replacement of one or more of the natural amino-acids in the B and/or A chains with a different amino acid (including the D-form of a natural amino-acid), including, but not limited to, replacement of the Met moiety at B24 with norleucine (Nle), valine (Val), alanine (Ala), glycine (Gly), serine (Ser), or homoserine (HomoSer). Other possible modifications include the deletion of a natural amino acid from the chain or the addition of one or more extra amino acids to the chain. Additional modifications include amino acid substitutions at the B/C and C/A junctions of prorelaxin, which modifications facilitate cleavage of the C chain from prorelaxin; and variant relaxin comprising a non-naturally occurring C peptide, e.g., as described in U.S. Pat. No. 5,759,807.

Also encompassed by the term "relaxin" are fusion polypeptides comprising relaxin and a heterologous polypeptide. A heterologous polypeptide (e.g., a non-relaxin polypeptide) fusion partner may be C-terminal or N-terminal to the relaxin portion of the fusion protein. Heterologous polypeptides include immunologically detectable polypeptides (e.g., "epitope tags"); polypeptides capable of generating a detectable signal (e.g., green fluorescent protein, enzymes such as alkaline phosphatase, and others known in the art); therapeutic polypeptides, including, but not limited to, cytokines, chemokines, and growth factors. All such variations or alterations in the structure of the relaxin molecule resulting in variants are included within the scope of this invention so long as the functional (biological) activity of the relaxin is maintained. Preferably, any modification of relaxin amino acid sequence or structure is one that does not increase its immunogenicity in the individual being treated with the relaxin variant. Those variants of relaxin having the described functional activity can be readily identified using in vitro and in vivo assays known in the art.

In some embodiments, the subject invention provides methods comprising administration of a relaxin agonist. In some methods, the relaxin agonist activates one or more relaxin-related G-protein coupled receptors (GPCR) examples of which include, but are not limited to, RXFP1, RXFP2, RXFP3, RXFP4, FSHR (LGR1), LHCGR (LGR2), TSHR (LGR3), LGR4, LGR5, LGR6LGR7 (RXFP1) and LGR8 (RXFP2). In some embodiments, the relaxin agonist comprises the amino acid sequence of Formula I of WO 2009/007848 of Compugen (herein incorporated by reference for the teaching of relaxin agonist sequences). Exemplary relaxin agonists are also disclosed in international application PCT/US2009/044251 of Corthera, which is hereby incorporated by reference for the teaching of relaxin agonist sequences of SEQ ID NOS:4-8. Contemplated relaxin agonists also include those disclosed by Xiao et al., "Identification and optimization of small-molecule agonists of the human relaxin hormone receptor RXFP1," *Nat Commun*, 4:1953 (2013).

The present disclosure also encompasses homologues of Formula I polypeptides, such homologues can be at least 50%, at least 55%, at least 60%, at least 65%, at least 70%, at least 75%, at least 80%, at least 85%, at least 85%, at least 90%, at least 95% or more say 100% identical to the amino acid sequence of an exemplary relaxin agonist (e.g., SEQ ID NO:5 or SEQ ID NO:6 of PCT/US2009/044251 of Corthera), as can be determined using BlastP software of the National Center of Biotechnology Information (NCBI) using default parameters, optionally and preferably including the following: filtering on (this option filters repetitive or low-complexity sequences from the query using the Seg (protein) program), scoring matrix is BLOSUM62 for proteins, word size is 3, E value is 10, gap costs are 11, 1 (initialization and (initialization and extension). Optionally and preferably, nucleic acid sequence identity/homology is determined with BlastN software of the National Center of Biotechnology Information (NCBI) using default parameters, which preferably include using the DUST filter program, and also preferably include having an E value of 10, filtering low complexity sequences and a word size of 11. Finally the present disclosure also encompasses fragments of the above described polypeptides and polypeptides having mutations, such as deletions, insertions or substitutions of one or more amino acids, either naturally occurring or artificially induced, either randomly or in a targeted fashion.

The term "late secretory/luteal (LS) phase" of the menstrual cycle refers to the phase that commences several days following ovulation (where an egg is released from the egg follicle on the ovary). This will depend upon the woman's cycle; in general the LS phase can commence at around 4 to 8 days following ovulation, preferably at around 5 to 7 days following ovulation, and more preferably at about 6 days following ovulation. This phase terminates if the egg is fertilized by sperm and then implants in the endometrium, following which pregnancy begins, or if the egg is not fertilized or does not implant and the endometrium begins to break down. The term "pregnancy" refers to the nine months (40 weeks from the last menstrual period) of pregnancy which is traditionally divided into three trimesters, i.e., distinct periods of roughly three months in which different phases of fetal development take place. The first trimester is a time of basic cell differentiation. It is believed to end at the mother's first perception of fetal movement (quickening), which usually occurs around the end of the third month (or about 12 to about 14 weeks of gestational age). The second trimester is a period of rapid growth and maturation of body systems (about 15 to about 28 weeks of gestational age). A second-trimester fetus born prematurely may be viable, depending on the hospital care. The third trimester marks the final stage of fetal growth, in which systems are completed, fat accumulates under the fetus' skin, and the fetus moves into position for birth (about 29 to about 42 weeks of gestational age). This trimester ends with the birth itself.

The term "placental syndromes" includes pre-eclampsia, intra-uterine growth restriction, pre-term labor, pre-term birth, impaired decidualization, recurrent spontaneous abortions, and/or compromised endometrial maturation.

The term "about" when used in the context of a stated value, encompasses a range of up to 10% above or below the stated value (e.g., 90-110% of the stated value). For instance, an intravenous (IV) infusion rate of about 30 mcg/kg/day, encompasses IV infusion rates of 27 mcg/kg/day to 33 mcg/kg/day.

"Therapeutically effective" refers to the amount of pharmaceutically active relaxin that will result in a measurable desired medical or clinical benefit to a patient, as compared to the patient's baseline status or to the status of an untreated or placebo-treated (e.g., not treated with relaxin) subject.

The term "nucleic acid" can be understood to mean, according to the present invention, either a double-stranded DNA, a single-stranded DNA or products of transcription of the said DNAs (e.g., RNA molecules).

The term "preeclampsia" as used herein refers to a condition that occurs during pregnancy, diagnosed by the new onset of high blood pressure accompanied by the presence of proteins in the urine and may include edema (swelling). Preeclampsia, sometimes called toxemia of pregnancy, is related to a more serious disorder called "eclampsia", which is preeclampsia together with seizure. These conditions usually develop during the second half of pregnancy (after 20 weeks), though they may develop shortly after birth (postpartum) or before 20 weeks of pregnancy.

The term "primer extension reaction" as used herein refers to any polymerization process mediated by the action of a nucleotide polymerase, e.g., a DNA polymerase, by extending a predetermined polynucleotide sequence that is at least partially complementary to a template sequence under appropriate conditions.

Probe set ID Nos: 207016_s_at; 231040_at; 236514_at; 242868_at; 1568736_s_at; 202363_at; 204041_at; 210164_at; 205291_at; 205495_s_at; 231798_at; 217143_s_at; 227238_at; 206785_s_at; 205992_s_at; 209763_at; 205445_at; 229839_at; 223786_at; 227816_at; 204741_at; 235019_at; 205493_s_at; 205067_at; 204580_at; 205870_at; 230748_at; 231818_x_at; 214702_at; 202768_at; 203592_s_at; 206067_s_at; 205302_at; 215388_s_at; 217767_at; 217552_x_at; 205654_at; 229902_at; 208084_at; 206638_at; 202917_s_at; 221286_s_at; 206859_s_at; 230848_s_at; 219759_at as set forth in Table 1 on the AFFYMETRIX GeneChip system (Affymetrix, Santa Clara, Calif.; HG-U133 Plus 2.0 GeneChips containing 53,613 probe sets), as used herein, refer to nucleic acid sequences found on the aforementioned AFFYMETRIX GeneChip system. The polynucleotide sequences are identified by database accession numbers (e.g., NM_006433.2, etc.) in Table 1 and each of the accession numbers are hereby incorporated by reference in their entireties.

"Standard control" or "control sample" as used herein refers to a sample suitable for use in a method of the present invention, e.g., in order for quantitatively determining the amount of a nucleic acid. Such a sample contains a known amount of the nucleic acid that closely reflects the average level of the nucleic acid in an average non-preeclamptic woman without symptoms of placental syndromes. In certain embodiments, a "standard control" may be derived from an average healthy non-pregnant woman.

"An increase and decrease in the amount of the nucleic acid or polypeptide species in the test sample as compared to the standard control" refers to a positive or negative change in amount from the standard control. An increase is preferably at least 2.00 fold, 2.25 fold, 2.50 fold, 2.75 fold, 3.00 fold, 3.25 fold, 3.5 fold, 3.75 fold, 4.00 fold, 4.25 fold, 4.50 fold, 4.75 fold, of 5.00 fold. Similarly, a decrease is at least 2.00 fold, 2.25 fold, 2.50 fold, 2.75 fold, 3.00 fold, 3.25 fold, 3.5 fold, 3.75 fold, 4.00 fold, 4.25 fold, 4.50 fold, 4.75 fold, of 5.00 fold. For example, an increase of 2+ or greater or −2 or below would be considered significant difference from control. These expression levels (+2 or −2) can also be referred to as "overexpressed"/"overexpression" or "underexpressed"/"underexpression".

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

"PCR primers" as used herein refer to oligonucleotides that can be used in a polymerase chain reaction (PCR) to amplify a nucleotide sequence originating from a nucleic acid (RNA transcript). Some aspects of the invention provide for primers that comprise the sequences of probe set ID Nos: 207016_s_at; 231040_at; 236514_at; 242868_at; 1568736_s_at; 202363_at; 204041_at; 210164_at; 205291_at; 205495_s_at; 231798_at; 217143_s_at; 227238_at; 206785_s_at; 205992_s_at; 209763_at; 205445_at; 229839_at; 223786_at; 227816_at; 204741_at; 235019_at; 205493_s_at; 205067_at; 204580_at; 205870_at; 230748_at; 213818_x_at; 214702_at; 202768_at; 203592_s_at; 206067_s_at; 205302_at; 215388_s_at; 217767_at; 217552_x_at; 205654_at;

229902_at; 208084_at; 206638_at; 202917_s_at; 221286_s_at; 206859_s_at; 230848_s_at; 219759_at as set forth in Table 1 on the AFFYMETRIX GeneChip system (Affymetrix, Santa Clara, Calif.; HG-U133 Plus 2.0 GeneChips containing 53,613 probe sets). Various combinations of the aforementioned primers can be included in a primer kit as set forth herein.

As used in this specification and the appended claims, the singular forms "a", "an", and "the" include plural reference unless the context clearly dictates otherwise. Additionally, the terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state. Thus, isolated peptides or nucleic acids, in accordance with the invention, preferably do not contain materials normally associated with the peptides in their in situ environment.

Determining Previous Placental Syndrome

Various methods are available for determining whether a woman has experienced a placental syndrome during a previous pregnancy. Such methods include, but are not limited to, determining whether the woman was previously diagnosed with PE, IUGR, preterm labor/birth and/or abnormal endometrial maturation/intrauterine growth. According to one embodiment of the subject invention, the woman's past health experience, particularly in pregnancy, would be used to determine whether the woman has experienced a placental syndrome.

Determining Risk for Developing a Placental Syndrome

In certain embodiments, the methods described herein include the step of determining whether a woman is at risk for developing a placental syndrome. In one embodiment, determining the risk for developing a placental syndrome comprises the following steps: (a) obtaining a biological sample from a woman and measuring in the sample biomarker(s) that reflect endometrial maturation (pre-decidualization) or a deficiency thereof. According to the subject invention, the biological sample can be blood, urine, uterine tissue (e.g., endometrial biopsy) or secretions, and the like. The biomarkers include proteins of relevant genes described herein.

Immunoassays can be used to detect at least one secreted protein disclosed herein, the expression levels of said at least one secreted protein, and comparison of said at least one secreted protein to a control (standard control) sample. Protein expression (secretion) can be detected by any suitable method, such as gas chromatography-mass spectrometry. In some embodiments, proteins are detected by immunoassays.

In one embodiment, the step for determining the risk for developing a placental syndrome comprises the steps of: obtaining a biological sample from a woman; quantitatively determining the amount of endogenous relaxin in the biological sample; and comparing the amount of the quantified amount of endogenous relaxin to a standard control representing the amount of the endogenous relaxin in the corresponding sample from an average non-preeclamptic woman without symptoms of placental syndromes; wherein an increase and decrease in the amount of the endogenous relaxin in the biological sample as compared to the standard control indicates an increased risk of developing placental syndromes, such as preeclampsia. In a preferred embodiment, at least one of the probe sets for RLN-1, RLN-2, RLN-3 and RXFP1 is provided and the amount of one or more nucleic acid species in the biological sample obtained from the woman that hybridizes with any one or more probe set ID is quantified and compared against a control sample.

In another embodiment, the step for determining the risk for developing a placental syndrome comprises the steps of:
obtaining a biological sample from a woman;
quantitatively determining the amount of one or more nucleic acid species or corresponding proteins or activities in the biological sample obtained from the woman that hybridizes with any one or more probe set ID Nos: 207016_s_at; 231040_at; 236514_at; 242868_at; 1568736_s_at; 202363_at; 204041_at; 210164_at; 205291_at; 205495_s_at; 231798_at; 217143_s_at; 227238_at; 206785_s_at; 205992_s_at; 209763_at; 205445_at; 229839_at; 223786_at; 227816_at; 204741_at; 235019_at; 205493_s_at; 205067_at; 204580_at; 205870_at; 230748_at; 213818_x_at; 214702_at; 202768_at; 203592_s_at; 206067_s_at; 205302_at; 215388_s_at; 217767_at; 217552_x_at; 205654_at; 229902_at; 208084_at; 206638_at; 202917_s_at; 221286_s_at; 206859_s_at; 230848_s_at; 219759_at as set forth in Table 1 on the AFFYMETRIX GeneChip system (Affymetrix, Santa Clara, Calif.; HG-U133 Plus 2.0 GeneChips containing 53,613 probe sets); and
comparing the amount of the quantified nucleic acid species to a standard control representing the amount of the nucleic acid species in the corresponding sample from an average non-preeclamptic woman without symptoms of placental syndromes; wherein an increase and decrease in the amount of the nucleic acid species in the biological sample as compared to the standard control indicates an increased risk of developing placental syndromes, such as preeclampsia. The biological sample can be blood, washing from the reproductive tract, urine, saliva, amniotic fluid, or uterine tissue (e.g., endometrial biopsy or chorionic villus). One aspect of the invention provides for increased expression of nucleic acids that hybridize with 205827_at; 215141_at; 202917_s_at; 215733_x_at; 234601_x_at; and decreased expression of nucleic acids that hybridize with 227238_at; 239010_at; 214702_at; 1553319_at; 235592_at; 229839_at; 230748_at; 203789_s_at; 226482_s_at; 215388_s_at; 1562053_at; 219911_s_at; 209351_at; 1552858_at; 215108_x_at; 226403_at; 207607_at; 228293_at; 210251_s_at; 1561318_at; 241036_at; 219759_at; 203592_s_at; 205302_at; 1568554_x_at; 1554276_at; 242842_at; 242868_at; 206859_s_at; 204580_at; 221286_s_at; 206859_s_at; 230848_s_at; 219759_at; and 207509_s_at.

In some embodiments, the first step can comprise the use of a reverse transcriptase polymerase chain reaction (RT-PCR). In other embodiments, the first step comprises using a polynucleotide hybridization method, or using a primer extension reaction.

Various other embodiments provide a kit for diagnosing whether a woman will have a propensity for developing a placental syndrome in a non-pregnant woman. This kit comprises the following: (i) PCR primers for quantitatively determining the amount of one or more nucleic acid species in a biological sample obtained from the non-pregnant woman, wherein the nucleic acid species hybridize with probe set ID Nos: 207016_s_at; 231040_at; 236514_at; 242868_at; 1568736_s_at; 202363_at; 204041_at; 210164_at; 205291_at; 205495_s_at; 231798_at; 217143_s_at; 227238_at; 206785_s_at; 205992_s_at; 209763_at; 205445_at; 229839_at; 223786_at; 227816_at; 204741_at; 235019_at; 205493_s_at; 205067_at;

204580_at; 205870_at; 230748_at; 213818_x_at; 214702_at; 202768_at; 203592_s_at; 206067_s_at; 205302_at; 215388_s_at; 217767_at; 217552_x_at; 205654_at; 229902_at; 208084_at; 206638_at; 202917_s_at; 221286_s_at; 206859_s_at; 230848_s_at; 219759_at as set forth in Table 1 on the AFFYMETRIX GeneChip system (Affymetrix, Santa Clara, Calif.; HG-U133 Plus 2.0 GeneChips containing 53,613 probe sets) and (ii) a standard control representing the amount of the nucleic acid species in the corresponding sample from an average non-preeclamptic woman without symptoms of placental syndromes.

As discussed above, immunoassays can be used to detect at least one secreted protein disclosed herein, the expression levels of said at least one secreted protein, and comparison of said at least one secreted protein to a control (standard control) sample. Protein expression (secretion) can be detected by any suitable method, such as gas chromatography-mass spectrometry. In some embodiments, proteins are detected by immunoassays.

Antibody binding is detected by techniques known in the art (e.g., radioimmunoassay, ELISA (enzyme-linked immunosorbant assay), "sandwich" immunoassays, immunoradiometric assays or Western blots. In some embodiments, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. In aspects of this invention, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. In other embodiments, the immunoassay described in U.S. Pat. Nos. 5,599,677 and 5,672,480; each of which is herein incorporated by reference.

In various aspects of the invention, the woman being examined is examined prior to pregnancy.

Determining Late Secretory/Luteal (LS) Phase of the Menstrual Cycle

The luteinizing hormone (LH) is always present in urine and increases 24-48 hours prior to ovulation. The LH surge triggers ovulation, which is the release of an egg from one of a woman's ovaries. The LS phase commences following ovulation and terminates either with implantation of an inseminated egg into the endometrium or when the endometrium commences breaking down. In certain embodiments of the invention, determination of the LS phase of the menstrual cycle is performed using a kit that is able to detect the LH surge. Such kits are readily available and have been disclosed in U.S. Pat. Nos. 3,991,174; 4,208,187; 6,234,974; and 6,451,619, all of which are incorporated by reference in their entirety.

Relaxin Compositions and Formulations

Relaxin, relaxin agonists, relaxin mimetics and/or relaxin analogs can be formulated as pharmaceuticals to be used in the methods of the invention. Any composition or compound that can stimulate a biological response associated with the binding of biologically or pharmaceutically active relaxin (e.g., synthetic relaxin, recombinant relaxin) or a relaxin agonist (e.g., relaxin analog or relaxin-like modulator or relaxin mimetic) to relaxin receptors can be used as a pharmaceutical in the disclosure. General details on techniques for formulation and administration are well described in the scientific literature (see Remington's Pharmaceutical Sciences, Maack Publishing Co, Easton Pa.). Pharmaceutical formulations containing pharmaceutically active relaxin can be prepared according to any method known in the art for the manufacture of pharmaceuticals. The formulations containing pharmaceutically active relaxin or relaxin agonists used in the methods of the invention can be formulated for administration in any conventionally acceptable way including, but not limited to subcutaneously (SQ), intramuscularly, intravenously, sublingually, topically, orally and via inhalation. Illustrative examples are set forth below. In one preferred embodiment, relaxin is administered subcutaneously (SQ).

When the drugs are delivered subcutaneously (SQ), the formulations containing pharmaceutically active relaxin or a pharmaceutically effective relaxin agonist can be in the form of a sterile injectable preparation, such as a sterile injectable aqueous or oleaginous suspension. For example, relaxin can be diluted in sodium acetate at pH 5.0 where it is very soluble and stable. Patients can be treated with a relaxin composition via continues infusion as long as necessary. For example, relaxin infusion pumps deliver relaxin through a cannula to a needle that is applied subcutaneously and the pumps can be worn on a belt under the patient's clothes. Relaxin can also be administered via timely relaxin injections while the patient is being monitored for symptoms of preeclampsia. Doses can be adjusted on a patient by patient basis. Relaxin suspensions can be formulated according to the known art using those suitable dispersing or wetting agents and suspending agents which have been mentioned above. The sterile injectable preparation can also be a sterile injectable solution or suspension in a nontoxic parenterally-acceptable diluent or solvent. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

Aqueous suspensions of the disclosure contain relaxin in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending relaxin in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid.

Dispersible powders and granules of the disclosure suitable for preparation of an aqueous suspension by the addition of water can be formulated from relaxin in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The pharmaceutical formulations of the disclosure can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

Administration and Dosing Regimen of Relaxin Formulations

The formulations containing pharmaceutically active H2 relaxin or a pharmaceutically effective H2 relaxin chimera, agonist, or mimetic used in the methods of the disclosure can be administered in any conventionally acceptable way including, but not limited to, subcutaneously, intramuscularly, intravenously, sublingually, topically, orally and via inhalation. Administration will vary with the pharmacokinetics and other properties of the drugs and the patients' condition of health. General guidelines are presented below.

The methods of the disclosure reduce the likelihood of the development of placental syndromes, such as preeclampsia, following insemination. The amount of relaxin alone or in combination with another agent or drug that is adequate to accomplish this is considered the therapeutically effective dose. The dosage schedule and amounts effective for this use, i.e., the "dosing regimen," will depend upon a variety of factors, including the general state of the patient's health, the patient's physical status, the type of pregnancy (e.g., single vs. multiple pregnancy) age, and the like.

In calculating the dosage regimen for a patient, the mode of administration is also taken into consideration. The dosage regimen must also take into consideration the pharmacokinetics, i.e., the rate of absorption, bioavailability, metabolism, clearance, and the like. Based on those principles, relaxin can be used to reduce or prevent development of preeclampsia in pregnant women. The subject invention also provides relaxin or a relaxin agonist or mimetic and, optionally, another drug for simultaneous, separate or sequential administration. For example, the disclosure provides relaxin and, optionally, a hypertensive medication for combined use in therapy if needed. In another example, the disclosure further provides relaxin and, optionally, $MgSO_4$ for seizure prophylaxis in combined therapy.

The subject invention also provides the use of relaxin in the manufacture of a medicament for reducing or preventing the development of placental syndromes, such as preeclampsia or IUGR, in pregnant women. As such, the medicament is prepared for administration during the LS phase of the menstrual cycle. The subject invention further provides relaxin or a relaxin analog or mimetic for use in a method of reducing the likelihood of the development of placental syndromes, such as preeclampsia, wherein relaxin is prepared for administration to non-pregnant women during the LS phase of the menstrual cycle.

The state of the art allows the clinician to determine the dosage regimen of relaxin for each individual woman. As an illustrative example, the guidelines provided below for relaxin can be used as guidance to determine the dosage regimen, i.e., dose schedule and dosage levels, of formulations containing pharmaceutically active relaxin administered when practicing the methods of the invention. As a general guideline, it is expected that the daily dose of pharmaceutically active H1, H2 and/or H3 human relaxin (e.g., synthetic, recombinant, analog, agonist, mimetic, etc.) is typically in an amount in a range of about 0.1 to about 100 µg/kg of subject body weight per day. In one preferred embodiment, the dosage of relaxin is 0.1 to 30 µg/kg/day throughout the LS phase of the menstrual cycle. More preferably, the daily dose of pharmaceutically active H1, H2 and/or H3 human relaxin (e.g., synthetic, recombinant, analog, agonist, mimetic, etc.) is administered to a woman to result in serum concentrations of relaxin of about 0.1-10.0 ng/ml during the LS phase of the menstrual cycle. In another embodiment, these dosages result, for example, in serum concentrations of relaxin of about 0.1-3.0 ng/ml during the LS phase of the menstrual cycle.

In one preferred embodiment, pharmaceutically effective relaxin or an agonist thereof is administered at about 0.1 to 30 µg/kg/day throughout the LS phase of the menstrual cycle and through the $1^{st}$, $2^{nd}$ or $3^{rd}$ trimester of pregnancy. In another preferred embodiment, pharmaceutically effective relaxin or an agonist thereof is administered at about 0.1 to about 30 µg/kg/day throughout the LS phase of the menstrual cycle and through the $1^{st}$ trimester of pregnancy. In another embodiment, the administration of relaxin is continued as to maintain a serum concentration of relaxin of from about 0.5 ng/mL to about 20 ng/ml, more preferably from about 0.5 to about 15 ng/ml, and most preferably from about 1 to about 10 ng/ml. Most preferably, the administration of relaxin is continued as to maintain a serum concentration of relaxin of 10 ng/ml or greater throughout pregnancy following administration during the LS phase of the menstrual cycle.

These relaxin concentrations can reduce the likelihood of the development of placental syndromes, including preeclampsia. In addition, these relaxin concentrations may treat and/or prevent symptoms in the mother that are associated with preeclampsia such as hypertension, high blood pressure, proteinuria, renal insufficiency and mortality Furthermore, these relaxin concentrations can reduce or prevent the likelihood of low birth weight in infants and associated risks as well as infant deaths. Depending on the subject, the relaxin administration is maintained for as specific period of time or for as long as needed to achieve the therapeutic efficacy described herein. For example, relaxin can be administered through continuous infusion through the LS phase. This can be achieved via an infusion pump or other means. Alternatively, relaxin can be administered through the LS phase and during the first and/or second trimester only if needed.

Figure 7:
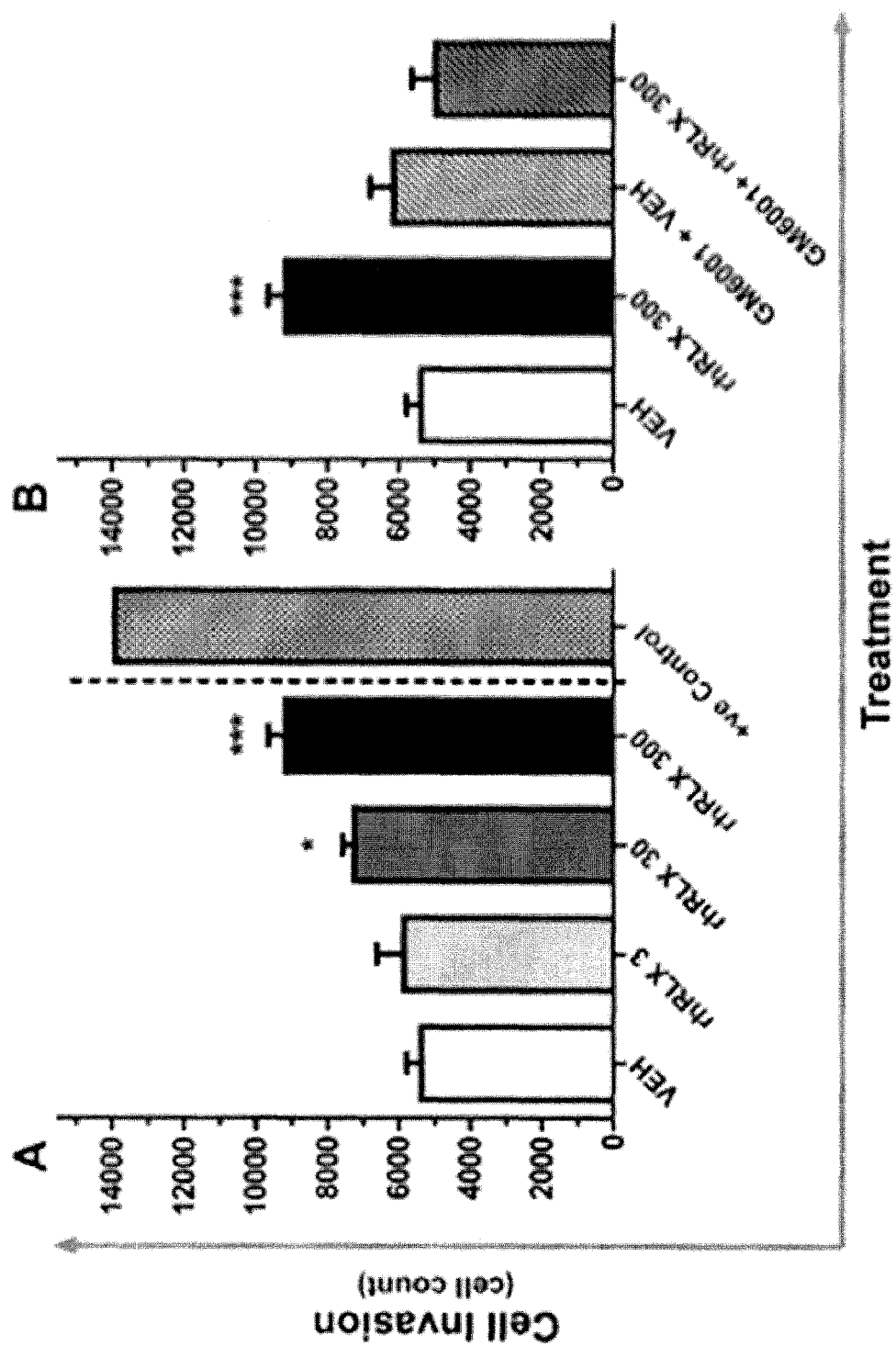
FIG. 7 are graphs illustrating relaxin ability to stimulate human trophoblast invasion in vitro. The effect of recombinant human relaxin-2 (rhRLX) and the general matrix metalloproteinase inhibitor (MMP), GM6001, on FIG. 7A, HTR-8/SVNeo cell invasion after 24 h in the Matrigel Invasion Assay (see following FIG. 8). Concentration dependence of rhRLX (3, 30, and 300 ng/ml) compared to vehicle for rhRLX (VEH), and 10% fetal bovine serum as positive control.
Figure 8:
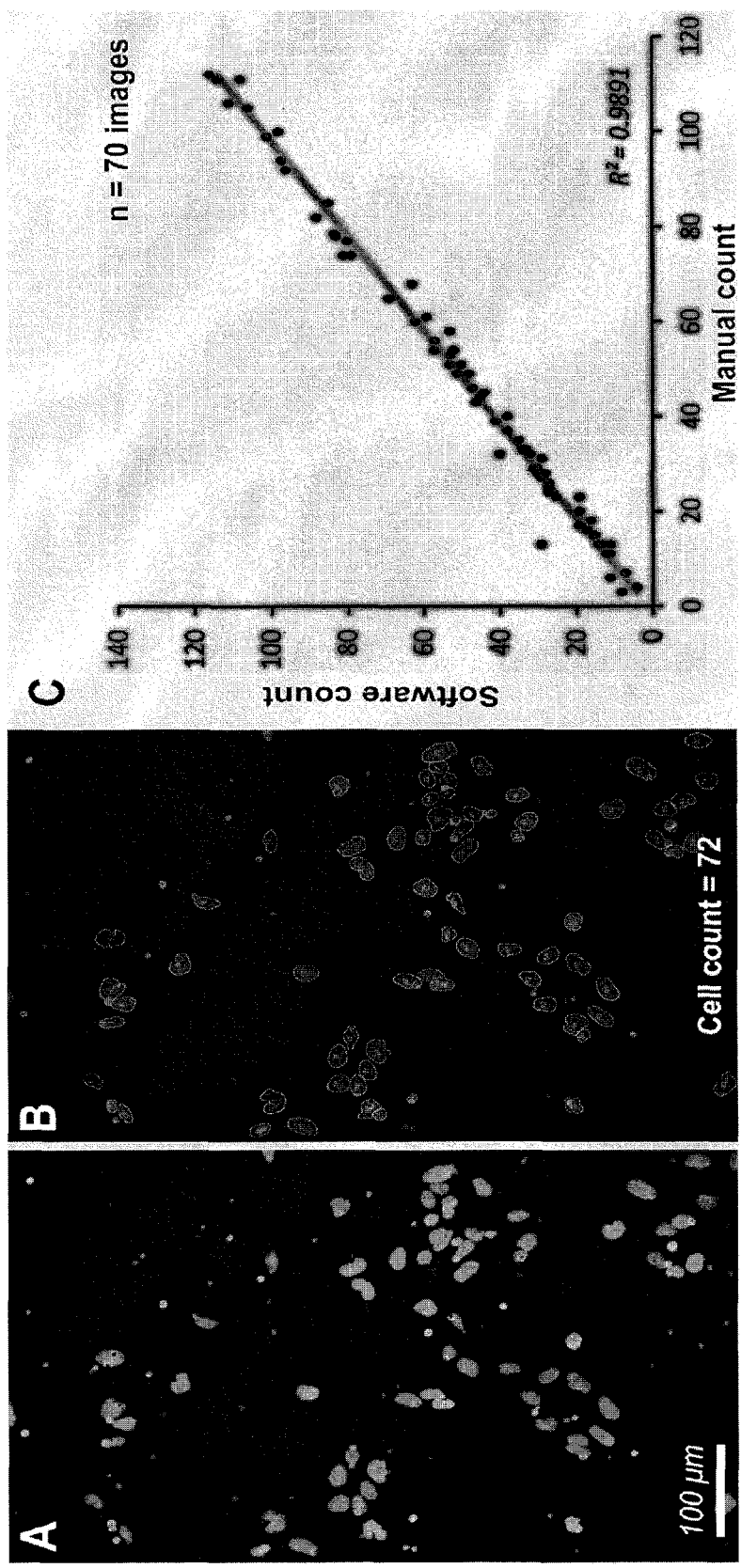
FIG. 8 are images and graphs illustrating the analysis of Matrigel Invasion Assay by epifluorescent microscopy and ImageJ. Pictures were obtained by epifluorescent microscopy (FIG. 8A) and than loaded in ImageJ software*. Images were converted to grayscale 8-bit pictures (FIG. 8B) and than analyzed with a Nucleus Counter plugin*. Analysis by ImageJ of pictures (n=70) taken at 100× magnification were correlated (C) to manual counting.
Figure 9:
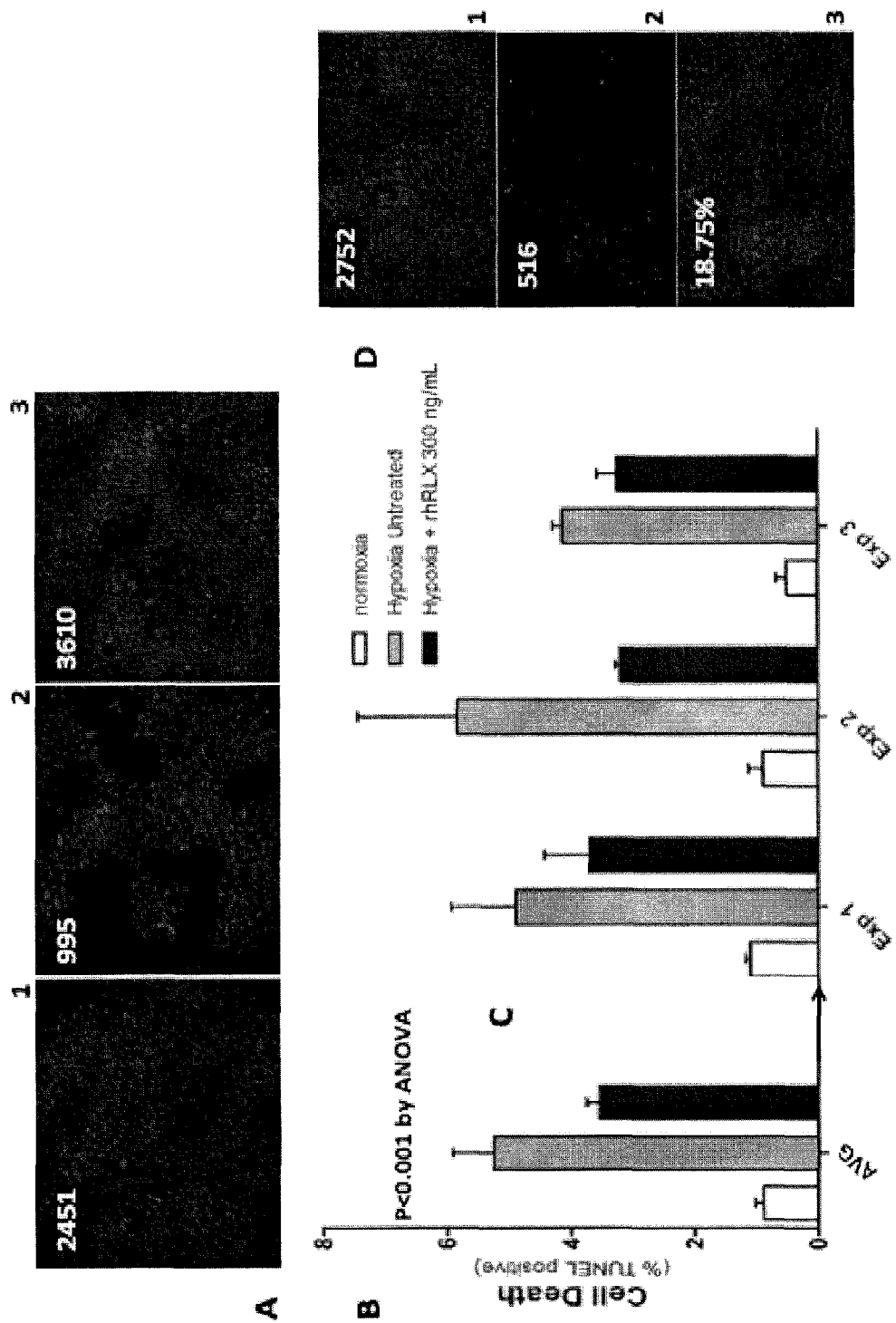
FIG. 9 are images and graphs demonstrating relaxin's ability to attenuate trophoblast cell apoptosis in vitro. Illustrated are the effects of recombinant human relaxin-2 (rhRLX) on HTR-8/SVneo cell death following serum starvation and hypoxia-reoxygenation injury as measured by TUNEL staining, microscopy and counting on ImageJ software.
Figure 10:
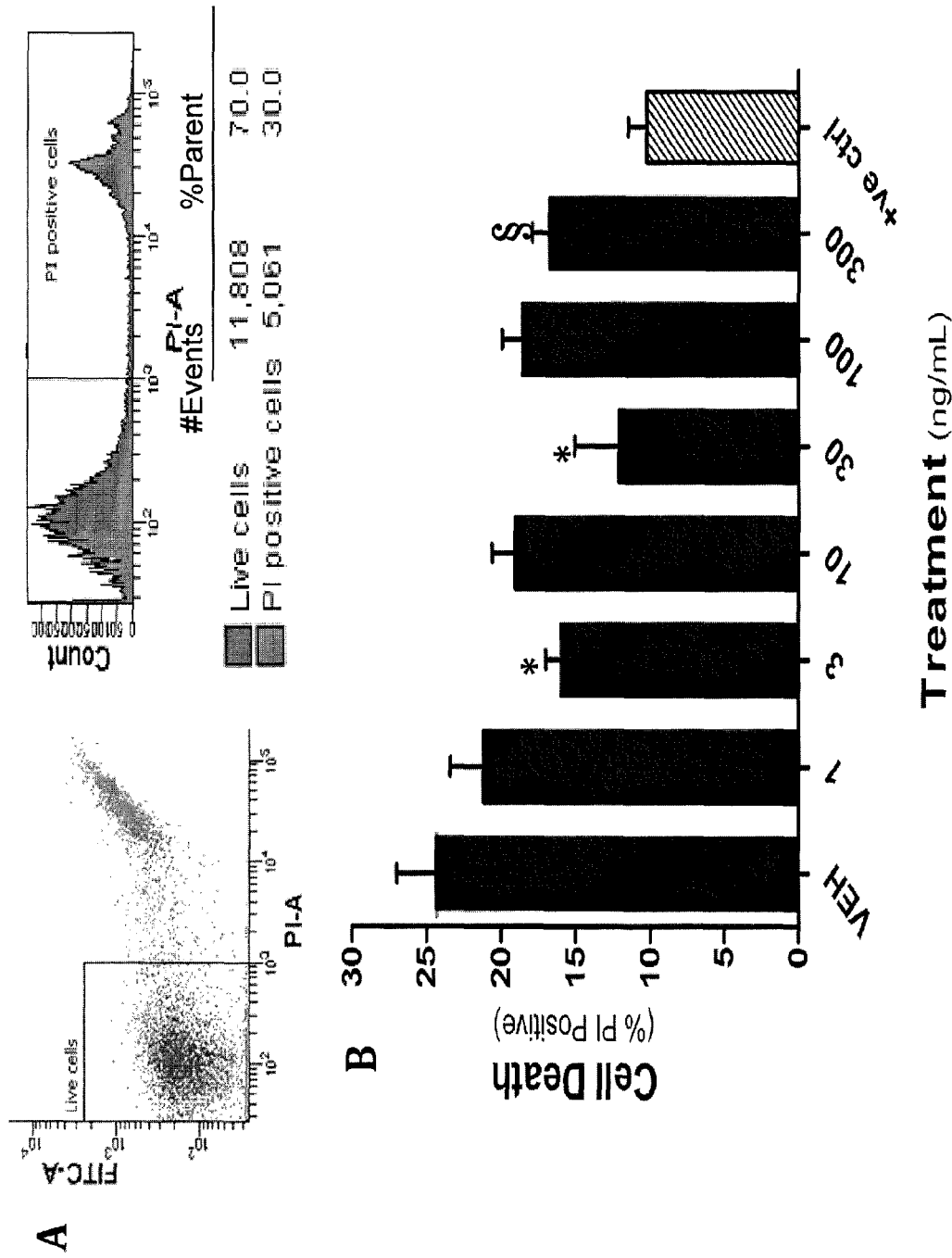
FIG. 10 are images and graphs demonstrating relaxin's ability to attenuate trophoblast cell death in vitro.

In certain embodiments, the method of the subject invention can be used to (1) correct deficient endometrial maturation ("(pre)decidualization"), thereby improving histiotrophic nutrition of the placenta and fetus before 10 weeks;

(2) promote trophoblast invasion (see FIGS. 7 and 8) and physiological remodeling of uterine spiral arteries, and hence, fetoplacental blood flow after 10 weeks; and (3) directly stimulate survival and invasion of trophoblast (see FIGS. 9 and 10), and thus, improve placentation and placental function; and augment maternal circulatory adaptations to pregnancy, which are deficient in women destined to develop severe preeclampsia or intrauterine growth restriction, particularly in the first trimester. The treatments described herein promote proper endometrial maturation prior to conception, which is beneficial in obviating PE development, as well as intrauterine growth restriction (IUGR) during pregnancy.

EXAMPLES

Identification of Differentially Expressed Genes

Materials and Methods: ~160 surplus chorionic villus sampling (CVS) over a 4-5 year period were collected. CVS is typically performed in women of advanced maternal age at 10-12 weeks of gestation to check for fetal chromosomal abnormalities. CVS also contains maternal decidual tissue. Four of the ~160 women developed PE ~6 months later and they were matched to 8 women with normal pregnancy (NP) outcome. These CVS tissues were subjected to DNA microarray, and it was discovered that 168 genes differentially expressed by J5 and/or fold change (FC) analyses in CVS between women who developed PE and those who experienced NP outcome (see FIG. 2 and Application Publication No. 20110171650, which is incorporated by reference in its entirety, including all figures, tables and amino acid or nucleic acid sequences). There was no evidence for upregulation of hypoxia or oxidative stress regulated genes at this early stage of pregnancy as observed in 3rd trimester PE placentas, suggesting these changes to be later events in the disease (see FIG. 3). Rather, there was dysregulation of several genes related to (pre)decidualization indicating that endometrial maturation, which occurs before (pre-decidualization) and after conception (decidualization) was impaired.

These data were reanalyzed specifically in the context of (pre)decidualization, and it was found that as many as 45 of the 168 dysregulated genes in CVS of women who developed PE ~6 months later are associated with this biological process (See Tables 1-6). Because decidual genes and pathways do not exist in commercially available bioinformatics software, the "Decidual Gene Set" consisting of 658 genes from Duncan W C et al. ("Ectopic pregnancy as a model to identify endometrial genes and signaling pathways important in decidualization and regulated by local trophoblast," *PLOS One.* 6(8): e23595 (2011)) was used (see FIG. 4). Twenty-four of the 168 dysregulated genes in CVS from women who developed PE overlap with this Decidual Gene Set. The probability of such extensive overlap occurring by chance is $p<10^{-20}$ (1-sided binomial exact test). Moreover, 20 of the 24 genes changed in a direction consistent with deficient decidualization in PE (i.e., opposite in direction to that observed for the same genes in the Decidualization Gene Set, p<0.0008).

It was discovered that an additional 21 of the 168 dysregulated genes in the CVS study (not represented in the "Decidual Gene Set" of Duncan et al.) were also previously identified in the literature to be associated with (pre)decidualization bringing the total number to 45 genes (Table 1; FIG. 5). Once again, it is highly significant (p<0.00001) that expression of 38 (highlighted in bold and italics in Table 1) of these 45 genes changed in a direction opposite to that observed for the biological process of (pre)decidualization. Noteworthy is the marked downregulation of genes classically associated with the decidual response such as prolactin −7.86, glycodelin −15.64 and IGFBP1 −10.35 in the CVS of women who developed PE compared to those with NP outcome (suggesting relative impairment of (pre)decidualization in the former). Ingenuity Pathway Analysis further revealed "Lack of endometrial Natural Killer (NK) Cells" (p=0.00092) and deficient "Activation of NK Cells" (p=0.00096) consistent with the downregulation of genes shown in Table 1 that are associated with NK cells (but not necessarily exclusively so) including granulysin, granzyme B, IL2RB, IL-15, IKZF1, and KLRC2. Indeed, uterine (u)NK cells comprise a large percentage of leukocytes in the (pre)decidualized endometrium. Taken together, these results from early pregnancy placentas suggest "decidualopathy" as part of the etiology of PE.

By extension, the results suggest that the antecedents of PE may actually precede conception residing in the LS endometrium. That is, dysregulation of endometrial gene expression may begin in the LS phase compromising endometrial maturation before conception (pre-decidualization), which persists and perhaps worsens after conception (decidualization), thereby disposing to impaired Tr invasion, inadequate placentation and PE (see FIG. 1). As the nomenclature implies, pre-decidualization and decidualization are a biological continuum. Uterine spiral arteries undergo morphological changes associated with the decidual response. Decidualization of spiral arteries may be permissive or play a direct role in promoting Tr invasion during early pregnancy (see FIG. 1). On this basis, inadequate (pre)decidualization may preclude optimal Tr invasion and spiral artery remodeling, thereby restricting blood flow to the placenta and fetus in women who develop PE.

To further support the findings herein, reduced glycodelin expression persists in the decidua of delivered placentas from women with PE, and serum IGFBP1 is decreased in women before developing PE. Moreover, uterine Natural Killer (uNK) cells normally increase in number during the LS phase associated with pre-decidualization, rising even further during the 1st trimester. Besides immune modulation, these cells play key roles in Tr lineage decisions, directing Tr invasion and mediating angiogenesis in the decidua.

Underscoring the importance of uNK and Tr cell interaction, certain polymorphic combinations of killer-cell immunoglobulin-like receptors (KIRs) and Tr HLA-C molecules increase the risk of PE. Thus, inadequate uNK cell number or maturation in the (pre)decidua as suggested in CVS from women who developed PE may play a causal role in the disease. Impaired (pre)decidualization could deprive the maternal-fetal interface of critical immune cells including uNK cells, cytokines and growth factors crucial for optimal Tr invasion and spiral artery remodeling that, in turn, are important for NP outcome (see FIG. 1).

The incidence of PE in women with endometriosis-associated infertility has been investigated. Unexpectedly, it was found that this condition significantly lowered the risk of PE compared to a control group (case group—0.8% vs. control group—5.8%, P=0.002). This finding establishes a precedent in which a pathological condition affecting the endometrium before pregnancy bears a significant relationship with the development of PE. More recently, data has been reported supporting aberrant pre-decidualization as a potential mechanism for recurrent pregnancy loss, again underscoring an important role for optimal endometrial maturation in NP outcome.

Prospective Study to Characterize LS Endometrium in Women Who Experienced Severe PE During Pregnancy Women who experienced severe PE will be enrolled before hospital discharge, using established diagnostic criteria of severe PE (n=8). Women matched for maternal age, race, ethnicity and parity with NP outcomes will likewise be recruited (n=8). After discontinuation of breastfeeding and resumption of normal menstrual cycles, the subject will be instructed to refrain from intercourse or use barrier contraception after a menstrual period. She will report to the clinic during the LS phase, day 10-12 post-LH surge, as documented by the Ovulation Predictor kit provided. Serum hCG will be analyzed; and if negative, endometrial biopsy (EnBx) will be obtained. Tissue will be processed for histology, flow cytometry, RNA, DNA and protein. Specimen quality and histology will be evaluated. Endometrial gene expression will be assessed by DNA microarray and selected genes validated using real time PCR. Endometrial proteins will be identified by iTRAQ and mass spectrometry. uNK cell number and maturation will be assessed by flow cytometry.

Figure 6:
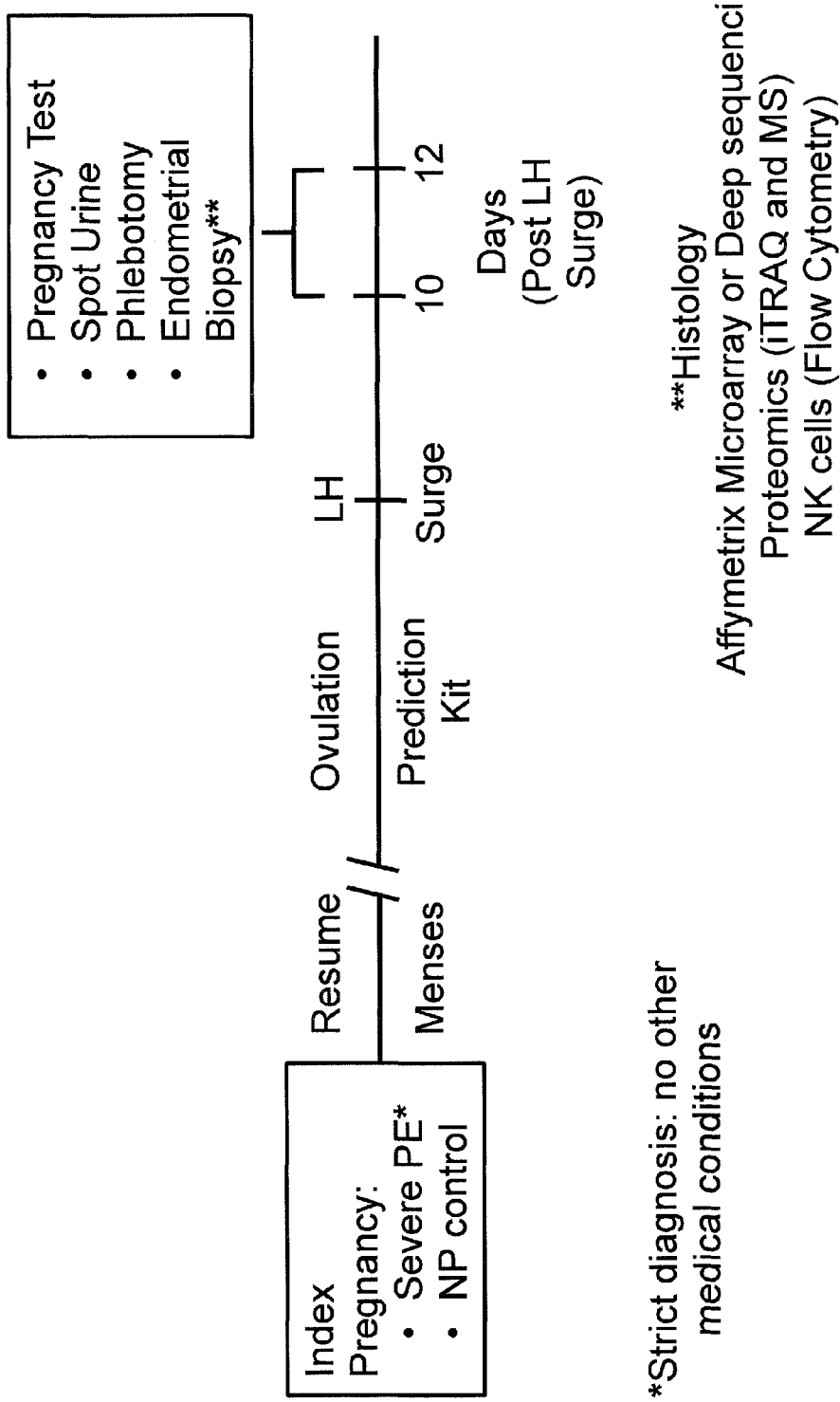
FIG. 6 illustrates steps involved in a prospective study to determine endometrial antecedents of preeclampsia.

Post-partum patients in Labor and Delivery and on the Obstetrics Floor who experienced severe PE or NP and who matched for maternal age, race and ethnicity will be approached. If the patient is interested in the study, then Study Coordinator will contact the subject to administer informed consent explaining the study, and provide the subject with instructions on how to complete the study. The Study Coordinator will schedule the EnBx and supervise collection and processing of endometrial tissue, blood and urine (see FIG. 6).

By restricting enrollment to severe PE without preexisting medical complications, disease heterogeneity should decrease, thereby increasing the likelihood of finding significant differences between the PE and NP cohorts.

Endometrial biopsy: EnBx will be obtained using a Pipelle biopsy catheter. This causes discomfort to the subject for ~10 seconds, but is safe and complications are rare. Because the subjects will not be actively bleeding, the expectation is to obtain mostly tissue and not blood or clots. The usual sample size is 0.25-0.5 g, sufficient tissue to perform the analyses; however, if any given sample is inadequate, then gene and protein expression will be analyzed first.

Blood and urine collection: Spot urine and blood samples for future study of biomarkers (as informed by EnBx study results) will be obtained immediately before EnBx.

DNA microarray: RNA will be extracted from endometrial tissues using TRI Reagent, and RNA quantification and integrity determined by Nanodrop and Agilent Bioanalyzer, respectively. cDNA will be synthesized from total RNA, and the cDNA will be used as a template for in vitro transcription (IVT). The antisense RNA synthesized during the IVT reaction will be used to generate sense DNA. Sense strand DNA will be fragmented, biotin labeled, and hybridized with rotation at 45° C. for 16 hours to the Affymetrix GeneChip® Human Gene 1.0 ST array. The arrays are washed and stained with reagents supplied in the GeneChip® Hybridization Wash and Stain kit on an Affymetrix Fluidics Station 450, and scanned with a GeneChip® 7G Scanner. Bioinformatics will be accomplished using Database for Annotation, Visualization and Integrated Discovery; and Kyoto Encyclopedia of Genes and Genome. Pathway Studio will be used to identify, build and visualize pathways that differ between subject groups. Published "Decidual Gene Sets and Pathways" will also be queried.

iTRAQ and Mass Spectrometry: For quantitative proteomics, a gel-free approach will be used with iTRAQ™ reagents from Applied Biosystems [38] and LC/MS/MS using the ThermoFinnigan LTQ-orbitrap that is available in the ICBR proteomics core. The experiment will be repeated three times in order to obtain data that can be evaluated statistically. To calculate a false discovery rate (FDR) for peptide-protein assignments, Proteomics System Performance Evaluation Pipeline (ProteomicS PEP, Applied Biosystems) in Protein Pilot™ will be used to create a reversed human decoy database to search.

Flow cytometry: Endometrial NK cell subsets will be analyzed using a BD LSRFortessa cell analyzer. Based on the gene array data, both CD56bright and CD56dim are expected to be diminished in frequency with a greater loss likely seen in the important pCD56bright CD16dim population. The analysis of cell subsets in small samples is ideally performed using FACS approaches and has been performed previously to quantitate and clone CD1d-restricted iNKT cells from human placenta.

Study to Determine if Defective Endometrial Maturation May Lead to Development of Preeclampsia The following describes a unique discovery based approach to study the etiology of PE. Surplus $1^{st}$ trimester placental villi were rapidly dissected and snap frozen within 5 minutes of extraction from women undergoing chorionic villous sampling (CVS) for prenatal genetic screening. Genome-wide gene expression profiling was utilized to study the placental (CVS) transcriptome of women who developed PE 5-6 months later or experienced a normal pregnancy. Unexpectedly, several characteristic molecular markers for decidualization (DEC) of the maternal endometrium, namely prolactin, insulin-like growth factor-binding protein 1 and glycodelin, were strongly down-regulated in CVS from PE relative to NP women (−7.7, −10.4 and −15.6 fold change, respectively).

The decidualized tissue in these isolated villi from CVS at least partly derives from placental septae projecting upward from the basal to the chorionic plate, which contains an admixture of decidual and immune cells, and Tr. DEC is a process of endometrial maturation that begins in the secretory phase of the menstrual cycle (preDEC) continuing after conception. An important part of this biological process is the appearance of decidual Natural Killer (dNK) cells in the secretory endometrium eventually comprising 30-40% of cells in the stromal compartment or 70-80% of all leukocytes in early pregnancy (32, 33). The origin of dNK cells is unclear, but they may arise from peripheral blood (pb) $CD56^{bright}$ NK (34-36) or $CD56^{dim}$ NK cells. In essence, preDEC and DEC are a biological continuum in preparation of the "soil" for the "seed" (conceptus).

Optimal endometrial maturation is emerging as an important precursor of successful pregnancy outcome. The following study findings obtained from CVS in the $1^{st}$ trimester of women remote from disease onset provide prospective evidence that one possible etiology of PE is deficient endometrial maturation.

Methods:

Publically available microarray datasets were analyzed in order to determine differentially expressed genes (DEG), which increase expression in late secretory endometrium (also known as pre-decidualization or endometrial maturation before implantation), during decidualization (endometrial maturation after implantation), the latter in the presence or absence of local trophoblast. In addition, DEG upregulated in decidual relative to peripheral blood NK cells were analyzed using other microarray datasets. These upregulated DEG were then compared to DEG down-regulated in chorionic villous samples (CVS) obtained at ~11 gestational weeks from 4 women who developed preeclampsia 5-6 months later matched to 8 women with normal pregnancy. This overall approach was chosen to support the provision that genes, which expression is increased during the process of normal endometrial maturation before and after implantation, will be decreased in the endometrium of women destined to develop preeclampsia.

Microarray datasets: Microarray dataset searches were performed in two public functional genomics data repositories: Gene Expression Omnibus (GEO) from the National Center for Biotechnology Information (NCBI) and the European Bioinformatics Institute from the European Molecular Biology Laboratory (EMBL-EBI). Both data repositories support MIAME-compliant data submissions.

One pre-condition for microarray dataset searches was the selection of microarray data in which RNA was hybridized to the Affymetrix Human Genome U133 Plus 2.0 Array (GPL570 for GEO; A-AFFY-44 for EMBL-EBI), the same platform used for the interrogation of CVS from PE and NP women (GSE12767). This pre-condition is necessary because it enables the direct comparison of the microarray data in the present work.

To search for preDEC data, the keywords entered were "endometrium" AND "menstrual cycle" AND GPL570 (or A-AFFY-44). Two datasets were selected from the GEO database: GSE4888 (Talbi S et al. (2006) Molecular phenotyping of human endometrium distinguishes menstrual cycle phases and underlying biological processes in normo-ovulatory women. *Endocrinology* 147:1097-1121) and GSE6364 (Burney R O et al. (2007) Gene expression analysis of endometrium reveals progesterone resistance and candidate susceptibility genes in women with endometriosis. *Endocrinology* 148:3814-3826). The dataset GSE4888 consisted of 27 samples obtained from women with normal ovulatory cycles. Twenty-one had histologic phenotypes of proliferative (PrE; n=4), early secretory (ESE; n=3), mid-secretory (MSE; n=8) or late secretory (LSE; n=6) endometrium, while 6 had ambiguous histological reading. The dataset GSE6364 consisted of 37 endometrial biopsies obtained from women without pathology (n=16) or diagnosed with some degree of endometriosis (n=21). Biopsy samples of the former were from PrE (n=5), ESE (n=3), and MSE (n=8). The 21 and 16 normal endometrial samples from GSE4888 and GSE6364, respectively, were pooled. The LSE phase was only represented by the 6 samples from GSE4888. To maintain equal number of replicates per stage of the endometrial cycle, 3 samples were randomly selected from each dataset for PrE, ESE and MSE. Thus, each of the 4 menstrual cycle phases was comprised of 6 endometrial samples (n=24 total).

To search for DEC data, the keywords employed were "endometrium" AND "decidualization" AND GPL570 (or A-AFFY-44). One dataset was selected from EMBL-EBI database: E-MTAB-680 (Duncan W C et al. (2011) Ectopic pregnancy as a model to identify endometrial genes and signaling pathways important in decidualization and regulated by local trophoblast. *PLoS One* 6:e23595). This dataset consisted of 24 endometrial samples collected at approximately 59 days of gestation. Of these, 13 were obtained from intrauterine pregnancies (IUP) and 11 from ectopic tubal pregnancies (EP). As reported by the authors, these samples presented different degrees of decidualization as assessed by morphology in H&E stained sections. The IUP samples were classified as confluent DEC (confDEC-IUP, n=7) or intermediate DEC (intDEC-IUP, n=6), while the EP samples were intermediate DEC (intDEC-EP, n=6) or without DEC changes (nonDEC, n=5). The presence or absence of trophoblast was determined by cytokeratin staining.

The keyword employed to evaluate the trophoblast influence on the decidualization process were "trophoblast" AND "decidualization" AND "endometrium" AND GPL570 (or A-AFFY-44). One dataset met the search criteria GSE5809 (GEO database) or E-GEOD-5809 (EMBL-EBI database) (Hess A P et al. (2007) Decidual stromal cell response to paracrine signals from the trophoblast: amplification of immune and angiogenic modulators. *Biol Reprod* 76:102-117). Human endometrial stromal cells were decidualized in culture or left untreated serving as a control. The DEC and nonDEC cells were then incubated with conditioned media from human trophoblast (TrCM) for 0 (n=3), 3 (n=6) and 12 (n=5) hours. Cytotrophoblasts were isolated from placentae obtained after elective pregnancy termination (6-22 gestational weeks), and they were cultured on Matrigel-coated matrix for 48 hours before harvesting of the conditioned media.

To approximate DEG up-regulated in NK cells during the preDEC or DEC process, a comparison between gene expression of decidual (d)NK or endometrial (e)NK cells and peripheral blood (pb)NK cells was conducted. To this end, Koopman et al. generously provided the microarray datasets performed on dNK cells (n=9) and pbNK cells (n=10) cells (Koopman L A et al. (2003) Human decidual natural killer cells are a unique NK cell subset with immunomodulatory potential. *J Exp Med* 198:1201-1212). In this study, decidual samples were collected from pregnant woman between 6 to 12 weeks of gestation after elective termination, and dNK cells were isolated by fluorescence-activated cell sorting. The same technique was employed to isolate pbNK cells from peripheral blood mononuclear cells of healthy donors (n=5 $CD56^{bright}$ pbNK and n=5 $CD56^{dim}$ pbNK). The isolated RNA was amplified, labeled and hybridized to the Affymetrix Human Genome U95 Version 2 Array (GPL8300). This platform is not the same as the others employed for the datasets described above. However, results from the analysis of this dataset are comparable, insofar as data imputation, normalization and transformation are the same.

Data Analysis:

Data input: Bioconductor software for the R software environment was employed for all the analyses. The gcRMA package was employed to import the raw data into R, perform background correction, as well as normalize and summarize the data. Then, rows of each data set were collapsed, in order to retain the microarray probe with the highest mean value (Max mean) from the group of the genes with the same official symbol. The function applied was the "collapseRows" from the WGCNA package (Langfelder P, Horvath S (2008) WGCNA: an R package for weighted correlation network analysis. *BMC Bioinformatics* 9:559). The purpose of row collapsing is to obtain unique identifiers for each gene in the working data set. Thus, from the original platform GPL570, containing 54675 probes, 21049 probes belonging to unique genes were retained for further analysis. For the platform GPL8300 employed in the NK cell dataset, 9127 probes related to unique genes were retained from 12625 probes.

Statistical analysis—LSE (or preDEC): data from biopsy samples in GSE4888 and GSE6364 (n=24) were analyzed using time as an ordinal variable. The Bayesian Estimation of Temporal Regulation (BETR) algorithm (Aryee M J et al. (2009) An improved empirical bayes approach to estimating differential gene expression in microarray time-course data: BETR (Bayesian Estimation of Temporal Regulation). *BMC Bioinformatics* 10:409) was used to identify the DEG at a False Discovery Rate (FDR) of <0.05. The first phase of the endometrial cycle (PrE) was considered as the baseline measurement and was compared to subsequent stages of the endometrial cycle, in order to correlate the differential expression among the various stages. This method, which is applied with the BETR package, provides the probabilities of differential expression for each gene in the data set. Genes with a probability higher than 99.99% were considered as differentially expressed genes (DEG).

Next, DEG selected by the BETR analysis were subjected to a supervised weighted gene co-expression network analysis employing the WGCNA package. The automatic method was employed for block-wise network construction and module detection. The co-expression similarity was raised to a soft thresholding power ($\beta$) of 12 to calculate adjacency. The adjacency for the signed network is defined as $a_{ij}=|(1+cor(x_i,x_j))/2|^\beta$ (Zhang B, Horvath S (2005) A general framework for weighted gene co-expression network analysis. *Stat Appl Genet Mol Biol* 4:Article17). The resulting modules for each network were related to the phase of the endometrial cycle in order to identify modules or clusters of co-expressed genes showing increasing expression pattern with progression through the endometrial cycle and peaking in the late secretory phase. Gene significance (GS) was defined as the correlation of i-th gene with a temporal pattern. Module membership (MM) was defined as the correlation of the i-th gene with respect to its corresponding module (the higher the MM the more connected is the i-th gene with the other genes of the corresponding modules). The correlation coefficient of MM and GS was measured for each module, plotting MM versus GS. Higher correlation between MM and GS indicates that genes that are highly associated in a temporal pattern are also the central elements of a given module (73). The module with the highest positive correlation between MM and GS was selected for further comparison with DEG down-regulated in PE- vs NP-CVS.

Statistical analysis—DEC: data from the intDEC-EP (n=6) or intDEC-IUP (n=6) and confDEC-IUP (n=7) endometrium in the E-MTAB-680 database were compared to nonDEC samples (n=5) from EP to determine DEG up-regulated during the biological process of DEC. The limma package was used for the statistical analysis, applying the empirical Bayes method proposed by Smyth (Smyth G K (2004) Linear models and empirical bayes methods for assessing differential expression in microarray experiments. *Stat Appl Genet Mol Biol* 3:Article3). This method calculates a moderated t-statistic for differential expression of each gene by performing a linear model fit of the data. Then, an empirical Bayes step is applied to moderate the standard errors of the estimated log-fold changes in order to produce more stable estimates, especially when the number of replicates is small. A gene was considered to be significantly differentially expressed, if both of the following conditions were met: 1) the ratio of the normalized intensity of the intermediate or confluent DEC to normalized intensity of the nonDEC endometrial samples was higher than a 2-fold change; and 2) differences were considered statistically significant at $P \leq 0.05$.

Statistical analysis—Potential Influence of Trophoblast: data from cultured endometrial stromal cells in GSE5809 (n=14) were analyzed over time (0, 3 and 12 hours incubation with TrCM) and by two conditions (DEC and nonDEC cultured endometrial cells). The BETR algorithm was used to identify DEG between decidualized endometrial cells treated with TrCM and nonDEC endometrial stromal cells treated with TrCM at a FDR <0.05 as a function of TrCM incubation time (0, 3 and 12 hours). This method yields the probability of differential expression for each gene in the data set. Genes with a probability of 99.9% were considered as DEG. Co-expressed genes as determined by WGCNA (see above) increasing in expression by 12 hours of incubation with TrCM were selected for further comparison with DEG down-regulated in PE-vs NP-CVS.

Statistical analysis—Decidual NK Cells: data from dNK (n=9) were compared to $CD56^{dim}$ pbNK (n=5) or $CD56^{bright}$ pbNK (n=5) by the empirical Bayes method as described above. A gene was considered to be significantly differentially expressed if both of the following conditions were met: 1) the ratio of the normalized intensity of the dNK to normalized intensity of the pbNK samples was higher than a 2-fold change; and 2) differences were considered statistically significant at $P \leq 0.05$.

Statistical analysis—PE-CVS: data from PE-CVS (n=4) and NP-CVS (n=8) in the dataset GSE12767 were compared by the empirical Bayes method. The DEG were considered if both of the following conditions were met: 1) the ratio of normalized intensity in PE-CVS to normalized intensity in CVS samples from normal pregnancy exceeded a 1.5-fold change; and 2) differences were considered statistically significant at $P \leq 0.05$. To expand the number of genes, down-regulated DEG determined by J5 and FC analysis were also included from Founds and coworkers (see Table 2 and Table S1 in Founds S A et al. (2009) Altered global gene expression in first trimester placentas of women destined to develop preeclampsia. *Placenta* 30:15-24).

Class prediction: in order to evaluate the performance of the selected DEG in each dataset, class prediction applying the k-Nearest Neighbors (kNN) algorithm for classification and the K-fold cross validation method as classifier was performed. The methodology was performed with the RWeka package for R (Hornik K, Buchta C, Zeileis A (2009) Open-source machine learning: R meets Weka. *Computational Statistics* 24:225-232). Specifically, after gene selection by the corresponding statistical method, each sample was examined for that dataset to determine if it would be able to predict to which class it belongs according the Euclidean distance to its kNN. For this, the K-folds number was set to the n samples for each dataset, known as leave-one-out cross validation (LOOCV). The k number for KNN was set as $n_i-1$, for $n_i$ being the number of samples in the class of interest. The corresponding K-fold and k numbers, and the number of correct classifications for each dataset are shown in Table 18 below:

TABLE 18

| Dataset | LSE | intDEC-EP | intDEC-IUP | confDEC-IUP | PE-CVS | dNK |
|---|---|---|---|---|---|---|
| Classes | PrE, ESE, MSE, LSE (n = 24) | intDEC-EP, NonDEC (n = 11) | intDEC-IUP, NonDEC (n = 11) | confDEC-IUP, NonDEC (n = 13) | PE-CVS, NP-CVS (n = 8) | dNK, pbNK (n = 17) |

TABLE 18-continued

| Class of interest | LSE ($n_i = 6$) | intDEC-EP ($n_i = 6$) | intDEC-IUP ($n_i = 6$) | intDEC-IUP ($n_i = 7$) | PE-CSV ($n_i = 4$) | dNK ($n_i = 9$) |
|---|---|---|---|---|---|---|
| K-fold | 24 | 11 | 11 | 13 | 12 | 17 |
| kNN | 5 | 5 | 5 | 6 | 3 | 9 |
| Number of correct classifications | 24 (100%) | 11 (100%) | 11 (100%) | 13 (100%) | 12 (100%) | 13 (100%) |

Data comparison: the DEG down-regulated in PE-CVS were compared to: (i) the cluster of co-expressed endometrial genes increasing expression by the late secretory phase of the menstrual cycle (preDEC); (ii) DEG up-regulated in intermediate DEC endometrium from IUP or EP with and without trophoblast, respectively, and confluent DEC from IUP; (iii) the cluster of co-expressed genes increasing expression in decidualized endometrial stromal cells in culture after 12 hours of incubation with TrCM; and (iv) DEG up-regulated in decidual relative to peripheral blood NK cells. Statistical comparisons were made by the test of independence (Pearson's chi-square test) to determine the relatedness between down-regulated DEG in PE-CVS and up-regulated DEG in LSE, intermediate DEC (IUP or EP) and confluent DEC endometrium, in decidualized stromal cells in culture treated with TrCM, and decidualized NK cells.

Systematic Literature Search

Systematic review of the literature was undertaken by electronic searches in Medline through PubMed without language or publication date restrictions. The goal was to identify all publications related to decidualization that also reported one or more of the DEG down-regulated in PE-CVS (n=195). To enable identification of all relevant publications, Human Genome Organisation (HUGO) approved gene symbols were searched, as well as previous symbols and synonyms as listed by HUGO. The electronic search strategy was based on the Medical Subject Heading (MeSH) for each gene name, and when applicable, combined with title/abstract searches with all gene symbol synonyms. Synonyms that were not specific for a gene and generated too many irrelevant abstracts were omitted from the search string. By the use of Boolean operators individual gene searches (n=195) were combined with a search strategy identifying titles/abstracts related to "decidua/decidualization" based on the MeSH "decidua" or a title/abstract search for "decidua*".

Figure 13:
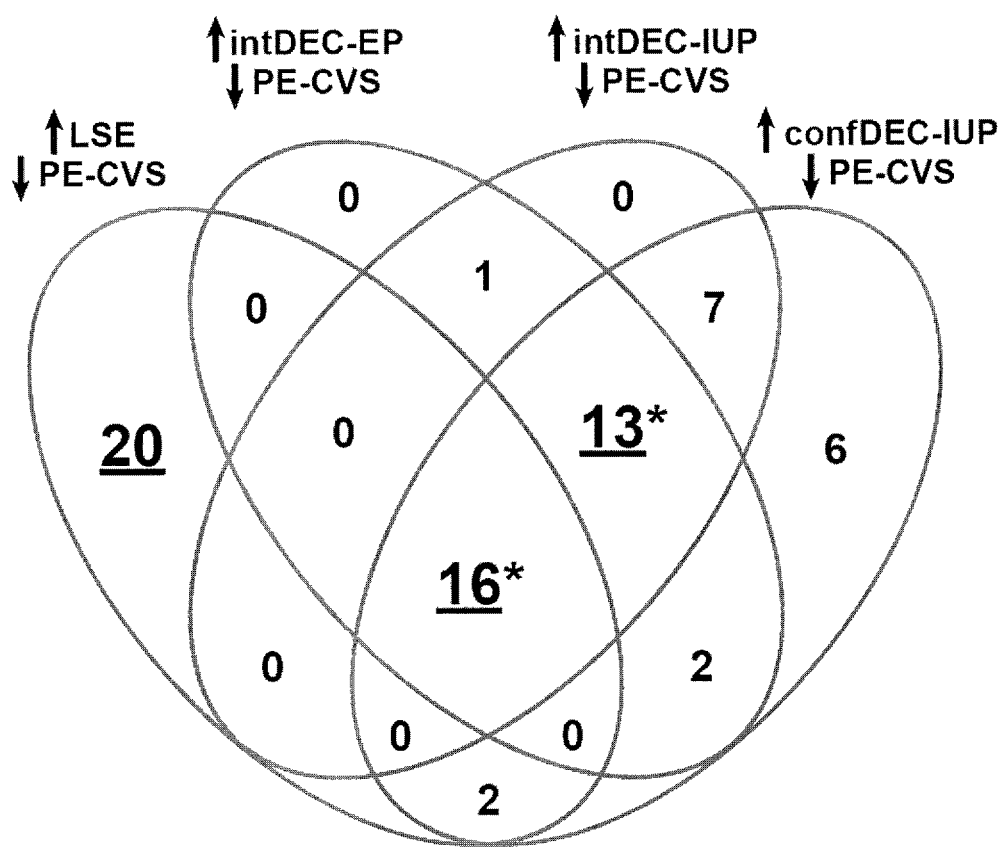
FIG. 13 is a Venn Diagram illustrating the confluence of overlapping differentially expressed genes (DEG) down-regulated in chorionic villous samples obtained from women ~11 gestational weeks who developed preeclampsia 5-6 months later (PE-CVS; relative to CVS from women with normal pregnancy) and DEG up-regulated in: LSE (relative to proliferative endometrium); endometrium with intDEC and confDEC changes from IUP; and intDEC changes from EP (all relative to EP endometrium without decidual changes). There are 20 DEG down-regulated in PE-CVS and uniquely up-regulated in LSE. There is significant overlap (*p<0.0001 by Pearson's chi-square test) between DEG down-regulated in PE-CVS and up-regulated in intDEC-EP and —IUP and confDEC-IUP endometrium, but not LSE (13 DEG); and in LSE, intDEC-EP and —IUP, and confDEC-IUP endometrium (16 DEG). See Table 16 for individual genes and FIG. 14 for average expression levels of these genes. For abbreviations, also see Legends in FIGS. 11 and 12.

Retrieved references reporting DEG(s) down-regulated in PE-CVS and "decidua/decidualization" in title/abstract were selected by two reviewers (EPU and KPC) who independently scrutinizing titles and abstracts. Full-text articles of any ambiguous references were selected by one reviewer (EPU) and further scrutinized by two reviewers (EPU and KPC) to determine whether there was a clear relationship between the DEG(s) down-regulated in PE-CVS with decidua/decidualization. As a reference, the PubMed identifier (PMID) of one of the most relevant publications for each gene related to decidualization was provided (Table 8). For all the DEG down-regulated in PE-CVS (n=195), the test of independence (Pearson's chi-square test) was applied to determine the relatedness between DEG identified by the system biology approach (n=67, FIG. 13), and genes identified by the literature search in Pubmed (n=31).

Differentially expressed genes (DEG) between PE and NP-CVS: chorionic villous samples (CVS) obtained at ~11 gestational weeks from 4 women who developed preeclampsia 5-6 months later matched to 8 women with normal pregnancy, as described in Example 1 herein. Women were diagnosed with PE according to published criteria, three delivered after 34 weeks of gestation, and all met criteria for severe disease. The 12 women did not have associated co-morbidities except those with PE tended to have higher BMI. A wide net was cast and included differentially expressed genes (DEG) determined by FC, t-test ($p<0.05$) and J5 for subsequent bioinformatics analysis. The results of the J5 analysis were taken from Example 1 herein, those from t-test were obtained by re-analyzing the original Affymetrix data GSE12767, and FC data stemmed from both the original (< or >2.0) and re-analysis (< or >1.5). There was a total of 396 DEG between PE-CVS and NP-CVS of which 201 were up-regulated and 195 down-regulated in PE-CVS (Tables 7-8).

Significant overlap between DEG in PE-CVS and DEG associated with decidualization: there was a significant overlap between DEG in PE- relative to NP-CVS and DEG in late secretory endometrium (LSE; relative to proliferative endometrium, PrE) (75 DEG); endometrium with intermediate decidual (intDEC) changes from tubal ectopic pregnancy (EP) (70 DEG); as well as endometrium from intDEC (71 DEG) and confluent (99 DEG) decidual (confDEC) changes from intrauterine pregnancy (IUP), all compared to EP endometrium without decidual changes (nonDEC) ($p<0.0001$ except LSE $p<0.003$). Twenty-four of these DEG were in common. Moreover, most of the overlapping DEG down- or up-regulated in PE-CVS changed in the opposite direction in the other data sets: 54/75, 52/70, 55/71 and 70/99, respectively, with 18 in common.

Analyses were then performed on DEG up-regulated during the biological processes of LSE, intDEC, and confDEC reasoning that if significant numbers of these DEG were down-regulated in PE-CVS, then the concept of deficient preDEC and DEC in women destined to develop PE would be supported. The top Enriched Biological Processes for these 195 DEG down-regulated in PE were defense response, inflammatory response, response to wounding and negative regulation of cell proliferation (all Benjamini corrected $p<0.05$; Table 9).

Figure 11A:
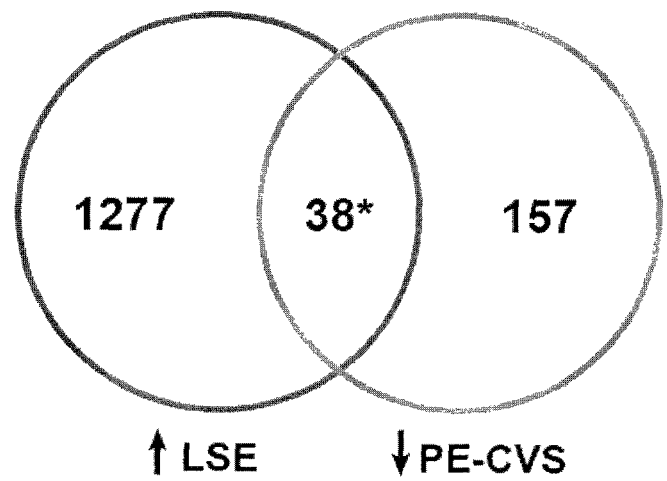
FIGS. 11A-11C are Venn Diagrams showing differentially expressed genes (DEG) down-regulated in chorionic villous samples obtained from women ~11 gestational weeks who developed preeclampsia 5-6 months later (PE-CVS; relative to CVS from women with normal pregnancy) and their overlap with DEG up-regulated in late secretory endometrium (LSE; relative to proliferative phase endometrium) and with endometrium with intermediate decidual (intDEC) changes from tubal ectopic pregnancies (EP; relative to EP endometrium without decidual changes).

Significant overlap between DEG down-regulated in PE-CVS and DEG up-regulated in LSE and intDEC-EP endometrium: gene expression in normal endometrium from different phases of the menstrual cycle were analyzed (GSE4888 and GSE6364) using time as an ordinal variable to determine temporal changes in DEG relative to the proliferative phase of the menstrual cycle. These genes were clustered by supervised weighted gene co-expression analysis, in order to identify the cluster of co-expressed genes strongly increasing expression in the endometrium throughout the menstrual cycle and peaking in the LSE. There was a significant overlap of 38 genes between the LSE cluster of 1315 up-regulated DEG and the 195 down-regulated DEG in PE-CVS ($p<0.0001$ by Pearson's chi-square test; FIG. 11A, see also Table 10 for gene list).

Figure 11B:
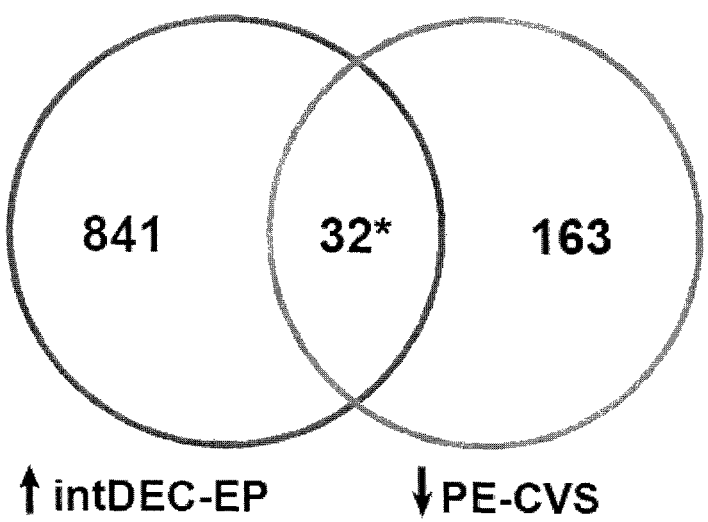
Figure 11C:
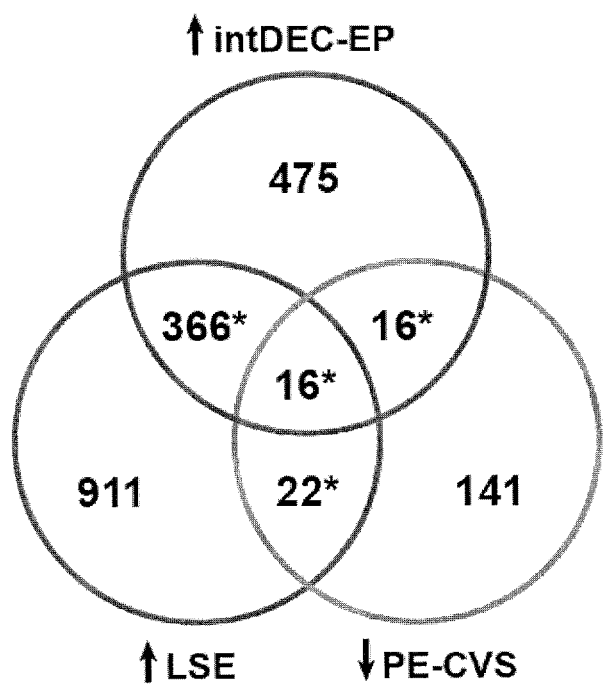

Gene expression in endometrium from women with EP showing intDEC changes was compared to gene expression in nonDEC endometrium obtained from women with EP (E-MTAB-680, (Duncan W C et al. (2011) Ibid.). The up-regulated DEG in intDEC endometrium (873 DEG) was compared to the down-regulated DEG in PE-CVS. There was a significant overlap of 32 genes between DEG up-regulated in intDEC endometrium and down-regulated in PE-CVS ($p<0.0001$; FIG. 11B, Table 11). There was also a large and significant overlap of 382 DEG increasing in LSE endometrium with DEG up-regulated in intDEC endometrium from EP. Of these, 16 DEG significantly overlapped with the DEG down-regulated in PE-CVS ($p<0.0001$; FIG. 11C; Table 12).

Figure 12A:
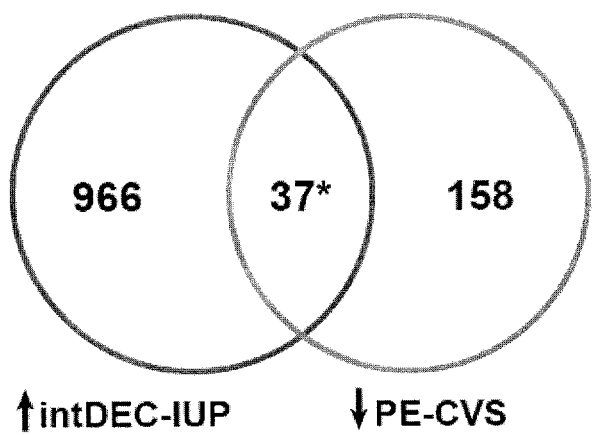
FIGS. 12A-12D are Venn Diagrams showing differentially expressed genes (DEG) down-regulated in chorionic villous samples obtained from women ~11 gestational weeks who developed preeclampsia 5-6 months later (PE-CVS; relative to CVS from women with normal pregnancy) and their overlap with DEG up-regulated in endometrium and with intermediate (intDEC) and confluent (confDEC) decidual changes from intrauterine pregnancy (IUP; relative to EP endometrium without decidual changes), but not with DEG up-regulated in cultured DEC stromal cells incubated with trophoblast conditioned médium (TrCM).
Figure 12B:
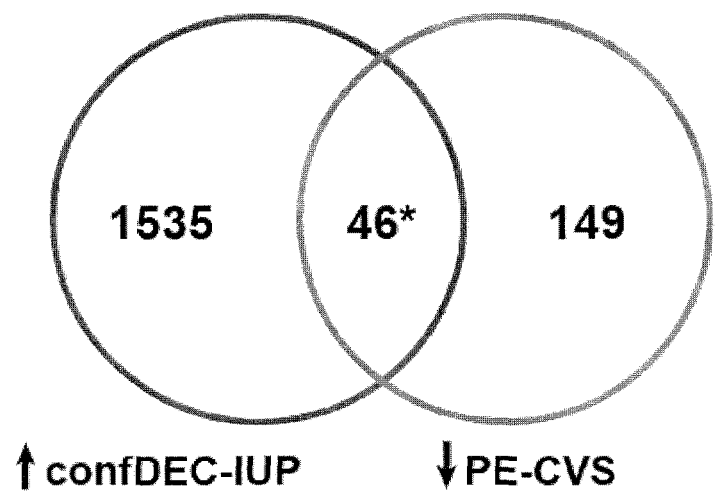

DEG down-regulated in PE-CVS and up-regulated in int- and confDEC-IUP endometrium overlap significantly: gene expression in endometrium from women with IUP (both int- and confDEC) was first compared to gene expression in nonDEC endometrium obtained from women with EP (E-MTAB-680 (Duncan W C et al. (2011) Ibid.)). The up-regulated DEG in int- (1007 DEG) and conDEC (1581 DEG) endometrium were compared to the 195 down-regulated DEG in PE-CVS. Thirty-seven and 46 DEG up-regulated in int- and conDEC endometrium, respectively, overlapped with DEG down-regulated in PE-CVS (both $p<0.0001$; FIGS. 12A and 12B; Tables 13 and 14, respectively).

Comparison of DEG down-regulated in PE-CVS with DEG up-regulated in intDEC-IUP and -EP endometrium: because IUP endometrium was influenced by local trophoblast (Tr) but EP endometrium was not (as verified by immunohistochemistry for cytokeratin), the potential Tr contribution to the overlap of DEG down-regulated in PE-CVS and up-regulated in intDEC endometrium was estimated. There was large overlap of 689 DEG up-regulated in intDEC endometrium from EP and IUP, compared to nonDEC endometrium from EP ($p<0.0001$, FIG. C). As further illustrated in FIG. 12C, 30 of these 689 DEG overlapped significantly with DEG down-regulated in PE-CVS ($p<0.0001$, Table 15). The majority of overlapping DEG between those up-regulated in intDEC from IUP or EP and down-regulated in PE-CVS were the same genes (30 of 37 for intDEC-IUP and 30 of 32 for intDEC-EP).

Figure 12C:
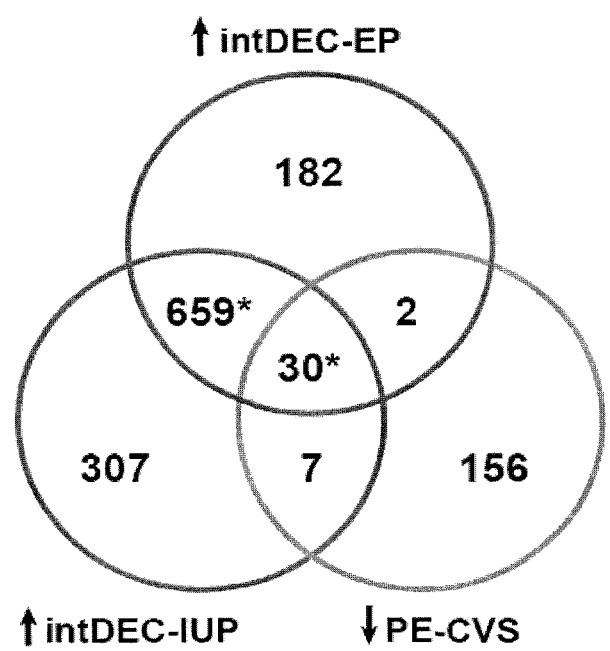
Figure 12D:
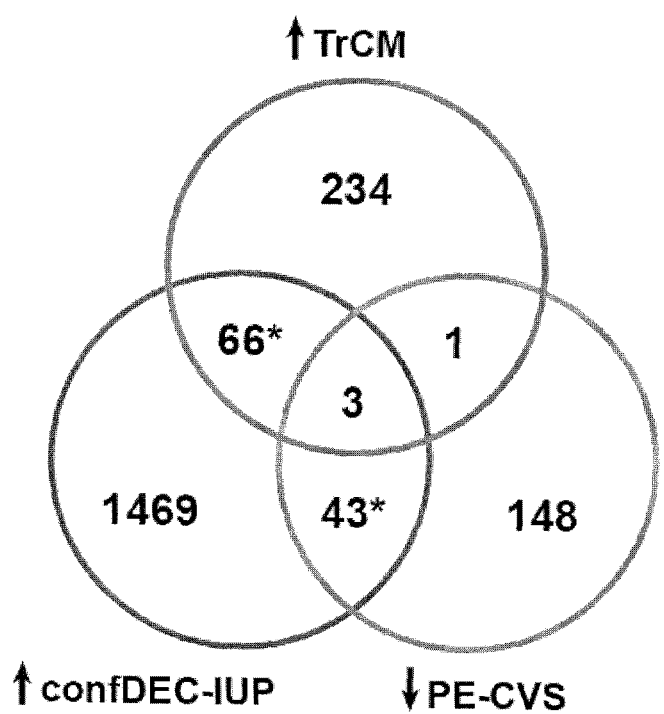

Expression of DEG down-regulated in PE-CVS was not significantly associated with genes expressed in cultured DEC endometrial cells by trophoblast conditioned medium (TrCM): DEG down-regulated in PE-CVS were compared to genes induced by TrCM in cultured endometrial cells decidualized in vitro. TrCM was obtained from cytotrophoblasts isolated from placentae between 6 and 22 weeks of gestation after elective termination and culture on Matrigel-coated substrate for 48 hours (GSE5809, (56)). DEC endometrial cell gene expression was analyzed over time (0, 3 and 12 hours of incubation with TrCM) and between treated and untreated DEC endometrial cell cultures. Selected genes were clustered by supervised weighted gene co-expression analysis, in order to identify the cluster of co-expressed genes strongly increasing expression after 12 hours of TrCM incubation. As expected, there was significant overlap between the cluster of 304 DEG increasing expression in DEC endometrial cells incubated with TrCM and DEG up-regulated in confDEC-IUP endometrium influenced by local Tr (69 DEG, $p<0.0001$; FIG. 12D). However, there was no significant intersection of endometrial genes increasing in expression after treatment with TrCM and DEG down-regulated in PE-CVS with only 4 DEG in common (FIG. 12D, $p=0.5$).

Confluence of overlapping genes: the confluence of DEG down-regulated in PE-CVS and up-regulated in LSE, intDEC-IUP and -EP, as well as confDEC-IUP endometrium was investigated. As portrayed by the Venn Diagram in FIG. 13, there were 20 down-regulated DEG in PE-CVS, which were up-regulated in LSE but not in int- or confDEC; 13 DEG down-regulated in PE-CVS and up-regulated in int- and confDEC, but not in LSE ($p<0.0001$), and 16 DEG down-regulated in PE-CVS and up-regulated in LSE, int- and confDEC endometrium ($p<0.0001$). The individual DEGs are presented in Table 16 and their mean expression values are illustrated in FIGS. 14A-14D.

Figure 14A:
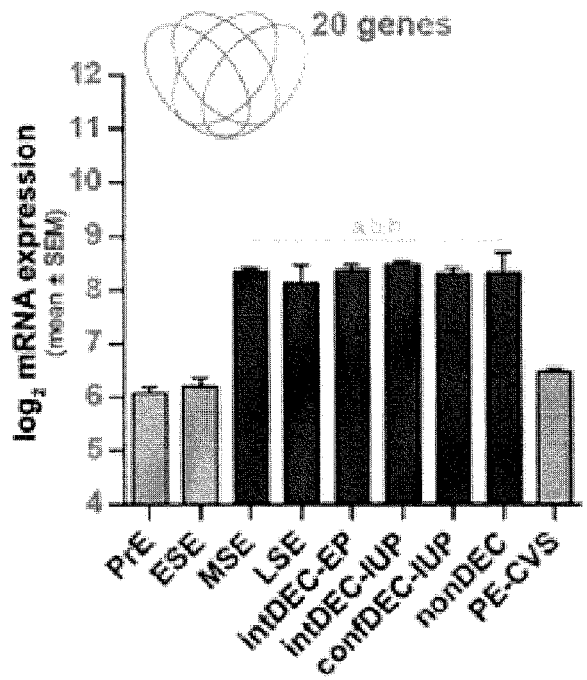
FIGS. 14A-14D illustrate average expression levels (log base 2) of differentially expressed genes (DEG) in samples obtained from endometrium at different stages of endometrial maturation and from PE-CVS.
Figure 14B:
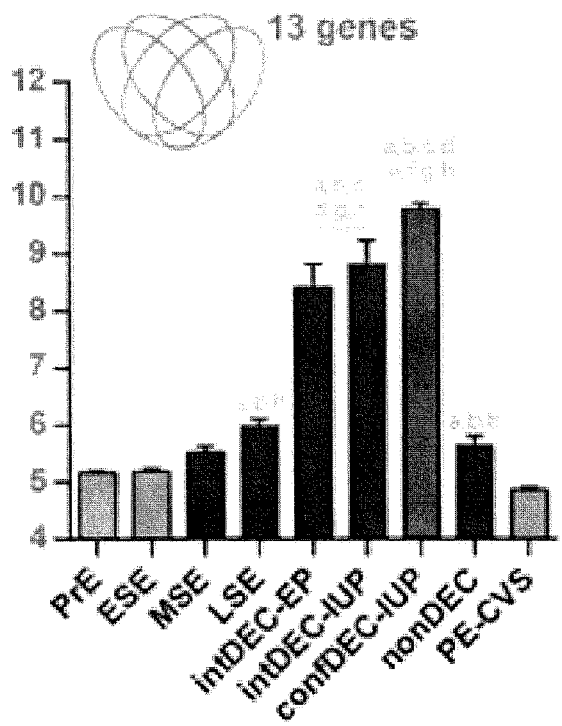
Figure 14C:
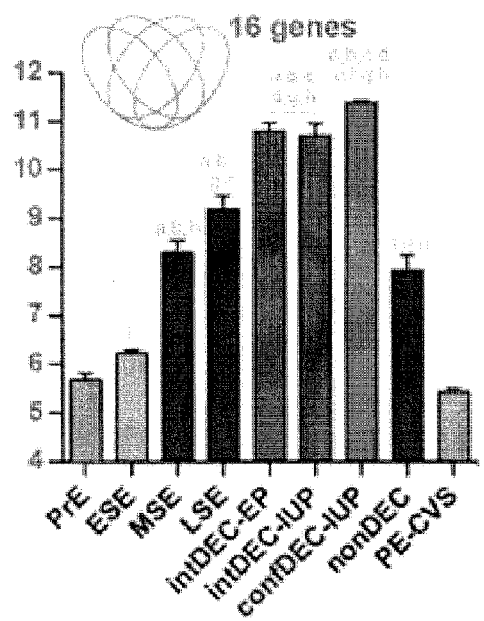
Figure 14D:
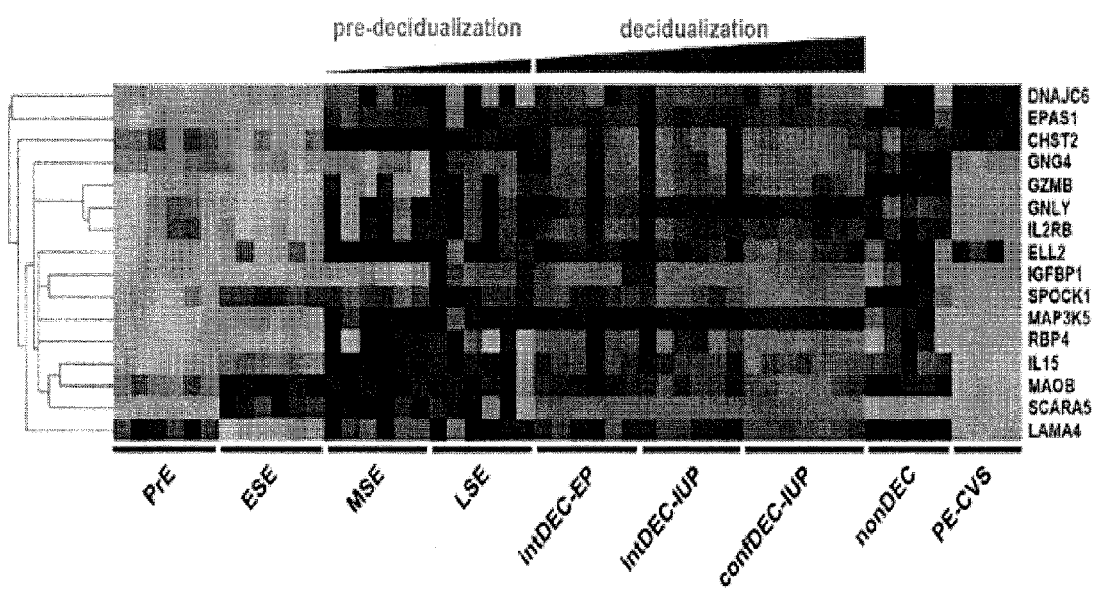

FIG. 14A depicts the log 2 mean expression values for the DEG down-regulated in PE-CVS (relative to NP-CVS) and up-regulated in LSE relative to proliferative endometrium (PrE; DEG). FIG. 14B depicts the log 2 mean expression values for the DEG down-regulated in PE-CVS (relative to NP-CVS) and up-regulated in int- and confDEC relative to nonDEC-EP (13 DEG). FIG. 14C depicts the log 2 mean expression values for the DEG down-regulated in PE-CVS (relative to NP-CVS) and up-regulated in LSE+int- and confDEC endometrium (16 DEG). The heat map shown in FIG. 14D corresponds with the bar graph in FIG. 14C.

Twenty DEG were identified as uniquely up-regulated in LSE and down-regulated in PE-CVS; therefore, their average expression did not further increase with DEC (FIG. 14A). Average gene expression of these 20 DEG was significantly less in PE-CVS than in MSE and LSE ($p<0.05$), and comparable to PrE or ESE endometrium. The 13 DEG down-regulated in PE-CVS and uniquely up-regulated in int- and confDEC endometrium, slightly increased in LSE, but mostly rose during decidualization (FIG. 14B). Average gene expression for these 13 DEG was markedly less in PE-CVS than in int- and confDEC endometrium ($p<0.05$). Finally, the 16 DEG down-regulated in PE-CVS and up-regulated in LSE, and int- and confDEC endometrium increased expression beginning in the MSE and progressively rose thereafter (FIG. 14C). In this case, average gene expression of the 16 DEG was also dramatically less in PE-CVS compared to int- and confDEC endometrium ($p<0.05$).

Figure 16A:
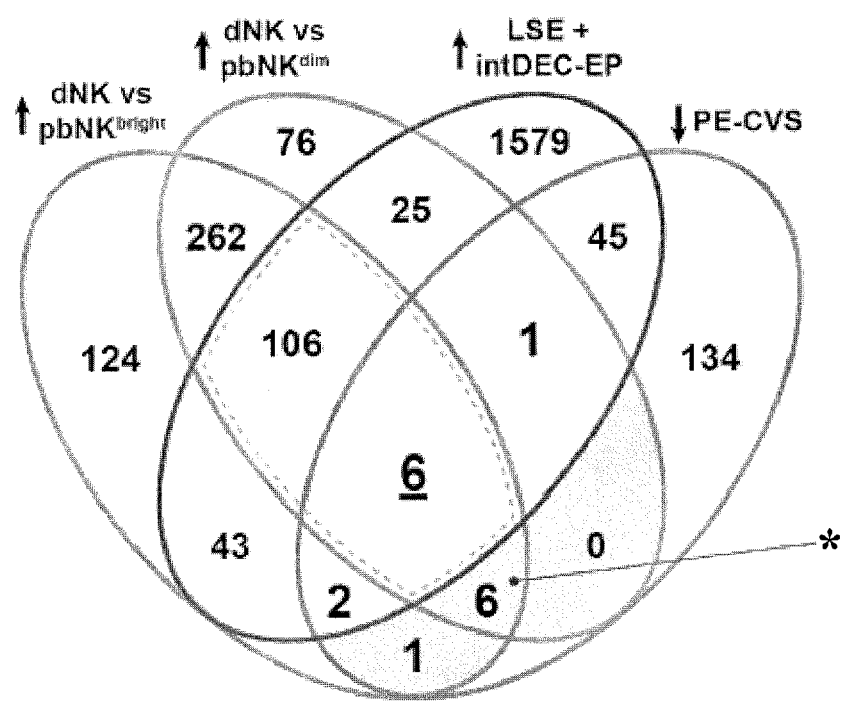
FIGS. 16A-16C illustrate the intersection of differentially expressed genes (DEG) down-regulated in chorionic villous samples obtained from women ~11 gestational weeks who developed preeclampsia 5-6 months later (PE-CVS; relative to CVS from women with normal pregnancy) and in 112 DEG up-regulated in dNK, and in LSE+intDEC-EP endometrium (highlighted by dotted line).
Figure 16B:
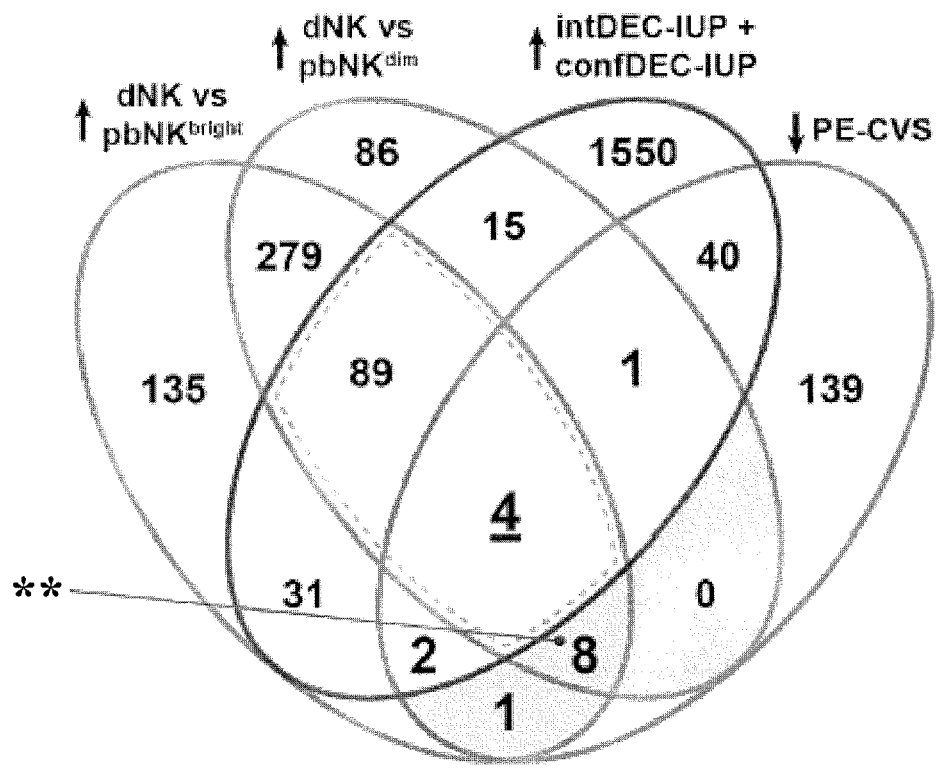

Comparison of DEG down-regulated in PE-CVS with DEG up-regulated in dNK Cells: in contrast to published gene expression of peripheral blood and endometrial (e)NK cells derived from different microarray platforms (Koopman L A et al. (2003) Ibid., and Kopcow H D et al. (2010) Human decidual NK cells from gravid uteri and NK cells from cycling endometrium are distinct NK cell subsets. *Placenta* 31:334-338), gene expression between dNK and $CD56^{dim}$ pbNK or $CD56^{bright}$ pbNK cells (Koopman L A et al. (2003) Ibid.) were compared because the same microarray platform was employed. As expected, there was a large confluence of 380 shared DEG up-regulated in dNK relative to $CD56^{dim}$ pbNK or $CD56^{bright}$ pbNK ($p<0.000001$). There was also high overlap (112 DEG) between DEG up-regulated in dNK relative to $CD56^{dim}$ pbNK or $CD56^{bright}$ pbNK, and DEG up-regulated in LSE (relative to PrE)+intDEC-EP (relative to nonDEC-EP) in the absence of local Tr influence ($p<0.00001$; FIG. 16A); and a high number of overlapping DEG (93 DEG) up-regulated in dNK relative to $CD56^{dim}$ pbNK or $CD56^{bright}$ pbNK, and intDEC-IUP+confDEC-IUP endometrium (relative to nonDEC-EP) in the presence of local Tr influence ($p<0.00001$; FIG. 16B). The majority of these 112 and 93 overlapping DEG were the same (74 DEG, $p<0.00001$, Table 17). Finally, 16 DEG up-regulated in dNK relative to $CD56^{dim}$ pbNK or $CD56^{bright}$ pbNK were down-regulated in PE-CVS (relative to NP-CVS; $p<0.0001$; FIGS. 16A and 16B).

Figure 16C:
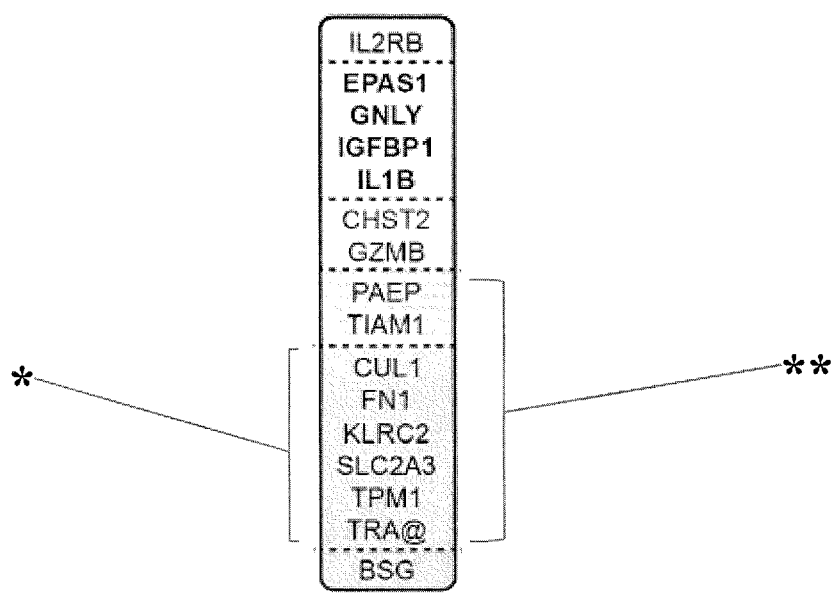

Systematic Literature Search: because the biological process of "decidualization" is not available in public bioinformatic databases for pathway analysis, a systematic and comprehensive literature search was conducted of all 195 DEG down-regulated in PE-CVS. Thirty-one were previously associated with decidua/decidualization in the literature (FIG. 16, Table 16 and Table 8). The overlap of these 31 DEG identified by literature search was evaluated against the overlapping DEG determined by systems biology approach, i.e., those down-regulated in PE-CVS and up-regulated in: LSE (38 DEG; FIG. 11A), intDEC-EP endometrium (32 DEG; FIG. 11B), intDEC-IUP endometrium (37 DEG, FIG. 12A) and confDEC-IUP endometrium (46 DEG; FIG. 12B), all together 67 unique genes (see also FIG. 13). It was found that 18 of the 31 DEG identified in the literature were in common with 67 DEG identified by systems biology (p=0.001). The majority (15, p=0.03) was up-regulated in LSE or intDEC-EP in which (local) trophoblast influence is absent.

Findings

In conducting the analysis of the original microarray dataset from PE- and NP-CVS (GSE12767, Founds S A et al. (2009) Ibid.; Example 1 above), a wide net was cast to identify DEG in PE- relative to NP-CVS (396 total; Tables 6 and 7). An impressive number of these DEG (from 70 up to 99) significantly overlapped with DEG associated with the various stages of endometrial maturation before and after conception. Moreover, at least 70% of the overlapping DEG down- or up-regulated in PE-CVS were changed in the opposite direction in the other data sets dealing with normal endometrial maturation. These findings suggest impairment of preDEC and DEC in the women who developed PE.

Analysis was then performed on DEG down-regulated in PE-CVS that were up-regulated during the biological process of (pre)decidualization. Of the 396 total DEG, 195 were down-regulated in PE- relative to NP-CVS. A cluster of 1315 co-expressed genes was found to be up-regulated during the process of endometrial maturation in the menstrual cycle culminating with the LS phase (GSE4888 and GSE6364). There was significant overlap of 38 DEG between the PE-CVS and LSE datasets (FIG. 11A). Microarray analysis of DEC in early pregnancy (E-MTAB-680) revealed 873 up-regulated genes in intDEC endometrium from ectopic pregnancy relative to nonDEC-EP endometrium. There was significant overlap of 32 DEG between those up-regulated in intDEC-EP endometrium and down-regulated in PE-CVS (FIG. 11B). Finally, the confluence of all 3 datasets yielded 16 DEG in common (FIG. 11C).

Remarkably, 54 of the 195 DEG down-regulated in PE-CVS were up-regulated during LS or intDEC endometrium from EP. Taken together, these results bolster the notion that there is impairment of endometrial maturation in the LS phase and during early pregnancy in the women destined to develop PE. Included among the genes which expression failed to increase in decidua of CVS from the women who developed PE are those classically associated with the biological process of decidualization in the literature including IGFBP-1, PAEP or glycodelin, and PRL (Tables 10-12). The results also implicate a primary defect in preDEC and DEC rather than Tr, because Tr are lacking altogether in the LS phase and local Tr influence was absent in intDEC-EP endometrium. Another, albeit less plausible explanation is that after conception defective Tr reversed preDEC in the LS phase and inhibited DEC after conception in the women who developed PE.

Further inspection of the microarray analyses from decidualization in early pregnancy revealed >1000 genes each up-regulated in int- and confDEC endometrium from intrauterine pregnancy compared to nonDEC endometrium from EP. Thirty-seven and 46 of these up-regulated DEG, respectively, overlapped significantly with DEG down-regulated in PE-CVS (FIGS. 12A and 12B, and Tables 13 and 14). There was also a large confluence of 689 DEG up-regulated in intDEC-IUP and intDEC-EP endometrium (matched for the degree of DEC). Although this degree of overlap was substantial and highly significant, it was by no means a complete overlap most likely explained by the presence of local Tr influence in the intDEC-IUP. Of note, the vast majority of DEG up-regulated in intDEC-EP and down-regulated in PE-CVS (32 DEG), and those up-regulated in intDEC-IUP and down-regulated in PE-CVS (37 DEG) were themselves overlapping (30 DEG; FIG. 12C and Table 15). These observations suggest that there was little if any contribution of Tr gene expression per se to the overlap of DEG down-regulated in PE-CVS and up-regulated in intDEC-IUP and -EP, or of Tr influence on DEC stromal, epithelial or immune cells either through cell-to-cell contact or paracrine interactions, because the vast majority of DEG down-regulated in PE-CVS were up-regulated in intDEC regardless of the presence (IUP) or absence (EP) of local Tr influence. A caveat is that the comparison of these datasets does not take into account a potential role for (circulating) endocrine factors secreted by Tr, which may not be the same for EP and IUP.

To further scrutinize the potential contribution of Tr to the impaired DEC of PE-CVS, DEG down-regulated in PE-CVS was compared with DEG up-regulated in cultured decidualized endometrial stromal cells after incubation with trophoblast conditioned medium (TrCM; GSE5809). Despite the significant overlap between DEG up-regulated in DEC endometrial stromal cells exposed to TrCM and in confDEC-IUP endometrium (69 DEG; FIG. 12D), there were virtually no DEG in common between those up-regulated in DEC endometrial stromal cells treated with TrCM (304 DEG) and down-regulated in PE-CVS (195 DEG), the overlap being a non-significant 4 genes (FIG. 12D). This finding reinforces the idea that there was minimal Tr contribution to the overlap observed between DEG down-regulated in PE-CVS and DEG up-regulated in either int- or confDEC-IUP endometrium, which is consistent with the concept that there may have been a primary defect of endometrial maturation in the women destined to develop PE.

The confluence of DEG down-regulated in PE-CVS and up-regulated in LSE, intDEC-IUP and -EP, as well as confDEC-IUP endometrium was examined (i.e., intersection of all 4 data sets; FIG. 3 and Table 16). Mean expression of the 20 DEG down-regulated in PE-CVS and uniquely up-regulated in secretory relative to PrE was significantly increased in mid-secretory endometrium (MSE), maintained in LSE, but not further increased during DEC (i.e., after implantation; FIG. 14A). Of note, the mean expression for these 20 DEG was significantly lower in PE-CVS compared to MSE and LSE by ~5-fold, and comparable to PrE and early secretory endometrium. Taken together, this analysis suggests that impairment of endometrial maturation in the women destined to develop PE may actually have begun before pregnancy in the secretory phase.

Mean expression of the 13 DEG down-regulated in PE-CVS and up-regulated in intDEC-EP and -IUP and in confDEC-IUP, but not LSE is shown in FIG. 14B. Examination of the mean expression relative to PrE revealed a significant increase in intDEC-EP and -IUP with a further rise in confDEC-IUP endometrium (FIG. 14B). The mean expression level in PE-CVS was markedly reduced relative to int- and confDEC by ~15-fold. These results suggest that, in addition to a defect in preDEC as described above there was also impairment of DEC after implantation in the women who developed PE.

Finally, a core set of 16 DEG was down-regulated in PE-CVS and up-regulated in LSE, intDEC-EP and -IUP, and confDEC-IUP endometrium (FIG. 14C). The average level of expression of these 16 genes relative to PrE increased progressively beginning with MSE and peaking in conf-DEC-IUP endometrium. Mean gene expression for PE-CVS was considerably lower than MSE, LSE, int- and confDEC, the latter by ~50-fold. On balance, these data present a composite picture of FIGS. 14A and 14B underscoring the notion that both preDEC and DEC were compromised in the women who developed PE.

Figure 15:
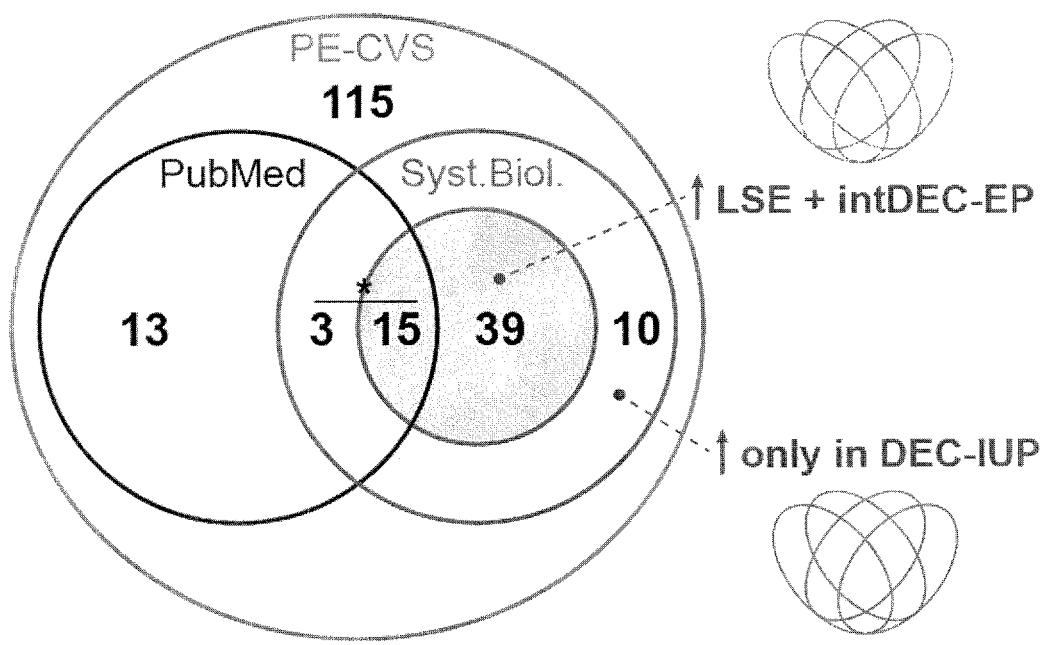
FIG. 15 is a Venn Diagram illustrating the intersection of differentially expressed genes (DEG) down-regulated in chorionic villous samples obtained from women ~11 gestational weeks who developed preeclampsia 5-6 months later (PE-CVS; relative to CVS from women with normal pregnancy) and DEG up-regulated in: (A) late secretory endometrium (LSE, relative to proliferative endometrium)+intermediate DEC endometrium from ectopic pregnancy (intDEC-EP, relative to ectopic pregnancy endometrium without decidual changes) and decidual Natural Killer cells (dNK, relative to peripheral blood $CD56^{dim}$ NK or $CD56^{bright}$ NK cells); (B) endometrium with intermediate+confluent decidual changes from intrauterine pregnancy (intDEC and confDEC-IUP) and dNK.

Because DEG known to be involved in dNK function emerged from the aforementioned analyses (e.g., IL-15, IL2RB, etc., see Table 16), the overlap of DEG up-regulated in isolated dNK (relative to $CD56^{dim}$ pbNK or $CD56^{bright}$ pbNK) cells and down-regulated in PE-CVS (FIG. 15) was explored. Despite lacking the corresponding eNK cell match (at least for LSE), it was discovered that a large confluence of 112 DEG up-regulated in isolated dNK and in LSE+ intDEC-EP with local Tr absent (FIG. 15A). These common DEG may be expressed by dNK alone or co-expressed with other cell-types in the LSE including other immune, DEC stromal, epithelial and glandular cells. When up-regulated DEG in dNK were compared to those up-regulated in intDEC+confDEC-IUP with local Tr present, the overlapping genes (93 DEG, FIG. 15B) were mostly the same as in LSE+in DEC-EP (74 DEG, Table 17). Taken together, these results suggest minimal contribution of Tr gene expression per se, or Tr contact with or paracrine effects on decidual cells to the intersection of DEG. Finally, in addition to impaired DEC (vide supra), the women destined to develop PE were also likely to have deficient dNK cell number and/or function, because 16 DEG up-regulated in dNK were down-regulated in PE-CVS (FIGS. 15A and 15B).

In addition to the evidence provided by bioinformatics approaches linking the DEG down-regulated in PE-CVS to impaired endometrial maturation, a different tack was taken to marshal further evidence associating these down-regulated DEG to inadequate preDEC and DEC. Because preDEC and DEC biological pathways are not represented in public bioinformatic databases, a systematic and comprehensive literature search of all 195 DEG down-regulated in PE-CVS (FIG. 16 and Table 8) was conducted. It was discovered that 31 of the 195 DEG had been previously linked to decidua or decidualization in the literature. There was a significant overlap of 18 genes with the decidualization genes identified by bioinformatics approach. Of these, only 3 were exclusively up-regulated during DEC in intra-uterine pregnancies, the remaining 15 genes were also up-regulated during the process of preDEC or DEC in the absence of Tr (Table 16, FIG. 16 and Table 8). Thus, the systematic literature search further strengthens the argument that endometrial maturation was impaired in the women destined to develop PE.

Figure 17:
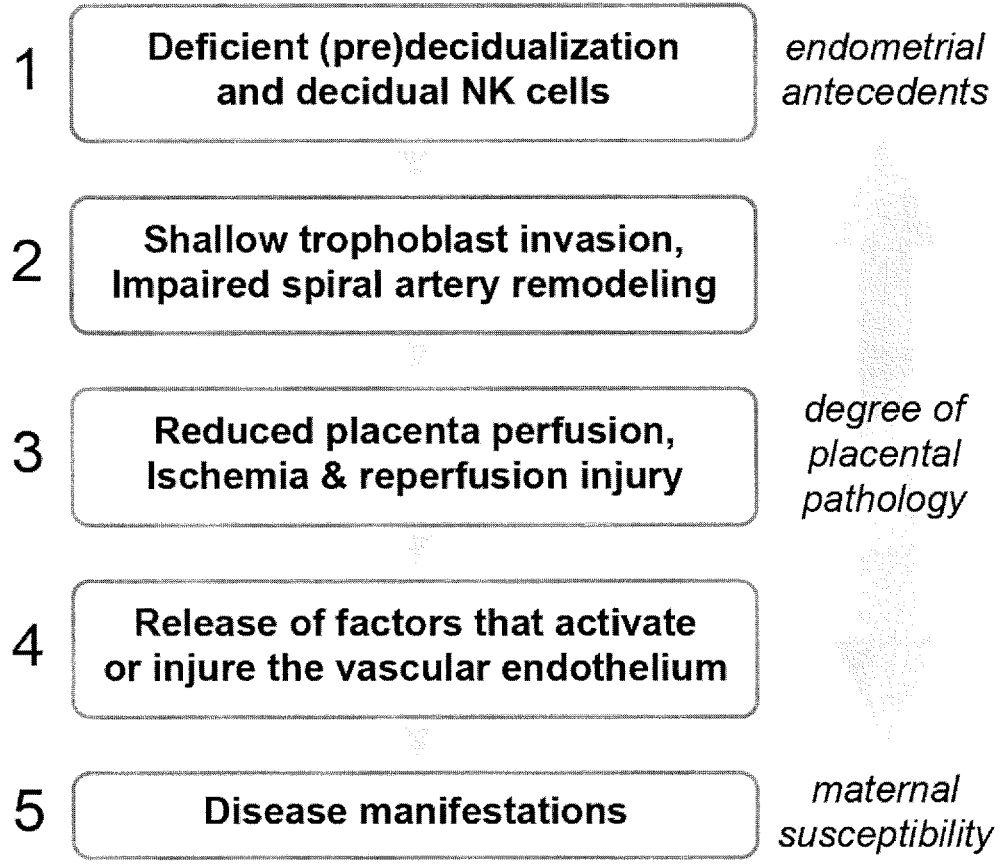
FIG. 17 is an illustration of the five-stages of preeclampsia. Based on a systems biology approach, the findings of Example 2 described herein raised the possibility that impaired endometrial maturation and deficient decidual NK cell number and/or function in the secretory phase (pre-decidualization) and during early pregnancy (decidualization) precede the development of preeclampsia. As pre-decidualization, decidualization and associated decidual NK cell function are emerging as important players in the regulation of trophoblast invasion, and hence, spiral artery remodeling, perturbation of these biological processes may contribute to the etiology of preeclampsia.

In summary, substantial evidence is provided for deficient DEC in the LS phase and during early pregnancy in women destined to develop PE as illustrated in FIG. 17. This conclusion is based on a systems biology approach, which was employed to evaluate microarray analysis of $1^{st}$ trimester placentas from women who developed late onset, severe PE or experienced a normal pregnancy in the context of other microarray studies in the public domain related to normal maturation of endometrium and of dNK cells. Remarkably, one-third of the DEG down-regulated in PE-relative to NP-CVS were up-regulated during the biological process of endometrial maturation, and a number of these were uniquely up-regulated in dNK cells. Moreover, the analysis performed above further suggests that inadequate endometrial maturation may be a primary event, because the majority of these DEG were up-regulated in LSE or DEC endometrium from ectopic pregnancy in the absence of local Tr influence. The latter conclusion is reinforced by the finding that an insignificant few of the DEG down-regulated in PE-CVS overlapped with DEG up-regulated in decidualized stromal cells in culture exposed to TrCM. The subject study provides evidence supporting a link between deficient endometrial maturation and the development of preeclampsia.

In accordance with the subject application, supplemental hormonal support with relaxin, congener or mimetic during the LS phase, and in certain instances into early pregnancy, will improve endometrial maturation, thereby improving the uterine environment for Tr invasion and spiral artery remodeling to facilitate normal placentation, and thus treat and/or reduce the likelihood of development of placental syndromes, including PE.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

TABLE 1

Gene Expression associated with Decidualization
(Fold Change Data for CVS Microarray: PE vs. NP)

| Gene Symbol | Probe ID* | Fold Change | Condition PE Group | Target Description |
| --- | --- | --- | --- | --- |
| ALDH1L2 | 207016_s_at | −7.8 | Underexpressed | gb:AB015228.1 /DB_XREF=gi:3970845 /GEN=RALDH2 /FEA=FLmRNA /CNT=10 /TID=Hs.95197.0 /TIER=FL /STK=0 /UG=Hs.95197 /LL=8854 /DEF=*Homo sapiens* mRNA for RALDH2-T, complete cds. /PROD=RALDH2-T /FL=gb:AB015228.1 gb:AB015227.1 gb:AB015226.1 gb:NM_003888.1 |

TABLE 1-continued

Gene Expression associated with Decidualization
(Fold Change Data for CVS Microarray: PE vs. NP)

| Gene Symbol | Probe ID* | Fold Change | Condition PE Group | Target Description |
|---|---|---|---|---|
| RORB | 231040_at | −13.2 | Underexpressed | gb:AW512988 /DB_XREF=gi:7151066 /DB_XREF=xt76b02.x1 /CLONE=IMAGE:2792331 /FEA=EST /CNT=9 /TID=Hs.184780.0 /TIER=Stack /STK=9 /UG=Hs.184780 /UG_TITLE=ESTs |
| ACOT8 | 236514_at | 2.1 | Overexpressed | gb:AI885067 /DB_XREF=gi:5590231 /DB_XREF=wl89c05.x1 /CLONE=IMAGE:2432072 /FEA=EST /CNT=7 /TID=Hs.6511.0 /TIER=ConsEnd /STK=6 /UG=Hs.6511 /UG_TITLE=ESTs |
| EPAS1 | 242868_at | −15.3 | Underexpressed | gb:T70087 /DB_XREF=gi:681235 /DB_XREF=yc17g11.s1 /CLONE=IMAGE:80996 /FEA=EST /CNT=7 /TID=Hs.307559.0 /TIER=ConsEnd /STK=1 /UG=Hs.307559 /UG_TITLE=ESTs |
| DLGAP1 | 1568736_s_at | −4.4 | Underexpressed | gb:BC030096.1 /DB_XREF=gi:22535265 /TID=Hs2.371203.1 /CNT=5 /FEA=mRNA /TIER=ConsEnd /STK=2 /UG=Hs.371203 /UG_TITLE=*Homo sapiens*, clone IMAGE:4795078, mRNA /DEF=*Homo sapiens*, clone IMAGE:4795078, mRNA. (All probes match over all sequences) |
| SPOCK1 | 202363_at | −5.5 | Underexpressed | gb:AF231124.1 /DB_XREF=gi:7248844 /FEA=FLmRNA /CNT=190 /TID=Hs.93029.0 /TIER=FL+Stack /STK=68 /UG=Hs.93029 /LL=6695 /UG_GENE=SPOCK /DEF=*Homo sapiens* testican-1 mRNA, complete cds. /PROD=testican-1 /FL=gb:NM_004598.1 gb:AF231124.1 |
| MAOB | 204041_at | −2.7 | Underexpressed | gb:NM_000898.1 /DB_XREF=gi:4505092 /GEN=MAOB /FEA=FLmRNA /CNT=79 /TID=Hs.82163.0 /TIER=FL+Stack /STK=39 /UG=Hs.82163 /LL=4129 /DEF=*Homo sapiens* monoamine oxidase B (MAOB), nuclear gene encoding mitochondrial protein, mRNA. /PROD=monoamine oxidase B /FL=gb:NM_000898.1 gb:M69177.1 |
| GZMB | 210164_at | −2.7 | Underexpressed | gb:J03189.1 /DB_XREF=gi:338010 /FEA=FLmRNA /CNT=28 /TID=Hs.1051.1 /TIER=FL+Stack /STK=11 /UG=Hs.1051 /LL=3002 /UG_GENE=GZMB /UG_TITLE=granzyme B (granzyme 2, cytotoxic T-lymphocyte-associated serine esterase 1) /DEF=Human proteolytic serine esterase-like protein (SECT) gene, complete cds. /FL=gb:M17016.1 gb:J03189.1 gb:NM_004131.2 gb:J04071.1 |
| IL2RB | 205291_at | −2.8 | Underexpressed | gb:NM_000878.1 /DB_XREF=gi:4504664 /GEN=IL2RB /FEA=FLmRNA /CNT=45 /TID=Hs.75596.0 /TIER=FL+Stack /STK=26 /UG=Hs.75596 /LL=3560 /DEF=*Homo sapiens* interleukin 2 receptor, beta (IL2RB), mRNA. /PROD=interleukin 2 receptor, beta /FL=gb:NM_000878.1 gb:M26062.1 |
| GNLY | 205495_s_at | −23.5 | Underexpressed | gb:NM_006433.2 /DB_XREF=gi:7108343 /GEN=GNLY /FEA=FLmRNA /CNT=32 /TID=Hs.105806.1 /TIER=FL+Stack /STK=18 /UG=Hs.105806 /LL=10578 /DEF=*Homo sapiens* granulysin (GNLY), transcript variant NKG5, |

TABLE 1-continued

Gene Expression associated with Decidualization
(Fold Change Data for CVS Microarray: PE vs. NP)

| Gene Symbol | Probe ID* | Fold Change | Condition PE Group | Target Description |
|---|---|---|---|---|
| NOG | 231798_at | −5.3 | Underexpressed | mRNA. /PROD=granulysin, isoform NKG5 /FL=gb:NM_006433.2 gb:AL575177 /DB_XREF=gi:12936088 /DB_XREF=AL575177 /CLONE=CS0DI063YJ07 (3 prime) /FEA=FLmRNA /CNT=7 /TID=Hs.248201.0 /TIER=ConsEnd /STK=1 /UG=Hs.248201 /LL=9241 /UG_GENE=NOG /UG_TITLE=noggin /FL=gb:NM_005450.1 |
| TRA@ | 217143_s_at | −4.9 | 217143_s_at | gb:X06557.1 /DB_XREF=gi:37003 /FEA=mRNA /CNT=2 /TID=Hs.2014.2 /TIER=ConsEnd /STK=0 /UG=Hs.2014 /LL=6964 /UG_GENE=TRD@ /UG_TITLE=T cell receptor delta locus /DEF=Human mRNA for TCR-delta chain. |
| MUC15 | 227238_at | −8 | Underexpressed | gb:W93847 /DB_XREF=gi:1422970 /DB_XREF=zd97a07.s1 /CLONE=IMAGE:357396 /FEA=mRNA /CNT=89 /TID=Hs.24139.0 /TIER=Stack /STK=21 /UG=Hs.24139 /UG_TITLE=*Homo sapiens* cDNA: FLJ23137 fis, clone LNG08842 |
| KLRC2 | 206785_s_at | −2.9 | Underexpressed | gb:NM_002260.2 /DB_XREF=gi:7108353 /GEN=KLRC2 /FEA=FLmRNA /CNT=12 /TID=Hs.177605.0 /TIER=FL /STK=1 /UG=Hs.177605 /LL=3822 /DEF=*Homo sapiens* killer cell lectin-like receptor subfamily C, member 2 (KLRC2), mRNA. /PROD=killer cell lectin-like receptor subfamily C,member 2 /FL=gb:NM_002260.2 gb:AF260134.1 |
| IL15 | 205992_s_at | −2.8 | Underexpressed | gb:NM_000585.1 /DB_XREF=gi:10835152 /GEN=IL15 /FEA=FLmRNA /CNT=33 /TID=Hs.168132.0 /TIER=FL /STK=0 /UG=Hs.168132 /LL=3600 /DEF=*Homo sapiens* interleukin 15 (IL15), mRNA. /PROD=interleukin 15 /FL=gb:NM_000585.1 gb:U14407.1 |
| CHRDL1 | 209763_at | −7.3 | Underexpressed | gb:AL049176 /DB_XREF=gi:4808226 /FEA=FLmRNA /CNT=84 /TID=Hs.82223.0 /TIER=Stack /STK=46 /UG=Hs.82223 /LL=57803 /UG_GENE=LOC57803 /UG_TITLE=chordin-like /DEF=Human DNA sequence from clone 141H5 on chromosome Xq22.1-23. Contains parts of a novel Chordin LIKE protein with von Willebrand factor type C domains. Contains ESTs, STSs and GSSs /FL=gb:BC002909.1 |
| PRL | 205445_at | −7.9 | Underexpressed | gb:NM_000948.1 /DB_XREF=gi:4506104 /GEN=PRL /FEA=FLmRNA /CNT=352 /TID=Hs.1905.0 /TIER=FL+Stack /STK=19 /UG=Hs.1905 /LL=5617 /DEF=*Homo sapiens* prolactin (PRL), mRNA. /PROD=prolactin /FL=gb:NM_000948.1 |
| SCARA5 | 229839_at | −8.3 | Underexpressed | gb:AI799784 /DB_XREF=gi:5365256 /DB_XREF=wc43b08.x1 /CLONE=IMAGE:2321367 /FEA=EST /CNT=10 /TID=Hs.49696.0 /TIER=Stack /STK=9 /UG=Hs.49696 /UG_TITLE=ESTs |
| CHST6 | 223786_at | −2.2 | Underexpressed | gb:AF280086.1 /DB_XREF=gi:12060803 |

TABLE 1-continued

Gene Expression associated with Decidualization
(Fold Change Data for CVS Microarray: PE vs. NP)

| Gene Symbol | Probe ID* | Fold Change | Condition PE Group | Target Description |
|---|---|---|---|---|
| | | | | /GEN=GST4beta /FEA=FLmRNA /CNT=9 /TID=Hs.157439.1 /TIER=FL /STK=0 /UG=Hs.157439 /LL=4166 /DEF=*Homo sapiens* N-acetylglucosamine 6-O-sulfotransferase GST-4beta mRNA, complete cds. /PROD=N-acetylglucosamine 6-O-sulfotransferaseGST-4beta /FL=gb:AF280086.1 |
| NTN1 | 227816_at | −3.6 | Underexpressed | gb:BF591483 /DB_XREF=gi:11683807 /DB_XREF=nab98c06.x1 /CLONE=IMAGE:3275890 /FEA=EST /CNT=23 /TID=Hs.96917.0 /TIER=Stack /STK=15 /UG=Hs.96917 /UG_TITLE=ESTs |
| BICD1 | 204741_at | 2.2 | Overexpressed | gb:NM_001714.1 /DB_XREF=gi:4502408 /GEN=BICD1 /FEA=FLmRNA /CNT=47 /TID=Hs.164975.0 /TIER=FL+Stack /STK=10 /UG=Hs.164975 /LL=636 /DEF=*Homo sapiens* Bicaudal D (*Drosophila*) homolog 1 (BICD1), mRNA. /PROD=Bicaudal D (*Drosophila*) homolog 1 /FL=gb:U90028.1 gb:NM_001714.1 |
| ADCYAP1R1 | 221286_s_at | 3.1 | Overexpressed | gb:NM_016459.1 /DB_XREF=gi:7706002 /GEN=LOC51237 /FEA=FLmRNA /CNT=10 /TID=Hs.122492.1 /TIER=FL /STK=1 /UG=Hs.122492 /LL=51237 /DEF=*Homo sapiens* hypothetical protein (LOC51237), mRNA. /PROD=hypothetical protein /FL=gb:NM_016459.1 |
| CPM | 235019_at | −2.1 | Underexpressed | gb:BE878495 /DB_XREF=gi:10327271 /DB_XREF=601492515F1 /CLONE=IMAGE:3894722 /FEA=EST /CNT=32 /TID=Hs.267158.0 /TIER=ConsEnd /STK=0 /UG=Hs.267158 /UG_TITLE=ESTs |
| DPYSL4 | 205493_s_at | 2 | Overexpressed | gb:NM_006426.1 /DB_XREF=gi:11321616 /GEN=DPYSL4 /FEA=FLmRNA /CNT=29 /TID=Hs.100058.0 /TIER=FL /STK=1 /UG=Hs.100058 /LL=10570 /DEF=*Homo sapiens* dihydropyrimidinase-like 4 (DPYSL4), mRNA. /PROD=dihydropyrimidinase-like 4 /FL=gb:NM_006426.1 gb:AB006713.1 |
| IL1B | 205067_at | −2.1 | Underexpressed | gb:NM_000576.1 /DB_XREF=gi:10835144 /GEN=IL1B /FEA=FLmRNA /CNT=97 /TID=Hs.126256.0 /TIER=FL+Stack /STK=15 /UG=Hs.126256 /LL=3553 /DEF=*Homo sapiens* interleukin 1, beta (IL1B), mRNA. /PROD=interleukin 1, beta /FL=gb:M15330.1 gb:M54933.1 gb:K02770.1 gb:NM_000576.1 |
| MMP12 | 204580_at | −17.2 | Underexpressed | gb:NM_002426.1 /DB_XREF=gi:4505206 /GEN=MMP12 /FEA=FLmRNA /CNT=72 /TID=Hs.1695.0 /TIER=FL+Stack /STK=18 /UG=Hs.1695 /LL=4321 /DEF=*Homo sapiens* matrix metalloproteinase 12 (macrophage elastase) (MMP12), mRNA. /PROD=matrix metalloproteinase 12 preproprotein /FL=gb:L23808.1 gb:NM_002426.1 |
| BDKRB2 | 205870_at | −2.7 | Underexpressed | gb:NM_000623.1 /DB_XREF=gi:4557358 /GEN=BDKRB2 /FEA=FLmRNA /CNT=34 /TID=Hs.250882.0 |

TABLE 1-continued

Gene Expression associated with Decidualization
(Fold Change Data for CVS Microarray: PE vs. NP)

| Gene Symbol | Probe ID* | Fold Change | Condition PE Group | Target Description |
|---|---|---|---|---|
| | | | | /TIER=FL+Stack /STK=17 /UG=Hs.250882 /LL=624 /DEF=*Homo sapiens* bradykinin receptor B2 (BDKRB2), mRNA. /PROD=bradykinin receptor B2 /FL=gb:M88714.1 gb:NM_000623.1 |
| SLC16A6 | 230748_at | −8.4 | Underexpressed | gb:AI873273 /DB_XREF=gi:5547322 /DB_XREF=wf41c12.x1 /CLONE=IMAGE:2358166 /FEA=EST /CNT=20 /TID=Hs.42645.0 /TIER=Stack /STK=10 /UG=Hs.42645 /UG_TITLE=ESTs |
| COL5A1 | 213818_x_at | 2.1 | Overexpressed | gb:AI862325 /DB_XREF=gi:5526432 /DB_XREF=tw71h04.x1 /CLONE=IMAGE:2265175 /FEA=EST /CNT=23 /TID=Hs.146428.3 /TIER=Stack /STK=19 /UG=Hs.146428 /LL=1289 /UG_GENE=COL5A1 /UG_TITLE=collagen, type V, alpha 1 |
| FN1 | 214702_at | −8.2 | Underexpressed | gb:AJ276395.1 /DB_XREF=gi:12053816 /GEN=FN /FEA=mRNA /CNT=52 /TID=Hs.321592.0 /TIER=ConsEnd /STK=4 /UG=Hs.321592 /DEF=*Homo sapiens* mRNA for MSF-FN70 (FN gene). /PROD=migration stimulation factor FN70 |
| PP14 | 206859_s_at | −15.6 | Underexpressed | gb:NM_002571.1 /DB_XREF=gi:4505582 /GEN=PAEP /FEA=FLmRNA /CNT=18 /TID=Hs.82269.0 /TIER=FL+Stack /STK=13 /UG=Hs.82269 /LL=5047 /DEF=*Homo sapiens* progestagen-associated endometrial protein (placental protein 14, pregnancy-associated endometrial alpha-2-globulin, alpha uterine protein) (PAEP), mRNA. /PROD=progestagen-associated endometrial protein(placental protein 14, pregnancy-associated endometrialalpha-2-globulin, alpha uterine protein) /FL=gb:NM_002571.1 gb:J04129.1 |
| FOSB | 202768_at | 2.3 | Overexpressed | gb:NM_006732.1 /DB_XREF=gi:5803016 /GEN=FOSB /FEA=FLmRNA /CNT=167 /TID=Hs.75678.0 /TIER=FL+Stack /STK=67 /UG=Hs.75678 /LL=2354 /DEF=*Homo sapiens* FBJ murine osteosarcoma viral oncogene homolog B (FOSB), mRNA. /PROD=FBJ murine osteosarcoma viral oncogene homologB /FL=gb:NM_006732.1 gb:L49169.1 |
| FSTL3 | 203592_s_at | −10.1 | Underexpressed | gb:NM_005860.1 /DB_XREF=gi:5031700 /GEN=FSTL3 /FEA=FLmRNA /CNT=129 /TID=Hs.25348.0 /TIER=FL+Stack /STK=33 /UG=Hs.25348 /LL=10272 /DEF=*Homo sapiens* follistatin-like 3 (secreted glycoprotein) (FSTL3), mRNA. /PROD=follistatin-like 3 glycoprotein /FL=gb:U76702.1 gb:NM_005860.1 |
| WT1 | 206067_s_at | −5.3 | Underexpressed | gb:NM_024426.1 /DB_XREF=gi:13386509 /GEN=WT1 /FEA=FLmRNA /CNT=24 /TID=Hs.1145.1 /TIER=FL+Stack /STK=11 /UG=Hs.1145 /LL=7490 /DEF=*Homo sapiens* Wilms tumor 1 (WT1), transcript variant D, mRNA. /PROD=Wilms tumor 1 isoform D /FL=gb:NM_024424.1 gb:NM_024426.1 |

TABLE 1-continued

Gene Expression associated with Decidualization
(Fold Change Data for CVS Microarray: PE vs. NP)

| Gene Symbol | Probe ID* | Fold Change | Condition PE Group | Target Description |
|---|---|---|---|---|
| IGFBP1 | 205302_at | −10.4 | Underexpressed | gb:NM_000596.1 /DB_XREF=gi:4504614 /GEN=IGFBP1 /FEA=FLmRNA /CNT=268 /TID=Hs.102122.0 /TIER=FL+Stack /STK=117 /UG=Hs.102122 /LL=3484 /DEF=*Homo sapiens* insulin-like growth factor binding protein 1 (IGFBP1), mRNA. /PROD=insulin-like growth factor binding protein 1 /FL=gb:NM_000596.1 gb:M31145.1 gb:M20841.1 |
| CFH/CFHR1 | 215388_s_at | −8.5 | Underexpressed | gb:X56210.1 /DB_XREF=gi:30132 /GEN=H 36-2 /FEA=mRNA /CNT=4 /TID=Hs.296941.0 /TIER=ConsEnd /STK=0 /UG=Hs.296941 /LL=3079 /DEF=*H.sapiens* mRNA for complement Factor H-related protein 1, clone H 36-2. /PROD=FHR-1; complement Factor H-related protein 1 |
| C3 | 217767_at | −3.3 | Underexpressed | gb:NM_000064.1 /DB_XREF=gi:4557384 /GEN=C3 /FEA=FLmRNA /CNT=473 /TID=Hs.284394.0 /TIER=FL+Stack /STK=213 /UG=Hs.284394 /LL=718 /DEF=*Homo sapiens* complement component 3 (C3), mRNA. /PROD=complement component 3 precursor /FL=gb:K02765.1 gb:NM_000064.1 |
| CR1 | 217552_x_at | 2 | Overexpressed | gb:AI432713 /DB_XREF=gi:4283899 /DB_XREF=th43e02.x1 /CLONE=IMAGE:2121050 /FEA=EST /CNT=5 /TID=Hs.241053.0 /TIER=ConsEnd /STK=4 /UG=Hs.241053 /UG_TITLE=ESTs |
| C4BPA | 205654_at | −2.7 | Underexpressed | gb:NM_000715.1 /DB_XREF=gi:4502502 /GEN=C4BPA /FEA=FLmRNA /CNT=53 /TID=Hs.1012.0 /TIER=FL+Stack /STK=22 /UG=Hs.1012 /LL=722 /DEF=*Homo sapiens* complement component 4-binding protein, alpha (C4BPA), mRNA. /PROD=complement component 4-binding protein, alpha /FL=gb:NM_000715.1 gb:M31452.1 |
| Flt-4 | 229902_at | −2.1 | Underexpressed | gb:AW083785 /DB_XREF=gi:6038937 /DB_XREF=xc35b04.x1 /CLONE=IMAGE:2586223 /FEA=EST /CNT=14 /TID=Hs.8941.0 /TIER=Stack /STK=11 /UG=Hs.8941 /UG_TITLE=ESTs |
| ITGB6 | 208084_at | −2.1 | Underexpressed | gb:NM_000888.3 /DB_XREF=gi:9966771 /GEN=ITGB6 /FEA=FLmRNA /CNT=2 /TID=Hs.123125.0 /TIER=FL /STK=0 /UG=Hs.123125 /LL=3694 /DEF=*Homo sapiens* integrin, beta 6 (ITGB6), mRNA. /PROD=integrin, beta 6 /FL=gb:NM_000888.3 gb:M35198.3 |
| HTR2B | 206638_at | −2.5 | Underexpressed | gb:NM_000867.1 /DB_XREF=gi:4504538 /GEN=HTR2B /FEA=FLmRNA /CNT=13 /TID=Hs.2507.0 /TIER=FL+Stack /STK=10 /UG=Hs.2507 /LL=3357 /DEF=*Homo sapiens* 5-hydroxytryptamine (serotonin) receptor 2B (HTR2B), mRNA. /PROD=5-hydroxytryptamine (serotonin) receptor 2B /FL=gb:NM_000867.1 |
| S100A8 | 202917_s_at | 13.2 | Overexpressed | gb:NM_002964.2 /DB_XREF=gi:9845519 /GEN=S100A8 /FEA=FLmRNA /CNT=257 /TID=Hs.100000.0 |

TABLE 1-continued

Gene Expression associated with Decidualization
(Fold Change Data for CVS Microarray: PE vs. NP)

| Gene Symbol | Probe ID* | Fold Change | Condition PE Group | Target Description |
|---|---|---|---|---|
| ERAP2 | 219759_at | −9.9 | Underexpressed | /TIER=FL+Stack /STK=93 /UG=Hs.100000 /LL=6279 /DEF=*Homo sapiens* S100 calcium-binding protein A8 (calgranulin A) (S100A8), mRNA. /PROD=S100 calcium-binding protein A8 /FL=gb:NM_002964.2 gb:NM_022350.1 /DB_XREF=gi:11641260 /GEN=LOC64167 /FEA=FLmRNA /CNT=18 /TID=Hs.280380.0 /TIER=FL /STK=0 /UG=Hs.280380 /LL=64167 /DEF=*Homo sapiens* aminopeptidase (LOC64167), mRNA. /PROD=aminopeptidase /FL=gb:AF191545.1 gb:NM_022350.1 |

*Probe ID in Affymetrix HG-U133 Plus 2.0 Genechip

TABLE 2

Gene Expression associated with Decidualization
(Duncan et al., *PLOS One.* 6(8): e23595 (2011))

| Gene Symbol | Fold Change |
|---|---|
| ALDH1L2 | 2 |
| RORB | 2.3 |
| ACOT8 | 2.3 |
| EPAS1 | 2.6 |
| DLGAP1 | 2.6 |
| SPOCK1 | 3 |
| MAOB | 3.3 |
| GZMB | 3.7 |
| IL2RB | 3.9 |
| GNLY | 5 |
| NOG | 5.6 |
| TRA@ | 6.1 |
| MUC15 | 6.4 |
| KLRC2 | 6.8 |
| IL15 | 8.9 |
| CHRDL1 | 32 |
| PRL | 47 |
| SCARA5 | 181 |
| CHST6 | −2.2 |
| NTN1 | −4.3 |
| BICD1 | −4.4 |
| ADCYAP1R1 | −5.2 |
| CPM | −5.4 |
| DPYSL4 | −5.8 |
| HTR2B | 5.1 |
| S100A8 | 8.9 |
| ERAP2 | 4.1 |

TABLE 3

Gene Expression associated with Decidualization*

| Gene Symbol | Fold Change/Condition |
|---|---|
| ALDH1L2 | ↑ (overexpressed) |
| GNLY | ↑ (overexpressed) |
| IL15 | 2.2 |
| IL1B | 4.3 |
| MMP12 | 2.4 |
| BDKRB2 | 2 |
| SLC16A6 | 4.5 |
| COL5A1 | −2.3 |
| PP14 | ↑ (overexpressed) |
| FSTL3 | ↑[11] (overexpressed) |
| WT1 | ↑[12] (overexpressed) |
| IGFBP1 | 5.9 |
| CFH/CFHR1 | 6.2 |
| C3 | ↑ (overexpressed) |
| CR1 | ↑ (overexpressed) |
| C4BPA | ↑ (overexpressed) |
| Flt-4 | ↑ (overexpressed) |
| ITGB6 | 5.5 |

*As disclosed in Hess A P et al. "Decidual stromal cell response to paracrine signals from the trophoblast: amplification of immune and angiogenic modulators." *Biol. Reprod.* 76: 102-17 (2007); Guidice L C. "Application of functional genomics to primate endometrium: insights into biological processes." *Repro. Biol. Endocrinol.* 4(Suppl I): S4 doi: 10.1186/1477-7827-4-S1-S4; Savaris R F et al. "Endometrial gene expression in early pregnancy: lessons from human ectopic pregnancy." *Repro. Sci.* 1797-816 (2008); Guidice L C et al. "Steroid and peptide regulation of insulin-like growth factor-binding proteins secreted by human endometrial stromal cells is dependent on stromal differentiation." *J. Clin. Endocrinol. Metab.* 75: 1235-41 (1992); and Popovici R M et al. "Discovery of new inducible genes in in vitro decidualized human endometrial stromal cells using microarray technology." *Endocrinol.* 141: 3510-13 (2000).

TABLE 4

Gene Expression associated with Decidualization
(Koopman L A et al. *J Exp Med.* 198: 1201-12 (2003))

| Gene Symbol | Fold Change/Condition |
|---|---|
| GZMB | 10 |
| KLRC2 | 5 |
| SLC16A6 | No change |
| PP14 | 5 |
| FOSB | 3 |
| MAX | −4 |

TABLE 5

Gene Expression associated with Decidualization
(Irwin J C et al. *Fertil Steril.* 52: 761-8 (1989))

| Gene Symbol | Fold Change/Condition |
|---|---|
| PRL | ↑ (overexpressed) |
| FN1 | ↑ (overexpressed) |

TABLE 6

Gene Expression associated with Decidualization
(Tseng L et al. *DNA and Cell Biol.* 22: 633-40 (2003))

| Gene Symbol | Fold Change/Condition |
|---|---|
| FN1 | ↑ (overexpressed) |

TABLE 7

DEG up-regulated in PE-CVS compared to NP-CVS

| Approved symbol | Approved name | HGNC ID | Location |
|---|---|---|---|
| ABL1 | c-abl oncogene 1, non-receptor tyrosine kinase | HGNC: 76 | 9q34.1 |
| ABLIM2 | actin binding LIM protein family, member 2 | HGNC: 19195 | 4p16.1 |
| ACOT8 | acyl-CoA thioesterase 8 | HGNC: 15919 | 20q13.12 |
| ACP5 | acid phosphatase 5, tartrate resistant | HGNC: 124 | 19p13.2 |
| ACSS1 | acyl-CoA synthetase short-chain family member 1 | HGNC: 16091 | 20p11.23-p11.21 |
| ADCY4 | adenylate cyclase 4 | HGNC: 235 | 14q11.2 |
| AHSG | alpha-2-HS-glycoprotein | HGNC: 349 | 3q27.3 |
| ANKRD20A1 | ankyrin repeat domain 20 family, member A1 | HGNC: 23665 | 9p12 |
| ANXA13 | annexin A13 | HGNC: 536 | 8q24.13 |
| AOAH | acyloxyacyl hydrolase (neutrophil) | HGNC: 548 | 7p14-p12 |
| AP1S2 | adaptor-related protein complex 1, sigma 2 subunit | HGNC: 560 | Xp22 |
| AP3M2 | adaptor-related protein complex 3, mu 2 subunit | HGNC: 570 | 8p11.2 |
| ARFGEF2 | ADP-ribosylation factor guanine nucleotide-exchange factor 2 (brefeldin A-inhibited) | HGNC: 15853 | 20q13.13 |
| ARL2 | ADP-ribosylation factor-like 2 | HGNC: 693 | 11q13 |
| ATP7B | ATPase, Cu++ transporting, beta polypeptide | HGNC: 870 | 13q14.3 |
| AUTS2 | autism susceptibility candidate 2 | HGNC: 14262 | 7q11.22 |
| BCL2A1 | BCL2-related protein A1 | HGNC: 991 | 15q24.3 |
| BICD1 | bicaudal D homolog 1 (*Drosophila*) | HGNC: 1049 | 12p11.2-p11.1 |
| BOLA2 | bolA family member 2 | HGNC: 29488 | 16p11.2 |
| C11orf45 | chromosome 11 open reading frame 45 | HGNC: 28584 | 11q24.3 |
| DHRS4-AS1 | DHRS4 antisense RNA 1 | HGNC: 23175 | 14q11.2 |
| C2orf44 | chromosome 2 open reading frame 44 | HGNC: 26157 | 2p23.3 |
| NOP14-AS1 | NOP14 antisense RNA 1 | HGNC: 20205 | 4p16.3 |
| NDNF | neuron-derived neurotrophic factor | HGNC: 26256 | 4q27 |
| CARD16 | caspase recruitment domain family, member 16 | HGNC: 33701 | 11q23 |
| CASK | calcium/calmodulin-dependent serine protein kinase (MAGUK family) | HGNC: 1497 | Xp11.4 |
| CCBL2 | cysteine conjugate-beta lyase 2 | HGNC: 33238 | 1p22.2 |
| CCDC159 | coiled-coil domain containing 159 | HGNC: 26996 | 19p13.2 |
| CCK | cholecystokinin | HGNC: 1569 | 3p22.1 |
| CCL3 | chemokine (C—C motif) ligand 3 | HGNC: 10627 | 17q12 |
| CD52 | CD52 molecule | HGNC: 1804 | 1p36 |
| CD58 | CD58 molecule | HGNC: 1688 | 1p13 |
| CD83 | CD83 molecule | HGNC: 1703 | 6p23 |
| CDH15 | cadherin 15, type 1, M-cadherin (myotubule) | HGNC: 1754 | 16q24.3 |
| CDH26 | cadherin 26 | HGNC: 15902 | 20q13.33 |
| CDH3 | cadherin 3, type 1, P-cadherin (placental) | HGNC: 1762 | 16q22.1 |
| CDH6 | cadherin 6, type 2, K-cadherin (fetal kidney) | HGNC: 1765 | 5p13.3 |
| CDK16 | cyclin-dependent kinase 16 | HGNC: 8749 | Xp11 |
| CENPBD1 | CENPB DNA-binding domains containing 1 | HGNC: 28272 | 16q24.3 |
| CHST15 | carbohydrate (N-acetylgalactosamine 4-sulfate 6-O) sulfotransferase 15 | HGNC: 18137 | 10q26 |
| COL5A1 | collagen, type V, alpha 1 | HGNC: 2209 | 9q34.2-q34.3 |
| COL9A3 | collagen, type IX, alpha 3 | HGNC: 2219 | 20q13.3 |
| CR1 | complement component (3b/4b) receptor 1 (Knops blood group) | HGNC: 2334 | 1q32 |
| CTAG2 | cancer/testis antigen 2 | HGNC: 2492 | Xq28 |
| CXCL9 | chemokine (C—X—C motif) ligand 9 | HGNC: 7098 | 4q21 |
| DDX3Y | DEAD (Asp-Glu-Ala-Asp) box helicase 3, Y-linked | HGNC: 2699 | Yq11 |
| DGKD | diacylglycerol kinase, delta 130 kDa | HGNC: 2851 | 2q37 |
| DHX30 | DEAH (Asp-Glu-Ala-His) box helicase 30 | HGNC: 16716 | 3p24.3-p22.1 |
| DLC1 | deleted in liver cancer 1 | HGNC: 2897 | 8p22 |
| DOK4 | docking protein 4 | HGNC: 19868 | 16q13 |
| DPYSL3 | dihydropyrimidinase-like 3 | HGNC: 3015 | 5q32 |
| DPYSL4 | dihydropyrimidinase-like 4 | HGNC: 3016 | 10q25.2-q26 |
| EGR1 | early growth response 1 | HGNC: 3238 | 5q23-q31 |
| ELOVL4 | ELOVL fatty acid elongase 4 | HGNC: 14415 | 6q14 |
| EVC2 | Ellis van Creveld syndrome 2 | HGNC: 19747 | 4p16.2-p16.1 |
| EXD2 | exonuclease 3'-5' domain containing 2 | HGNC: 20217 | 14q24.1 |
| EXOSC6 | exosome component 6 | HGNC: 19055 | 16q22.1 |
| F8A1 | coagulation factor VIII-associated 1 | HGNC: 3547 | Xq28 |
| FAM132B | family with sequence similarity 132, member B | HGNC: 26727 | 2q37.3 |
| FAM189A2 | family with sequence similarity 189, member A2 | HGNC: 24820 | 9q21.11 |

TABLE 7-continued

DEG up-regulated in PE-CVS compared to NP-CVS

| Approved symbol | Approved name | HGNC ID | Location |
|---|---|---|---|
| FAM57A | family with sequence similarity 57, member A | HGNC: 29646 | 17p13.3 |
| FAT1 | FAT atypical cadherin 1 | HGNC: 3595 | 4q35.2 |
| FIZ1 | FLT3-interacting zinc finger 1 | HGNC: 25917 | 19q13.42 |
| FJX1 | four jointed box 1 (Drosophila) | HGNC: 17166 | 11p13 |
| FKBP1A | FK506 binding protein 1A, 12 kDa | HGNC: 3711 | 20p13 |
| FLRT2 | fibronectin leucine rich transmembrane protein 2 | HGNC: 3761 | 14q24-q32 |
| FOS | FBJ murine osteosarcoma viral oncogene homolog | HGNC: 3796 | 14q24.3 |
| FOSB | FBJ murine osteosarcoma viral oncogene homolog B | HGNC: 3797 | 19q13.3 |
| FPR3 | formyl peptide receptor 3 | HGNC: 3828 | 19q13.3-q13.4 |
| FUT6 | fucosyltransferase 6 (alpha (1,3) fucosyltransferase) | HGNC: 4017 | 19p13.3 |
| FZD5 | frizzled class receptor 5 | HGNC: 4043 | 2q33.3 |
| GBP5 | guanylate binding protein 5 | HGNC: 19895 | 1p22.2 |
| GDNF | glial cell derived neurotrophic factor | HGNC: 4232 | 5p13.1-p12 |
| GPR183 | G protein-coupled receptor 183 | HGNC: 3128 | 13q32.3 |
| HBEGF | heparin-binding EGF-like growth factor | HGNC: 3059 | 5q23 |
| HCFC1 | host cell factor C1 (VP16-accessory protein) | HGNC: 4839 | Xq28 |
| HEXA | hexosaminidase A (alpha polypeptide) | HGNC: 4878 | 15q24.1 |
| HINFP | histone H4 transcription factor | HGNC: 17850 | 11q23.3 |
| HLA-DQA1 | major histocompatibility complex, class II, DQ alpha 1 | HGNC: 4942 | 6p21.3 |
| HP | haptoglobin | HGNC: 5141 | 16q22.2 |
| LGALSL | lectin, galactoside-binding-like | HGNC: 25012 | 2p14 |
| IKZF1 | IKAROS family zinc finger 1 (Ikaros) | HGNC: 13176 | 7p12.2 |
| IL18BP | interleukin 18 binding protein | HGNC: 5987 | 11q13 |
| IPCEF1 | interaction protein for cytohesin exchange factors 1 | HGNC: 21204 | 6q25.2 |
| ISG20 | interferon stimulated exonuclease gene 20 kDa | HGNC: 6130 | 15q26 |
| ISL1 | ISL LIM homeobox 1 | HGNC: 6132 | 5q11.2 |
| ITFG2 | integrin alpha FG-GAP repeat containing 2 | HGNC: 30879 | 12p13.33 |
| ITGA9 | integrin, alpha 9 | HGNC: 6145 | 3p21.3 |
| KIF22 | kinesin family member 22 | HGNC: 6391 | 16p11.2 |
| KLHL6 | kelch-like family member 6 | HGNC: 18653 | 3q27.3 |
| ERAP2 | endoplasmic reticulum aminopeptidase 2 | HGNC: 29499 | 5q15 |
| LRP1 | low density lipoprotein receptor-related protein 1 | HGNC: 6692 | 12q13.3 |
| PPP1R37 | protein phosphatase 1, regulatory subunit 37 | HGNC: 27607 | 19q13.32 |
| LRRC8D | leucine rich repeat containing 8 family, member D | HGNC: 16992 | 1p22.2 |
| LY96 | lymphocyte antigen 96 | HGNC: 17156 | 8q13.3 |
| MAGEL2 | MAGE-like 2 | HGNC: 6814 | 15q11-q12 |
| MAP1S | microtubule-associated protein 1S | HGNC: 15715 | 19p13.12 |
| MAP2K7 | mitogen-activated protein kinase kinase 7 | HGNC: 6847 | 19p13.3-p13.2 |
| MED21 | mediator complex subunit 21 | HGNC: 11473 | 12p12 |
| MED22 | mediator complex subunit 22 | HGNC: 11477 | 9q34.1 |
| MGA | MGA, MAX dimerization protein | HGNC: 14010 | 15q15 |
| MGMT | O-6-methylguanine-DNA methyltransferase | HGNC: 7059 | 10q26 |
| MIIP | migration and invasion inhibitory protein | HGNC: 25715 | 1p36.22 |
| MPPED2 | metallophosphoesterase domain containing 2 | HGNC: 1180 | 11p13 |
| MRVI1 | murine retrovirus integration site 1 homolog | HGNC: 7237 | 11p15 |
| MSR1 | macrophage scavenger receptor 1 | HGNC: 7376 | 8p22 |
| MTRR | 5-methyltetrahydrofolate-homocysteine methyltransferase reductase | HGNC: 7473 | 5p15.31 |
| MYL9 | myosin, light chain 9, regulatory | HGNC: 15754 | 20q11.23 |
| NAAA | N-acylethanolamine acid amidase | HGNC: 736 | 4q21.1 |
| NAP1L3 | nucleosome assembly protein 1-like 3 | HGNC: 7639 | Xq21.3-q22 |
| NDN | necdin, melanoma antigen (MAGE) family member | HGNC: 7675 | 15q11-q12 |
| NINJ2 | ninjurin 2 | HGNC: 7825 | 12p13 |
| NKX2-5 | NK2 homeobox 5 | HGNC: 2488 | 5q34 |
| NMNAT3 | nicotinamide nucleotide adenylyltransferase 3 | HGNC: 20989 | 3q23 |
| NNAT | neuronatin | HGNC: 7860 | 20q11.2-q12 |
| NOTCH4 | notch 4 | HGNC: 7884 | 6p21.3 |
| NUB1 | negative regulator of ubiquitin-like proteins 1 | HGNC: 17623 | 7q36 |
| OPRL1 | opiate receptor-like 1 | HGNC: 8155 | 20q13.33 |
| ADCYAP1 | adenylate cyclase activating polypeptide 1 (pituitary) | HGNC: 241 | 18p11 |
| PDE4B | phosphodiesterase 4B, cAMP-specific | HGNC: 8781 | 1p31 |
| PDE9A | phosphodiesterase 9A | HGNC: 8795 | 21q22.3 |
| PDXP | pyridoxal (pyridoxine, vitamin B6) phosphatase | HGNC: 30259 | 22q12.3 |
| PGA3 | pepsinogen 3, group I (pepsinogen A) | HGNC: 8885 | 11q13 |
| PLA2G4A | phospholipase A2, group IVA (cytosolic, calcium-dependent) | HGNC: 9035 | 1q25 |
| PLEKHG4B | pleckstrin homology domain containing, family G (with RhoGef domain) member 4B | HGNC: 29399 | 5p15.33 |
| POMZP3 | POM121 and ZP3 fusion | HGNC: 9203 | 7q11.2 |
| PPM1H | protein phosphatase, Mg2+/Mn2+ dependent, 1H | HGNC: 18583 | 12q14.1 |
| PPM1M | protein phosphatase, Mg2+/Mn2+ dependent, 1M | HGNC: 26506 | 3p21.31 |
| PPP1R13B | protein phosphatase 1, regulatory subunit 13B | HGNC: 14950 | 14q32.33 |
| PPP1R9A | protein phosphatase 1, regulatory subunit 9A | HGNC: 14946 | 7q21.3 |
| PTPRN | protein tyrosine phosphatase, receptor type, N | HGNC: 9676 | 2q35-q36.1 |
| RAD52 | RAD52 homolog (S. cerevisiae) | HGNC: 9824 | 12p13-p12.2 |

TABLE 7-continued

DEG up-regulated in PE-CVS compared to NP-CVS

| Approved symbol | Approved name | HGNC ID | Location |
|---|---|---|---|
| REST | RE1-silencing transcription factor | HGNC: 9966 | 4q12 |
| RFTN1 | raftlin, lipid raft linker 1 | HGNC: 30278 | 3p24.3 |
| RGPD1 | RANBP2-like and GRIP domain containing 1 | HGNC: 32414 | 2p11.2 |
| RIN1 | Ras and Rab interactor 1 | HGNC: 18749 | 11q13.2 |
| RPGR | retinitis pigmentosa GTPase regulator | HGNC: 10295 | Xp11.4 |
| RPL31 | ribosomal protein L31 | HGNC: 10334 | 2q11.2 |
| RPS4Y1 | ribosomal protein S4, Y-linked 1 | HGNC: 10425 | Yp11.3 |
| S100A12 | S100 calcium binding protein A12 | HGNC: 10489 | 1q21 |
| S100A8 | S100 calcium binding protein A8 | HGNC: 10498 | 1q12-q22 |
| SACS | sacsin molecular chaperone | HGNC: 10519 | 13q11 |
| SCARB2 | scavenger receptor class B, member 2 | HGNC: 1665 | 4q21.1 |
| SCML2 | sex comb on midleg-like 2 (*Drosophila*) | HGNC: 10581 | Xp22 |
| SEZ6L | seizure related 6 homolog (mouse)-like | HGNC: 10763 | 22q12.1 |
| SH3BP1 | SH3-domain binding protein 1 | HGNC: 10824 | 22q13.1 |
| SH3BP5L | SH3-binding domain protein 5-like | HGNC: 29360 | 1q44 |
| SIRT5 | sirtuin 5 | HGNC: 14933 | 6p23 |
| SLC13A5 | solute carrier family 13 (sodium-dependent citrate transporter), member 5 | HGNC: 23089 | 17p13.1 |
| SLC22A7 | solute carrier family 22 (organic anion transporter), member 7 | HGNC: 10971 | 6p21.1 |
| SLC25A29 | solute carrier family 25 (mitochondrial carnitine/acylcarnitine carrier), member 29 | HGNC: 20116 | 14q32.2 |
| SNRNP25 | small nuclear ribonucleoprotein 25 kDa (U11/U12) | HGNC: 14161 | 16p13.3 |
| SNRPN | small nuclear ribonucleoprotein polypeptide N | HGNC: 11164 | 15q11.2 |
| SNX16 | sorting nexin 16 | HGNC: 14980 | 8q21.13 |
| SORD | sorbitol dehydrogenase | HGNC: 11184 | 15q15-q21.1 |
| SPDEF | SAM pointed domain containing ETS transcription factor | HGNC: 17257 | 6p21.3 |
| SPRR2B | small proline-rich protein 2B | HGNC: 11262 | 1q21-q22 |
| SPRY1 | sprouty homolog 1, antagonist of FGF signaling (*Drosophila*) | HGNC: 11269 | 4q |
| SRF | serum response factor (c-fos serum response element-binding transcription factor) | HGNC: 11291 | 6p |
| STAG3 | stromal antigen 3 | HGNC: 11356 | 7q22 |
| STXBP2 | syntaxin binding protein 2 | HGNC: 11445 | 19p13.3-p13.2 |
| TBC1D7 | TBC1 domain family, member 7 | HGNC: 21066 | 6p23 |
| TGIF2 | TGFB-induced factor homeobox 2 | HGNC: 15764 | 20q11.23 |
| TMEM100 | transmembrane protein 100 | HGNC: 25607 | 17q23.1 |
| TMEM106C | transmembrane protein 106C | HGNC: 28775 | 12q13.1 |
| TMEM216 | transmembrane protein 216 | HGNC: 25018 | 11q13.1 |
| TMEM229B | transmembrane protein 229B | HGNC: 20130 | 14q23.3-q24.1 |
| TMSB15A | thymosin beta 15a | HGNC: 30744 | Xq21.33-q22.3 |
| TNFSF12 | tumor necrosis factor (ligand) superfamily, member 12 | HGNC: 11927 | 17p13.1 |
| TPTE | transmembrane phosphatase with tensin homology | HGNC: 12023 | 21p11 |
| TRIM3 | tripartite motif containing 3 | HGNC: 10064 | 11p15.5 |
| TRIM55 | tripartite motif containing 55 | HGNC: 14215 | 8q13.1 |
| TRMT2B | tRNA methyltransferase 2 homolog B (*S. cerevisiae*) | HGNC: 25748 | Xq22.1 |
| TRPV2 | transient receptor potential cation channel, subfamily V, member 2 | HGNC: 18082 | 17p11.2 |
| TRRAP | transformation/transcription domain-associated protein | HGNC: 12347 | 7q21.2-q22.1 |
| TSSC1 | tumor suppressing subtransferable candidate 1 | HGNC: 12383 | 2p25.3 |
| TUBB1 | tubulin, beta 1 class VI | HGNC: 16257 | 20q13.32 |
| UGT2B7 | UDP glucuronosyltransferase 2 family, polypeptide B7 | HGNC: 12554 | 4q13 |
| ULK3 | unc-51 like kinase 3 | HGNC: 19703 | 15q24.1 |
| WNT10B | wingless-type MMTV integration site family, member 10B | HGNC: 12775 | 12q13 |
| ZFP57 | ZFP57 zinc finger protein | HGNC: 18791 | 6p22.1 |
| ZKSCAN2 | zinc finger with KRAB and SCAN domains 2 | HGNC: 25677 | 16p12.1 |
| ZMYM3 | zinc finger, MYM-type 3 | HGNC: 13054 | Xq13.1 |
| ZNF101 | zinc finger protein 101 | HGNC: 12881 | 19p13.11 |
| ZNF383 | zinc finger protein 383 | HGNC: 18609 | 19q13.13 |
| ZNF385A | zinc finger protein 385A | HGNC: 17521 | 12q13.13 |
| ZNF469 | zinc finger protein 469 | HGNC: 23216 | 16q24 |
| ZNF542P | zinc finger protein 542, pseudogene | HGNC: 25393 | 19q13.43 |
| ZNF571 | zinc finger protein 571 | HGNC: 25000 | 19q13.12 |
| ZNF581 | zinc finger protein 581 | HGNC: 25017 | 19q13.42 |
| ZP3 | zona pellucida glycoprotein 3 (sperm receptor) | HGNC: 13189 | 7q11.23 |
| LOC100131366 | . . . | . . . | . . . |
| LOC100132147 | . . . | . . . | . . . |
| LOC100132999 | . . . | . . . | . . . |
| LOC100271836 | . . . | . . . | . . . |
| LOC100505956 | . . . | . . . | . . . |
| LOC151146 | . . . | . . . | . . . |
| LOC643529 | . . . | . . . | . . . |
| LOC728377 | . . . | . . . | . . . |

TABLE 7-continued

DEG up-regulated in PE-CVS compared to NP-CVS

| Approved symbol | Approved name | HGNC ID | Location |
|---|---|---|---|
| MGC34034 | . . . | . . . | . . . |
| PK155 | . . . | . . . | . . . |

TABLE 8

DEG down-regulated in PE-CVS compared to NP-CVS

| Approved symbol | Approved name | HGNC ID | Location | Literature DEC PMID |
|---|---|---|---|---|
| ACACA | acetyl-CoA carboxylase alpha | HGNC: 84 | 17q21 | |
| ACOT1 /// ACOT2 | acyl-CoA thioesterase 1 /// 2 | HGNC: 33128 /// HGNC: 18431 | 14q24.3 | |
| AGAP3 | ArfGAP with GTPase domain, ankyrin repeat and PH domain 3 | HGNC: 16923 | 7q36.1 | |
| AIF1L | allograft inflammatory factor 1-like | HGNC: 28904 | 9q34.13-q34.3 | |
| AKR7A3 | aldo-keto reductase family 7, member A3 (aflatoxin aldehyde reductase) | HGNC: 390 | 1p36.13 | |
| ALDH1A2 | aldehyde dehydrogenase 1 family, member A2 | HGNC: 15472 | 15q21.2 | |
| ALS2CL | ALS2 C-terminal like | HGNC: 20605 | 3p21.31 | |
| AOC1 | amine oxidase, copper containing 1 | HGNC: 80 | 7q36.1 | 20668027 |
| APC | adenomatous polyposis coli | HGNC: 583 | 5q21-q22 | |
| AQP2 | aquaporin 2 (collecting duct) | HGNC: 634 | 12q12-q13 | |
| ART1 | ADP-ribosyltransferase 1 | HGNC: 723 | 11p15 | |
| ASCL2 | achaete-scute family bHLH transcription factor 2 | HGNC: 739 | 11p15.5 | |
| AXIN1 | axin 1 | HGNC: 903 | 16p13.3 | |
| BAIAP2L1 | BAI1-associated protein 2-like 1 | HGNC: 21649 | 7q22.1 | |
| BDKRB2 | bradykinin receptor B2 | HGNC: 1030 | 14q32.1-q32.2 | |
| BEAN1 | brain expressed, associated with NEDD4, 1 | HGNC: 24160 | 16q21 | |
| BEX1 | brain expressed, X-linked 1 | HGNC: 1036 | Xq22.1 | |
| BLNK | B-cell linker | HGNC: 14211 | 10q23.2-q23.33 | |
| BSG | basigin (Ok blood group) | HGNC: 1116 | 19p13.3 | 12141934 |
| C12orf75 | chromosome 12 open reading frame 75 | HGNC: 35164 | 12q23.3 | |
| C3 | complement component 3 | HGNC: 1318 | 19p13.3-p13.2 | 8311932 |
| C4BPA | complement component 4 binding protein, alpha | HGNC: 1325 | 1q32 | |
| C7orf71 | chromosome 7 open reading frame 71 | HGNC: 22364 | 7p15.2 | |
| CA12 | carbonic anhydrase XII | HGNC: 1371 | 15q22 | |
| CA2 | carbonic anhydrase II | HGNC: 1373 | 8q21.2 | 9692790 |
| CC2D2B | coiled-coil and C2 domain containing 2B | HGNC: 31666 | 10q23.33 | |
| CCDC113 | coiled-coil domain containing 113 | HGNC: 25002 | 16q21 | |
| CCDC125 | coiled-coil domain containing 125 | HGNC: 28924 | 5q13.2 | |
| CFH /// CFHR1 | complement factor H /// complement factor H-related 1 | HGNC: 4883 /// HGNC: 4888 | 1q32 | |
| CHERP | calcium homeostasis endoplasmic reticulum protein | HGNC: 16930 | 19p13.1 | |
| CHRDL1 | chordin-like 1 | HGNC: 29861 | Xq23 | |
| CHST2 | carbohydrate (N-acetylglucosamine-6-O) sulfotransferase 2 | HGNC: 1970 | 3q24 | |
| CHST6 | carbohydrate (N-acetylglucosamine 6-O) sulfotransferase 6 | HGNC: 6938 | 16q22 | |
| CLASP2 | cytoplasmic linker associated protein 2 | HGNC: 17078 | 3p24.3 | |
| CLCN7 | chloride channel, voltage-sensitive 7 | HGNC: 2025 | 16p13 | |
| CLDN6 | claudin 6 | HGNC: 2048 | 16p13.3 | |
| CMAHP | cytidine monophospho-N-acetylneuraminic acid hydroxylase, pseudogene | HGNC: 2098 | 6p23-p22 | |
| CMTM4 | CKLF-like MARVEL transmembrane domain containing 4 | HGNC: 19175 | 16q22.1-q22.3 | |
| COL27A1 | collagen, type XXVII, alpha 1 | HGNC: 22986 | 9q33.1 | |
| COTL1 | coactosin-like F-actin binding protein 1 | HGNC: 18304 | 16q24.1 | |
| CPM | carboxypeptidase M | HGNC: 2311 | 12q15 | |
| CPXM2 | carboxypeptidase X (M14 family), member 2 | HGNC: 26977 | 10q26 | |
| CRH | corticotropin releasing hormone | HGNC: 2355 | 8q13 | 159239 |
| CRYBB1 | crystallin, beta B1 | HGNC: 2397 | 22q12.1 | |
| CUL1 | cullin 1 | HGNC: 2551 | 7q36.1 | |
| CYP4A11 | cytochrome P450, family 4, subfamily A, polypeptide 11 | HGNC: 2642 | 1p33 | |
| CYTH2 | cytohesin 2 | HGNC: 9502 | 19q13.32 | |
| DEPDC7 | DEP domain containing 7 | HGNC: 29899 | 11p13 | |
| DHRS2 | dehydrogenase/reductase (SDR family) member 2 | HGNC: 18349 | 14q11.2 | |
| DLGAP1 | discs, large (*Drosophila*) homolog-associated protein 1 | HGNC: 2905 | 18p11.3 | |
| DNAJC6 | DnaJ (Hsp40) homolog, subfamily C, member 6 | HGNC: 15469 | 1p31.3 | |
| DSC2 | desmocollin 2 | HGNC: 3036 | 18q12.1 | |

TABLE 8-continued

DEG down-regulated in PE-CVS compared to NP-CVS

| Approved symbol | Approved name | HGNC ID | Location | Literature DEC PMID |
|---|---|---|---|---|
| DUXAP10 | double homeobox A pseudogene 10 | HGNC: 32189 | 14q11.2 | |
| EFCAB2 | EF-hand calcium binding domain 2 | HGNC: 28166 | 1q44 | |
| EGLN3 | egl-9 family hypoxia-inducible factor 3 | HGNC: 14661 | 14q12 | |
| ELL2 | elongation factor, RNA polymerase II, 2 | HGNC: 17064 | 5q15 | |
| EPAS1 | endothelial PAS domain protein 1 | HGNC: 3374 | 2p21-p16 | |
| ERAP2 | endoplasmic reticulum aminopeptidase 2 | HGNC: 29499 | 5q15 | 24331737 |
| ERO1L | ERO1-like (S. cerevisiae) | HGNC: 13280 | 14q22.1 | |
| F11R | F11 receptor | HGNC: 14685 | 1q21.2-q21.3 | |
| F2R | coagulation factor II (thrombin) receptor | HGNC: 3537 | 5q13 | 12549865 |
| FABP7 | fatty acid binding protein 7, brain | HGNC: 3562 | 6q22-q23 | |
| FAM3B | family with sequence similarity 3, member B | HGNC: 1253 | 21q22.3 | |
| FHL2 | four and a half LIM domains 2 | HGNC: 3703 | 2q12.2 | |
| FKBP11 | FK506 binding protein 11, 19 kDa | HGNC: 18624 | 12q13.12 | |
| FLT4 | fms-related tyrosine kinase 4 | HGNC: 3767 | 5q34-q35 | 11297624 |
| FN1 | fibronectin 1 | HGNC: 3778 | 2q34 | 14611684 |
| FSTL3 | follistatin-like 3 (secreted glycoprotein) | HGNC: 3973 | 19p13 | 15130517 |
| GATA1 | GATA binding protein 1 (globin transcription factor 1) | HGNC: 4170 | Xp11.23 | |
| GDA | guanine deaminase | HGNC: 4212 | 9q21.13 | |
| GNG4 | guanine nucleotide binding protein (G protein), gamma 4 | HGNC: 4407 | 1q42.3 | |
| GNG7 | guanine nucleotide binding protein (G protein), gamma 7 | HGNC: 4410 | 19p13.3 | |
| GNLY | granulysin | HGNC: 4414 | 2p12-q11 | 21623991 |
| GOLGA8B | golgin A8 family, member B | HGNC: 31973 | 15q14 | |
| GPR158 | G protein-coupled receptor 158 | HGNC: 23689 | 10p12.31 | |
| GTPBP2 | GTP binding protein 2 | HGNC: 4670 | 6p21 | |
| GZMB | granzyme B (granzyme 2, cytotoxic T-lymphocyte-associated serine esterase 1) | HGNC: 4709 | 14q11.2 | 16451356 |
| HBE1 | hemoglobin, epsilon 1 | HGNC: 4830 | 11p15.5 | |
| HBZ | hemoglobin, zeta | HGNC: 4835 | 16p13.3 | |
| HCAR3 | hydroxycarboxylic acid receptor 3 | HGNC: 16824 | 12q24.31 | |
| HIVEP2 | human immunodeficiency virus type I enhancer binding protein 2 | HGNC: 4921 | 6q23-q24 | |
| HOXB7 | homeobox B7 | HGNC: 5118 | 17q21.32 | |
| HPS3 | Hermansky-Pudlak syndrome 3 | HGNC: 15597 | 3q24 | |
| HTR2B | 5-hydroxytryptamine (serotonin) receptor 2B, G protein-coupled | HGNC: 5294 | 2q36.3-q37.1 | |
| HYDIN | HYDIN, axonemal central pair apparatus protein | HGNC: 19368 | 16q22.2 | |
| IGFBP1 | insulin-like growth factor binding protein 1 | HGNC: 5469 | 7p13-p12 | 1385468 |
| IGKC | immunoglobulin kappa constant | HGNC: 5716 | 2p11.2 | |
| IL15 | interleukin 15 | HGNC: 5977 | 4q31 | 10952908 |
| IL1B | interleukin 1, beta | HGNC: 5992 | 2q14 | 16860880 |
| IL1RL1 | interleukin 1 receptor-like 1 | HGNC: 5998 | 2q12 | 23300625 |
| IL2RB | interleukin 2 receptor, beta | HGNC: 6009 | 22q13 | 21248224 |
| INPP4B | inositol polyphosphate-4-phosphatase, type II, 105 kDa | HGNC: 6075 | 4q31.1 | |
| ITCH | itchy E3 ubiquitin protein ligase | HGNC: 13890 | 20q11.22 | |
| ITGB6 | integrin, beta 6 | HGNC: 6161 | 2q24.2 | |
| KCNH2 | potassium voltage-gated channel, subfamily H (eag-related), member 2 | HGNC: 6251 | 7q36.1 | |
| KCNIP3 | Kv channel interacting protein 3, calsenilin | HGNC: 15523 | 2q21.1 | |
| KCNQ1 | potassium voltage-gated channel, KQT-like subfamily, member 1 | HGNC: 6294 | 11p15.5 | |
| KISS1R | KISS1 receptor | HGNC: 4510 | 19p13.3 | 24225150 |
| KLRC2 | killer cell lectin-like receptor subfamily C, member 2 | HGNC: 6375 | 12p13 | 16488482 |
| KRT14 | keratin 14 | HGNC: 6416 | 17q21.2 | |
| LAIR2 | leukocyte-associated immunoglobulin-like receptor 2 | HGNC: 6478 | 19q13.4 | |
| LAMA4 | laminin, alpha 4 | HGNC: 6484 | 6q21 | |
| LIAS | lipoic acid synthetase | HGNC: 16429 | 4p14 | |
| LIPH | lipase, member H | HGNC: 18483 | 3q27 | |
| LIPT1 | lipoyltransferase 1 | HGNC: 29569 | 2q11.2 | |
| LSS | lanosterol synthase (2,3-oxidosqualene-lanosterol cyclase) | HGNC: 6708 | 21q22.3 | |
| LTBR | lymphotoxin beta receptor (TNFR superfamily, member 3) | HGNC: 6718 | 12p13 | |
| MAGEB6 | melanoma antigen family B, 6 | HGNC: 23796 | Xp22.12 | |
| MAOB | monoamine oxidase B | HGNC: 6834 | Xp11.4-p11.3 | |
| MAP3K5 | mitogen-activated protein kinase kinase kinase 5 | HGNC: 6857 | 6q22.33 | |
| MLIP | muscular LMNA-interacting protein | HGNC: 21355 | 6p12.2-p12.1 | |
| MMD | monocyte to macrophage differentiation-associated | HGNC: 7153 | 17q | |
| MMP12 | matrix metallopeptidase 12 (macrophage elastase) | HGNC: 7158 | 11q22.3 | 20802175 |
| MUC15 | mucin 15, cell surface associated | HGNC: 14956 | 11p14.3 | 17720698 |
| MUC4 | mucin 4, cell surface associated | HGNC: 7514 | 3q29 | |
| MVK | mevalonate kinase | HGNC: 7530 | 12q24 | |
| NDP | Norrie disease (pseudoglioma) | HGNC: 7678 | Xp11.4-p11.3 | 16035034 |
| NDUFV2 | NADH dehydrogenase (ubiquinone) flavoprotein 2, 24 kDa | HGNC: 7717 | 18p11.22 | |

TABLE 8-continued

DEG down-regulated in PE-CVS compared to NP-CVS

| Approved symbol | Approved name | HGNC ID | Location | Literature DEC PMID |
|---|---|---|---|---|
| NOG | noggin | HGNC: 7866 | 17q22 | 11158592 |
| NOTUM | notum pectinacetylesterase homolog (Drosophila) | HGNC: 27106 | 17q25.3 | |
| NTN1 | netrin 1 | HGNC: 8029 | 17p13-p12 | |
| NTN4 | netrin 4 | HGNC: 13658 | 12q22 | |
| NUDT13 | nudix (nucleoside diphosphate linked moiety X)-type motif 13 | HGNC: 18827 | 10q22.3 | |
| OXGR1 | oxoglutarate (alpha-ketoglutarate) receptor 1 | HGNC: 4531 | 13q32.2 | |
| P4HA3 | prolyl 4-hydroxylase, alpha polypeptide III | HGNC: 30135 | 11q13 | |
| PAEP | progestagen-associated endometrial protein | HGNC: 8573 | 9q34 | 3194393 |
| PARP16 | poly (ADP-ribose) polymerase family, member 16 | HGNC: 26040 | 15q22.2 | |
| PAWR | PRKC, apoptosis, WT1, regulator | HGNC: 8614 | 12q21.2 | |
| PDE4C | phosphodiesterase 4C, cAMP-specific | HGNC: 8782 | 19p13.11 | 14715868 |
| PITPNC1 | phosphatidylinositol transfer protein, cytoplasmic 1 | HGNC: 21045 | 17q24.3 | |
| PLAC8 | placenta-specific 8 | HGNC: 19254 | 4q21.22 | |
| PLCXD2 | phosphatidylinositol-specific phospholipase C, X domain containing 2 | HGNC: 26462 | 3q13.2 | |
| PPDPF | pancreatic progenitor cell differentiation and proliferation factor | HGNC: 16142 | 20q13.33 | |
| PPP1R3C | protein phosphatase 1, regulatory subunit 3C | HGNC: 9293 | 10q23-q24 | |
| PRDM1 | PR domain containing 1, with ZNF domain | HGNC: 9346 | 6q21 | |
| PRG2 | proteoglycan 2, bone marrow (natural killer cell activator, eosinophil granule major basic protein) | HGNC: 9362 | 11q12 | |
| PRKAB2 | protein kinase, AMP-activated, beta 2 non-catalytic subunit | HGNC: 9379 | 1q21.2 | |
| PRL | prolactin | HGNC: 9445 | 6p22.3 | 10611264 |
| PSG11 | pregnancy specific beta-1-glycoprotein 11 | HGNC: 9516 | 19q13.2 | |
| PTPRS | protein tyrosine phosphatase, receptor type, S | HGNC: 9681 | 19p13.3 | |
| PVR | poliovirus receptor | HGNC: 9705 | 19q13.2 | |
| RAB12 | RAB12, member RAS oncogene family | HGNC: 31332 | 18p11.22 | |
| RBP4 | retinol binding protein 4, plasma | HGNC: 9922 | 10q23.33 | |
| RHD | Rh blood group, D antigen | HGNC: 10009 | 1p36.11 | |
| RNF14 | ring finger protein 14 | HGNC: 10058 | 5q23.3-q31.1 | |
| RORB | RAR-related orphan receptor B | HGNC: 10259 | 9q22 | |
| RSRC1 | arginine/serine-rich coiled-coil 1 | HGNC: 24152 | 3q25.32 | |
| RUFY3 | RUN and FYVE domain containing 3 | HGNC: 30285 | 4q13.3 | |
| SART3 | squamous cell carcinoma antigen recognized by T cells 3 | HGNC: 16860 | 12q24.11 | |
| SCARA5 | scavenger receptor class A, member 5 (putative) | HGNC: 28701 | 8p21.1 | 21858178 |
| SDHAP1 | Succinate dehydrogenase complex, subunit A, flavoprotein pseudogene 1 | HGNC: 32455 | 3q29 | |
| SEC24D | SEC24 family member D | HGNC: 10706 | 4q26 | |
| SEMA3C | sema domain, immunoglobulin domain (Ig), short basic domain, secreted, (semaphorin) 3C | HGNC: 10725 | 7q21-q31 | |
| SERPINA3 | serpin peptidase inhibitor, clade A (alpha-1 antiproteinase, antitrypsin), member 3 | HGNC: 16 | 14q32.1 | 8951488 |
| SFI1 | Sfi1 homolog, spindle assembly associated (yeast) | HGNC: 29064 | 22q12.2 | |
| SGSM1 | small G protein signaling modulator 1 | HGNC: 29410 | 22q11.23 | |
| SLC13A4 | solute carrier family 13 (sodium/sulfate symporter), member 4 | HGNC: 15827 | 7q33 | |
| SLC16A6 | solute carrier family 16, member 6 | HGNC: 10927 | 17q24.2 | |
| SLC25A15 | solute carrier family 25 (mitochondrial carrier; ornithine transporter) member 15 | HGNC: 10985 | 13q14 | |
| SLC26A7 | solute carrier family 26 (anion exchanger), member 7 | HGNC: 14467 | 8q23 | |
| SLC2A3 | solute carrier family 2 (facilitated glucose transporter), member 3 | HGNC: 11007 | 12p13.3 | 12915684 |
| SLC36A1 | solute carrier family 36 (proton/amino acid symporter), member 1 | HGNC: 18761 | 5q33.1 | |
| SLC44A3 | solute carrier family 44, member 3 | HGNC: 28689 | 1p22.1 | |
| SLCO4A1 | solute carrier organic anion transporter family, member 4A1 | HGNC: 10953 | 20q13.1 | |
| SNX25 | sorting nexin 25 | HGNC: 21883 | 4q35.1 | |
| SOWAHC | sosondowah ankyrin repeat domain family member C | HGNC: 26149 | 2q13 | |
| SP140L | SP140 nuclear body protein-like | HGNC: 25105 | 2q37.1 | |
| SPG20 | spastic paraplegia 20 (Troyer syndrome) | HGNC: 18514 | 13q13.1 | |
| SPOCK1 | sparc/osteonectin, cwcv and kazal-like domains proteoglycan (testican) 1 | HGNC: 11251 | 5q31.2 | |
| SSTR1 | somatostatin receptor 1 | HGNC: 11330 | 14q13 | |
| ST3GAL6 | ST3 beta-galactoside alpha-2,3-sialyltransferase 6 | HGNC: 18080 | 3q12.2 | |
| ST6GALNAC4 | ST6 (alpha-N-acetyl-neuraminyl-2,3-beta-galactosyl-1,3)-N-acetylgalactosaminide alpha-2,6-sialyltransferase 4 | HGNC: 17846 | 9q34 | |

TABLE 8-continued

DEG down-regulated in PE-CVS compared to NP-CVS

| Approved symbol | Approved name | HGNC ID | Location | Literature DEC PMID |
|---|---|---|---|---|
| SYCP2L | synaptonemal complex protein 2-like | HGNC: 21537 | 6p24.2 | |
| SYT1 | synaptotagmin I | HGNC: 11509 | 12q21.2 | |
| TES | testis derived transcript (3 LIM domains) | HGNC: 14620 | 7q31.2 | |
| THBS4 | thrombospondin 4 | HGNC: 11788 | 5q13 | |
| THUMPD2 | THUMP domain containing 2 | HGNC: 14890 | 2p22.2 | |
| TIAM1 | T-cell lymphoma invasion and metastasis 1 | HGNC: 11805 | 21q22.1 | |
| TLN2 | talin 2 | HGNC: 15447 | 15q15-q21 | |
| TMC4 | transmembrane channel-like 4 | HGNC: 22998 | 19q13.42 | |
| TMEM62 | transmembrane protein 62 | HGNC: 26269 | 15q15.2 | 24767823 |
| TOX3 | TOX high mobility group box family member 3 | HGNC: 11972 | 16q12.1 | |
| TPM1 | tropomyosin 1 (alpha) | HGNC: 12010 | 15q22.1 | |
| TRA@ | T cell receptor alpha locus | HGNC: 12027 | 14q11.2 | |
| TREML2 | triggering receptor expressed on myeloid cells-like 2 | HGNC: 21092 | 6p21.1 | |
| TSTD1 | thiosulfate sulfurtransferase (rhodanese)-like domain containing 1 | HGNC: 35410 | 1q23.3 | |
| TTC18 | tetratricopeptide repeat domain 18 | HGNC: 30726 | 10q22.3 | |
| USP5 | ubiquitin specific peptidase 5 (isopeptidase T) | HGNC: 12628 | 12p13 | |
| WT1 | Wilms tumor 1 | HGNC: 12796 | 11p13 | 11739471 |
| XRCC4 | X-ray repair complementing defective repair in Chinese hamster cells 4 | HGNC: 12831 | 5q14.2 | |
| ZFP62 | ZFP62 zinc finger protein | HGNC: 23241 | 5q35.3 | |
| ZNF165 | zinc finger protein 165 | HGNC: 12953 | 6p21 | |
| LOC153546 | . . . | . . . | . . . | . . . |
| LOC440157 | . . . | . . . | . . . | . . . |
| FLJ13744 | . . . | . . . | . . . | . . . |

TABLE 9

Enriched Biological processes for DEG down-regulated in PE-CVS compared to NP-CVS (DAVID Bioinformatics Resources 6.7)

| Enriched Biological Process | #Genes | Genes | Fold Enrichment | p value | Benjamini |
|---|---|---|---|---|---|
| GO: 0006952~defense response | 23 | F11R, KLRC2, C3, IL1RL1, GNLY, PRG2, CHST2, C4BPA, BDKRB2, IL15, COTL1, TRA@, CFHR1, ITGB6, SERPINA3, CRH, CFH, IL1B, ITCH, GNG7, F2R, FN1, BLNK | 3.285228593 | 1.58E−06 | 0.002391642 |
| GO: 0006954~inflammatory response | 16 | F11R, C3, CHST2, C4BPA, BDKRB2, IL15, CFHR1, ITGB6, SERPINA3, CFH, CRH, IL1B, ITCH, F2R, FN1, BLNK | 4.324635365 | 4.13E−06 | 0.003132854 |
| GO: 0009611~response to wounding | 19 | F11R, NOG, C3, CHST2, C4BPA, BDKRB2, IL15, TPM1, CFHR1, ITGB6, SERPINA3, CRH, CFH, IL1B, IGFBP1, ITCH, F2R, FN1, BLNK | 3.149130115 | 3.04E−05 | 0.015286151 |
| GO: 0008285~negative regulation of cell proliferation | 15 | RBP4, NOG, BDKRB2, IL15, PAWR, DHRS2, ALDH1A2, KISS1R, SSTR1, IL1B, ITCH, FABP7, CUL1, F2R, APC | 3.650034176 | 6.03E−05 | 0.02264638 |
| GO: 0042127~regulation of cell proliferation | 21 | XRCC4, RBP4, NOG, FLT4, EGLN3, BDKRB2, | 2.343999076 | 5.61E−04 | 0.156679481 |

TABLE 9-continued

Enriched Biological processes for DEG down-regulated in PE-CVS compared to NP-CVS
(DAVID Bioinformatics Resources 6.7)

| Enriched Biological Process | #Genes | Genes | Fold Enrichment | p value | Benjamini |
|---|---|---|---|---|---|
| | | IL15, PAWR, NTN1, MMP12, DHRS2, ALDH1A2, KISS1R, SSTR1, IL1B, ITCH, FABP7, PRL, CUL1, F2R, APC | | | |
| GO: 0002526~acute inflammatory response | 7 | CFHR1, C3, CFH, SERPINA3, IL1B, C4BPA, FN1 | 6.27458256 | 8.49E−04 | 0.193443436 |
| GO: 0046883~regulation of hormone secretion | 6 | RBP4, KISS1R, GPR109B, CRH, IL1B, KCNQ1 | 7.985832349 | 8.89E−04 | 0.17553566 |
| GO: 0048871~multicellular organismal homeostasis | 6 | RBP4, EPAS1, SERPINA3, ACACA, IL1B, F2R | 6.200763942 | 0.002749326 | 0.407110431 |
| GO: 0048584~positive regulation of response to stimulus | 9 | CFHR1, PVR, C3, CFH, CRH, IL1B, IL15, C4BPA, AXIN1 | 3.349988994 | 0.005404771 | 0.599354927 |
| GO: 0001894~tissue homeostasis | 5 | RBP4, EPAS1, SERPINA3, ACACA, F2R | 6.9717584 | 0.005586825 | 0.573020053 |
| GO: 0050778~positive regulation of immune response | 7 | CFHR1, PVR, C3, CFH, IL1B, IL15, C4BPA | 4.240752351 | 0.006079294 | 0.569176788 |
| GO: 0060249~anatomical structure homeostasis | 6 | RBP4, EPAS1, SERPINA3, ACACA, F2R, APC | 4.972310708 | 0.007035029 | 0.590846406 |
| GO: 0010627~regulation of protein kinase cascade | 9 | MAP3K5, LTBR, IL1RL1, IL1B, HTR2B, PRL, F2R, AXIN1, APC | 3.17508997 | 0.007392779 | 0.5798009 |
| GO: 0046887~positive regulation of hormone secretion | 4 | RBP4, KISS1R, GPR109B, CRH | 9.76046176 | 0.007706954 | 0.568049167 |
| GO: 0001655~urogenital system development | 6 | ALDH1A2, RBP4, NOG, CA2, WT1, APC | 4.79149941 | 0.008197726 | 0.565508003 |
| GO: 0044057~regulation of system process | 10 | KISS1R, EPAS1, GPR109B, CRH, IL1B, BDKRB2, KCNH2, TPM1, KCNQ1, F2R | 2.84285294 | 0.008537529 | 0.556922869 |
| GO: 0006956~complement activation | 4 | CFHR1, C3, CFH, C4BPA | 8.36611008 | 0.011796833 | 0.653664906 |
| GO: 0006959~humoral immune response | 5 | CFHR1, C3, CFH, C4BPA, BLNK | 5.559756699 | 0.012269978 | 0.647200259 |
| GO: 0002541~activation of plasma proteins involved in acute inflammatory response | 4 | CFHR1, C3, CFH, C4BPA | 8.171549381 | 0.012578263 | 0.636500333 |
| GO: 0051130~positive regulation of cellular component organization | 7 | KISS1R, C3, TIAM1, IL1B, TPM1, NTN1, APC | 3.397287795 | 0.016896621 | 0.725900409 |
| GO: 0015669~gas transport | 3 | HBZ, CA2, HBE1 | 14.64069264 | 0.017267525 | 0.716325311 |
| GO: 0046717~acid secretion | 3 | KISS1R, SLC26A7, BDKRB2 | 14.64069264 | 0.017267525 | 0.716325311 |
| GO: 0030097~hemopoiesis | 8 | XRCC4, DHRS2, HOXB7, EPAS1, HBZ, IL15, BLNK, APC | 2.977767995 | 0.017831541 | 0.711279469 |
| GO: 0002684~positive regulation of immune system process | 8 | CFHR1, PVR, C3, CFH, IL1B, IL15, ITCH, C4BPA | 2.952744734 | 0.018585144 | 0.710319549 |
| GO: 0003013~circulatory system process | 7 | ERAP2, BDKRB2, KCNH2, HTR2B, TPM1, KCNQ1, AQP2 | 3.305962854 | 0.019095627 | 0.70485324 |

TABLE 9-continued

Enriched Biological processes for DEG down-regulated in PE-CVS compared to NP-CVS
(DAVID Bioinformatics Resources 6.7)

| Enriched Biological Process | #Genes | Genes | Fold Enrichment | p value | Benjamini |
|---|---|---|---|---|---|
| GO: 0008015~blood circulation | 7 | ERAP2, BDKRB2, KCNH2, HTR2B, TPM1, KCNQ1, AQP2 | 3.305962854 | 0.019095627 | 0.70485324 |
| GO: 0070163~regulation of adiponectin secretion | 2 | GPR109B, IL1B | 87.84415584 | 0.022492665 | 0.748989022 |
| GO: 0060341~regulation of cellular localization | 8 | SYT1, RBP4, KISS1R, GPR109B, CRH, IL1B, KCNQ1, APC | 2.833682447 | 0.022691482 | 0.738410497 |
| GO: 0001822~kidney development | 5 | ALDH1A2, NOG, CA2, WT1, APC | 4.57521645 | 0.023438757 | 0.736669831 |
| GO: 0009894~regulation of catabolic process | 5 | PPP1R3C, GPR109B, IL1B, ITCH, APC | 4.57521645 | 0.023438757 | 0.736669831 |
| GO: 0009725~response to hormone stimulus | 10 | ALDH1A2, RBP4, BSG, FHL2, IL1B, CA2, IGFBP1, GNG4, RNF14, GNG7 | 2.393573729 | 0.023681675 | 0.727519347 |
| GO: 0046942~carboxylic acid transport | 6 | SLC36A1, KISS1R, SLC16A6, SLC26A7, BDKRB2, SLC25A15 | 3.585475749 | 0.025707542 | 0.744403169 |
| GO: 0015849~organic acid transport | 6 | SLC36A1, KISS1R, SLC16A6, SLC26A7, BDKRB2, SLC25A15 | 3.561249561 | 0.026373782 | 0.741618489 |
| GO: 0051046~regulation of secretion | 7 | SYT1, RBP4, KISS1R, GPR109B, CRH, IL1B, KCNQ1 | 3.04410441 | 0.027285984 | 0.742205581 |
| GO: 0007155~cell adhesion | 15 | PVR, F11R, TLN2, CLDN6, CPXM2, PTPRS, SPOCK1, MUC4, LAMA4, COL27A1, ITGB6, DSC2, APC, FN1, THBS4 | 1.882374768 | 0.027332218 | 0.73165635 |
| GO: 0002697~regulation of immune effector process | 5 | PVR, RBP4, C3, IL1B, IL15 | 4.348720586 | 0.02760069 | 0.72426926 |
| GO: 0022610~biological adhesion | 15 | PVR, F11R, TLN2, CLDN6, CPXM2, PTPRS, SPOCK1, MUC4, LAMA4, COL27A1, ITGB6, DSC2, APC, FN1, THBS4 | 1.879689497 | 0.027622076 | 0.713902032 |
| GO: 0048534~hemopoietic or lymphoid organ development | 8 | XRCC4, DHRS2, HOXB7, EPAS1, HBZ, IL15, BLNK, APC | 2.702897103 | 0.028401277 | 0.713626389 |
| GO: 0010817~regulation of hormone levels | 6 | ALDH1A2, DHRS2, RBP4, SLCO4A1, FAM3B, CRH | 3.490496259 | 0.028432612 | 0.703907645 |
| GO: 0034754~cellular hormone metabolic process | 4 | ALDH1A2, DHRS2, RBP4, CRH | 5.955535989 | 0.029086816 | 0.702351713 |
| GO: 0001890~placenta development | 4 | BSG, EPAS1, NDP, PRDM1 | 5.856277056 | 0.030370631 | 0.708537337 |
| GO: 0006040~amino sugar metabolic process | 3 | CHST6, ST3GAL6, CHST2 | 10.5412987 | 0.032161637 | 0.720077035 |
| GO: 0042445~hormone metabolic process | 5 | ALDH1A2, DHRS2, RBP4, SLCO4A1, CRH | 4.143592257 | 0.032177273 | 0.711200708 |
| GO: 0042129~regulation of T cell proliferation | 4 | IL1B, PAWR, IL15, ITCH | 5.667364893 | 0.033026613 | 0.711845228 |
| GO: 0043122~regulation of | 5 | LTBR, IL1RL1, | 4.104867096 | 0.033142832 | 0.704468375 |

TABLE 9-continued

Enriched Biological processes for DEG down-regulated in PE-CVS compared to NP-CVS
(DAVID Bioinformatics Resources 6.7)

| Enriched Biological Process | #Genes | Genes | Fold Enrichment | p value | Benjamini |
|---|---|---|---|---|---|
| I-kappaB kinase/NF-kappaB cascade | | IL1B, HTR2B, F2R | | | |
| GO: 0008219~cell death | 15 | LTBR, GPR109B, MMD, EGLN3, GZMB, PAWR, NTN1, KCNIP3, MAP3K5, TIAM1, SPG20, IL1B, CUL1, F2R, AXIN1 | 1.832631902 | 0.033238101 | 0.697027136 |
| GO: 0043009~chordate embryonic development | 9 | ASCL2, XRCC4, ALDH1A2, RBP4, NOG, HOXB7, EPAS1, PRDM1, TPM1 | 2.38851179 | 0.034502798 | 0.702447499 |
| GO: 0016265~death | 15 | LTBR, GPR109B, MMD, EGLN3, GZMB, PAWR, NTN1, KCNIP3, MAP3K5, TIAM1, SPG20, IL1B, CUL1, F2R, AXIN1 | 1.819975605 | 0.034936457 | 0.698923988 |
| GO: 0043408~regulation of MAPKKK cascade | 5 | MAP3K5, IL1B, F2R, AXIN1, APC | 4.029548433 | 0.035124446 | 0.692945523 |
| GO: 0009792~embryonic development ending in birth or egg hatching | 9 | ASCL2, XRCC4, ALDH1A2, RBP4, NOG, HOXB7, EPAS1, PRDM1, TPM1 | 2.367058092 | 0.036095685 | 0.695217503 |
| GO: 0007565~female pregnancy | 5 | BSG, CRH, IL1B, PRL, PSG11 | 3.992916175 | 0.036140548 | 0.688038826 |
| GO: 0045732~positive regulation of protein catabolic process | 3 | IL1B, ITCH, APC | 9.76046176 | 0.037082855 | 0.69007507 |
| GO: 0002520~immune system development | 8 | XRCC4, DHRS2, HOXB7, EPAS1, HBZ, IL15, BLNK, APC | 2.546207416 | 0.037432747 | 0.686212032 |
| GO: 0016477~cell migration | 8 | PVR, IL1B, SEMA3C, CLASP2, NTN1, THBS4, FN1, APC | 2.546207416 | 0.037432747 | 0.686212032 |
| GO: 0009968~negative regulation of signal transduction | 7 | NOG, IL1RL1, FSTL3, IL1B, PAWR, AXIN1, APC | 2.782394077 | 0.039681478 | 0.700599905 |
| GO: 0006915~apoptosis | 13 | LTBR, GPR109B, EGLN3, GZMB, PAWR, NTN1, KCNIP3, MAP3K5, TIAM1, IL1B, CUL1, AXIN1, F2R | 1.896966821 | 0.040454891 | 0.700702813 |
| GO: 0009719~response to endogenous stimulus | 10 | ALDH1A2, RBP4, BSG, FHL2, IL1B, CA2, IGFBP1, GNG4, RNF14, GNG7 | 2.168991502 | 0.04063477 | 0.695453292 |
| GO: 0051050~positive regulation of transport | 7 | RBP4, KISS1R, C3, GPR109B, CRH, IL1B, F2R | 2.75743987 | 0.041164097 | 0.693469585 |
| GO: 0010740~positive regulation of protein kinase cascade | 6 | LTBR, IL1B, HTR2B, PRL, F2R, AXIN1 | 3.156077455 | 0.041169601 | 0.686857828 |
| GO: 0030334~regulation of cell migration | 6 | LAMA4, KISS1R, TPM1, NTN1, F2R, APC | 3.118727426 | 0.042950909 | 0.6960231 |
| GO: 0012501~programmed cell death | 13 | LTBR, GPR109B, EGLN3, GZMB, PAWR, NTN1, KCNIP3, MAP3K5, TIAM1, IL1B, CUL1, | 1.869024592 | 0.044440699 | 0.702228226 |

TABLE 9-continued

Enriched Biological processes for DEG down-regulated in PE-CVS compared to NP-CVS
(DAVID Bioinformatics Resources 6.7)

| Enriched Biological Process | #Genes | Genes | Fold Enrichment | p value | Benjamini |
|---|---|---|---|---|---|
| GO: 0007262~STAT protein nuclear translocation | 2 | AXIN1, F2R PRL, F2R | 43.92207792 | 0.044482643 | 0.696292693 |
| GO: 0002824~positive regulation of adaptive immune response based on somatic recombination of immune receptors built from immunoglobulin superfamily domains | 3 | PVR, C3, IL1B | 8.784415584 | 0.044962609 | 0.69407898 |
| GO: 0008284~positive regulation of cell proliferation | 10 | XRCC4, ALDH1A2, NOG, FLT4, IL1B, IL15, PRL, NTN1, MMP12, F2R | 2.121839513 | 0.045617995 | 0.693355795 |
| GO: 0048568~embryonic organ development | 6 | ALDH1A2, RBP4, NOG, HOXB7, EPAS1, PRDM1 | 3.064331018 | 0.04575653 | 0.688483791 |
| GO: 0050678~regulation of epithelial cell proliferation | 4 | NOG, PRL, MMP12, APC | 4.948966526 | 0.046415088 | 0.687892226 |
| GO: 0002821~positive regulation of adaptive immune response | 3 | PVR, C3, IL1B | 8.50104734 | 0.047714819 | 0.692355325 |

TABLE 10

Overlap of DEG down-regulated in PE-CVS and up-regulated in LSE (FIG. 11A)

| Approved symbol | Approved name | HGNC ID | Location |
|---|---|---|---|
| BAIAP2L1 | BAI1-associated protein 2-like 1 | HGNC: 21649 | 7q22.1 |
| BDKRB2 | bradykinin receptor B2 | HGNC: 1030 | 14q32.1-q32.2 |
| BLNK | B-cell linker | HGNC: 14211 | 10q23.2-q23.33 |
| C12orf75 | chromosome 12 open reading frame 75 | HGNC: 35164 | 12q23.3 |
| C3 | complement component 3 | HGNC: 1318 | 19p13.3-p13.2 |
| C4BPA | complement component 4 binding protein, alpha | HGNC: 1325 | 1q32 |
| CA12 | carbonic anhydrase XII | HGNC: 1371 | 15q22 |
| CHST2 | carbohydrate (N-acetylglucosamine-6-O) sulfotransferase 2 | HGNC: 1970 | 3q24 |
| CMAHP | cytidine monophospho-N-acetylneuraminic acid hydroxylase, pseudogene | HGNC: 2098 | 6p23-p22 |
| DNAJC6 | DnaJ (Hsp40) homolog, subfamily C, member 6 | HGNC: 15469 | 1p31.3 |
| DSC2 | desmocollin 2 | HGNC: 3036 | 18q12.1 |
| ELL2 | elongation factor, RNA polymerase II, 2 | HGNC: 17064 | 5q15 |
| EPAS1 | endothelial PAS domain protein 1 | HGNC: 3374 | 2p21-p16 |
| ERO1L | ERO1-like (S. cerevisiae) | HGNC: 13280 | 14q22.1 |
| GNG4 | guanine nucleotide binding protein (G protein), gamma 4 | HGNC: 4407 | 1q42.3 |
| GNLY | granulysin | HGNC: 4414 | 2p12-q11 |
| GTPBP2 | GTP binding protein 2 | HGNC: 4670 | 6p21 |
| GZMB | granzyme B (granzyme 2, cytotoxic T-lymphocyte-associated serine esterase 1) | HGNC: 4709 | 14q11.2 |
| HPS3 | Hermansky-Pudlak syndrome 3 | HGNC: 15597 | 3q24 |
| IGFBP1 | insulin-like growth factor binding protein 1 | HGNC: 5469 | 7p13-p12 |
| IL15 | interleukin 15 | HGNC: 5977 | 4q31 |
| IL1B | interleukin 1, beta | HGNC: 5992 | 2q14 |
| IL2RB | interleukin 2 receptor, beta | HGNC: 6009 | 22q13 |
| INPP4B | inositol polyphosphate-4-phosphatase, type II, 105 kDa | HGNC: 6075 | 4q31.1 |
| ITGB6 | integrin, beta 6 | HGNC: 6161 | 2q24.2 |
| LAMA4 | laminin, alpha 4 | HGNC: 6484 | 6q21 |
| MAOB | monoamine oxidase B | HGNC: 6834 | Xp11.4-p11.3 |
| MAP3K5 | mitogen-activated protein kinase kinase kinase 5 | HGNC: 6857 | 6q22.33 |
| PAEP | progestagen-associated endometrial protein | HGNC: 8573 | 9q34 |
| PVR | poliovirus receptor | HGNC: 9705 | 19q13.2 |
| RBP4 | retinol binding protein 4, plasma | HGNC: 9922 | 10q23-q24 |
| RUFY3 | RUN and FYVE domain containing 3 | HGNC: 30285 | 4q13.3 |
| SCARA5 | scavenger receptor class A, member 5 (putative) | HGNC: 28701 | 8p21.1 |
| SLCO4A1 | solute carrier organic anion transporter family, member 4A1 | HGNC: 10953 | 20q13.1 |

TABLE 10-continued

Overlap of DEG down-regulated in PE-CVS and up-regulated in LSE (FIG. 11A)

| Approved symbol | Approved name | HGNC ID | Location |
|---|---|---|---|
| SPOCK1 | sparc/osteonectin, cwcv and kazal-like domains proteoglycan (testican) 1 | HGNC: 11251 | 5q31.2 |
| TES | testis derived transcript (3 LIM domains) | HGNC: 14620 | 7q31.2 |
| TIAM1 | T-cell lymphoma invasion and metastasis 1 | HGNC: 11805 | 21q22.1 |
| ZNF165 | zinc finger protein 165 | HGNC: 12953 | 6p21 |

TABLE 11

Overlap of DEG down-regulated in PE-CVS and up-regulated in intDEC-EP (FIG. 11B)

| Approved symbol | Approved name | HGNC ID | Location |
|---|---|---|---|
| AIF1L | allograft inflammatory factor 1-like | HGNC: 28904 | 9q34.13-q34.3 |
| CHRDL1 | chordin-like 1 | HGNC: 29861 | Xq23 |
| CHST2 | carbohydrate (N-acetylglucosamine-6-O) sulfotransferase 2 | HGNC: 1970 | 3q24 |
| COTL1 | coactosin-like 1 (*Dictyostelium*) | HGNC: 18304 | 16q24.1 |
| DNAJC6 | DnaJ (Hsp40) homolog, subfamily C, member 6 | HGNC: 15469 | 1p31.3 |
| ELL2 | elongation factor, RNA polymerase II, 2 | HGNC: 17064 | 5q15 |
| EPAS1 | endothelial PAS domain protein 1 | HGNC: 3374 | 2p21-p16 |
| F2R | coagulation factor II (thrombin) receptor | HGNC: 3537 | 5q13 |
| GNG4 | guanine nucleotide binding protein (G protein), gamma 4 | HGNC: 4407 | 1q42.3 |
| GNLY | granulysin | HGNC: 4414 | 2p12-q11 |
| GZMB | granzyme B (granzyme 2, cytotoxic T-lymphocyte-associated serine esterase 1) | HGNC: 4709 | 14q11.2 |
| HTR2B | 5-hydroxytryptamine (serotonin) receptor 2B, G protein-coupled | HGNC: 5294 | 2q36.3-q37.1 |
| IGFBP1 | insulin-like growth factor binding protein 1 | HGNC: 5469 | 7p13-p12 |
| IL15 | interleukin 15 | HGNC: 5977 | 4q31 |
| IL1RL1 | interleukin 1 receptor-like 1 | HGNC: 5998 | 2q12 |
| IL2RB | interleukin 2 receptor, beta | HGNC: 6009 | 22q13 |
| LAMA4 | laminin, alpha 4 | HGNC: 6484 | 6q21 |
| LIPH | lipase, member H | HGNC: 18483 | 3q27 |
| MAOB | monoamine oxidase B | HGNC: 6834 | Xp11.4-p11.3 |
| MAP3K5 | mitogen-activated protein kinase kinase kinase 5 | HGNC: 6857 | 6q22.33 |
| MUC15 | mucin 15, cell surface associated | HGNC: 14956 | 11p14.3 |
| NDP | Norrie disease (pseudoglioma) | HGNC: 7678 | Xp11.4-p11.3 |
| NOG | noggin | HGNC: 7866 | 17q22 |
| P4HA3 | prolyl 4-hydroxylase, alpha polypeptide III | HGNC: 30135 | 11q13 |
| PPP1R3C | protein phosphatase 1, regulatory subunit 3C | HGNC: 9293 | 10q23-q24 |
| PRL | prolactin | HGNC: 9445 | 6p22.3 |
| RBP4 | retinol binding protein 4, plasma | HGNC: 9922 | 10q23-q24 |
| SCARA5 | scavenger receptor class A, member 5 (putative) | HGNC: 28701 | 8p21.1 |
| SLC25A15 | solute carrier family 25 (mitochondrial carrier; ornithine transporter) member 15 | HGNC: 10985 | 13q14 |
| SNX25 | sorting nexin 25 | HGNC: 21883 | 4q35.1 |
| SPOCK1 | sparc/osteonectin, cwcv and kazal-like domains proteoglycan (testican) 1 | HGNC: 11251 | 5q31.2 |
| TLN2 | talin 2 | HGNC: 15447 | 15q15-q21 |

TABLE 12

Overlap of DEG down-regulated in PE-CVS and up-regulated in intDEC-EP & LSE (FIG. 11C)

| Approved symbol | Approved name | HGNC ID | Location |
|---|---|---|---|
| CHST2 | carbohydrate (N-acetylglucosamine-6-O) sulfotransferase 2 | HGNC: 1970 | 3q24 |
| DNAJC6 | DnaJ (Hsp40) homolog, subfamily C, member 6 | HGNC: 15469 | 1p31.3 |
| ELL2 | elongation factor, RNA polymerase II, 2 | HGNC: 17064 | 5q15 |
| EPAS1 | endothelial PAS domain protein 1 | HGNC: 3374 | 2p21-p16 |
| GNG4 | guanine nucleotide binding protein (G protein), gamma 4 | HGNC: 4407 | 1q42.3 |
| GNLY | granulysin | HGNC: 4414 | 2p12-q11 |
| GZMB | granzyme B (granzyme 2, cytotoxic T-lymphocyte-associated serine esterase 1) | HGNC: 4709 | 14q11.2 |
| IGFBP1 | insulin-like growth factor binding protein 1 | HGNC: 5469 | 7p13-p12 |
| IL15 | interleukin 15 | HGNC: 5977 | 4q31 |

TABLE 12-continued

Overlap of DEG down-regulated in PE-CVS and up-regulated in intDEC-EP & LSE (FIG. 11C)

| Approved symbol | Approved name | HGNC ID | Location |
|---|---|---|---|
| IL2RB | interleukin 2 receptor, beta | HGNC: 6009 | 22q13 |
| LAMA4 | laminin, alpha 4 | HGNC: 6484 | 6q21 |
| MAOB | monoamine oxidase B | HGNC: 6834 | Xp11.4-p11.3 |
| MAP3K5 | mitogen-activated protein kinase kinase kinase 5 | HGNC: 6857 | 6q22.33 |
| RBP4 | retinol binding protein 4, plasma | HGNC: 9922 | 10q23-q24 |
| SCARA5 | scavenger receptor class A, member 5 (putative) | HGNC: 28701 | 8p21.1 |
| SPOCK1 | sparc/osteonectin, cwcv and kazal-like domains proteoglycan (testican) 1 | HGNC: 11251 | 5q31.2 |

TABLE 13

Overlap of DEG down-regulated in PE-CVS and up-regulated in intDEC-IUP (FIG. 12A)

| Approved symbol | Approved name | HGNC ID | Location |
|---|---|---|---|
| ACOT1 /// ACOT2 | acyl-CoA thioesterase 1 /// acyl-CoA thioesterase 2 | HGNC: 33128 /// HGNC: 18431 | 14q24.3 |
| AIF1L | allograft inflammatory factor 1-like | HGNC: 28904 | 9q34.13-q34.3 |
| CFH /// CFHR1 | complement factor H /// complement factor H-related 1 | HGNC: 4883 /// HGNC: 4888 | 1q32 |
| CHRDL1 | chordin-like 1 | HGNC: 29861 | Xq23 |
| CHST2 | carbohydrate (N-acetylglucosamine-6-O) sulfotransferase 2 | HGNC: 1970 | 3q24 |
| COTL1 | coactosin-like 1 (*Dictyostelium*) | HGNC: 18304 | 16q24.1 |
| CPXM2 | carboxypeptidase X (M14 family), member 2 | HGNC: 26977 | 10q26 |
| DNAJC6 | DnaJ (Hsp40) homolog, subfamily C, member 6 | HGNC: 15469 | 1p31.3 |
| ELL2 | elongation factor, RNA polymerase II, 2 | HGNC: 17064 | 5q15 |
| EPAS1 | endothelial PAS domain protein 1 | HGNC: 3374 | 2p21-p16 |
| F2R | coagulation factor II (thrombin) receptor | HGNC: 3537 | 5q13 |
| GNG4 | guanine nucleotide binding protein (G protein), gamma 4 | HGNC: 4407 | 1q42.3 |
| GNLY | granulysin | HGNC: 4414 | 2p12-q11 |
| GZMB | granzyme B (granzyme 2, cytotoxic T-lymphocyte-associated serine esterase 1) | HGNC: 4709 | 14q11.2 |
| HTR2B | 5-hydroxytryptamine (serotonin) receptor 2B, G protein-coupled | HGNC: 5294 | 2q36.3-q37.1 |
| IGFBP1 | insulin-like growth factor binding protein 1 | HGNC: 5469 | 7p13-p12 |
| IL15 | interleukin 15 | HGNC: 5977 | 4q31 |
| IL1RL1 | interleukin 1 receptor-like 1 | HGNC: 5998 | 2q12 |
| IL2RB | interleukin 2 receptor, beta | HGNC: 6009 | 22q13 |
| LAMA4 | laminin, alpha 4 | HGNC: 6484 | 6q21 |
| LIPH | lipase, member H | HGNC: 18483 | 3q27 |
| LSS | lanosterol synthase (2,3-oxidosqualene-lanosterol cyclase) | HGNC: 6708 | 21q22.3 |
| MAOB | monoamine oxidase B | HGNC: 6834 | Xp11.4-p11.3 |
| MAP3K5 | mitogen-activated protein kinase kinase kinase 5 | HGNC: 6857 | 6q22.33 |
| MUC15 | mucin 15, cell surface associated | HGNC: 14956 | 11p14.3 |
| NDP | Norrie disease (pseudoglioma) | HGNC: 7678 | Xp11.4-p11.3 |
| P4HA3 | prolyl 4-hydroxylase, alpha polypeptide III | HGNC: 30135 | 11q13 |
| PPP1R3C | protein phosphatase 1, regulatory subunit 3C | HGNC: 9293 | 10q23-q24 |
| PRG2 | proteoglycan 2, bone marrow (natural killer cell activator, eosinophil granule major basic protein) | HGNC: 9362 | 11q12 |
| PRKAB2 | protein kinase, AMP-activated, beta 2 non-catalytic subunit | HGNC: 9379 | 1q21.2 |
| PRL | prolactin | HGNC: 9445 | 6p22.3 |
| RBP4 | retinol binding protein 4, plasma | HGNC: 9922 | 10q23-q24 |
| SCARA5 | scavenger receptor class A, member 5 (putative) | HGNC: 28701 | 8p21.1 |
| SLC16A6 | solute carrier family 16, member 6 | HGNC: 10927 | 17q24.2 |
| SLC25A15 | solute carrier family 25 (mitochondrial carrier; ornithine transporter) member 15 | HGNC: 10985 | 13q14 |
| SNX25 | sorting nexin 25 | HGNC: 21883 | 4q35.1 |
| SPOCK1 | sparc/osteonectin, cwcv and kazal-like domains proteoglycan (testican) 1 | HGNC: 11251 | 5q31.2 |

TABLE 14

Overlap of DEG down-regulated in PE-CVS and up-regulated in confDEC-IUP (FIG. 12B)

| Approved symbol | Approved name | HGNC ID | Location |
|---|---|---|---|
| ACOT1 /// ACOT2 | acyl-CoA thioesterase 1 /// acyl-CoA thioesterase 2 | HGNC: 33128 /// HGNC: 18431 | 14q24.3 |
| AIF1L | allograft inflammatory factor 1-like | HGNC: 28904 | 9q34.13-q34.3 |
| CFH /// CFHR1 | complement factor H /// complement factor H-related 1 | HGNC: 4883 /// HGNC: 4888 | 1q32 |
| CHRDL1 | chordin-like 1 | HGNC: 29861 | Xq23 |
| CHST2 | carbohydrate (N-acetylglucosamine-6-O) sulfotransferase 2 | HGNC: 1970 | 3q24 |
| COTL1 | coactosin-like 1 (*Dictyostelium*) | HGNC: 18304 | 16q24.1 |
| CPXM2 | carboxypeptidase X (M14 family), member 2 | HGNC: 26977 | 10q26 |
| DNAJC6 | DnaJ (Hsp40) homolog, subfamily C, member 6 | HGNC: 15469 | 1p31.3 |
| EFCAB2 | EF-hand calcium binding domain 2 | HGNC: 28166 | 1q44 |
| ELL2 | elongation factor, RNA polymerase II, 2 | HGNC: 17064 | 5q15 |
| EPAS1 | endothelial PAS domain protein 1 | HGNC: 3374 | 2p21-p16 |
| F2R | coagulation factor II (thrombin) receptor | HGNC: 3537 | 5q13 |
| FSTL3 | follistatin-like 3 (secreted glycoprotein) | HGNC: 3973 | 19p13 |
| GNG4 | guanine nucleotide binding protein (G protein), gamma 4 | HGNC: 4407 | 1q42.3 |
| GNLY | granulysin | HGNC: 4414 | 2p12-q11 |
| GZMB | granzyme B (granzyme 2, cytotoxic T-lymphocyte-associated serine esterase 1) | HGNC: 4709 | 14q11.2 |
| HTR2B | 5-hydroxytryptamine (serotonin) receptor 2B, G protein-coupled | HGNC: 5294 | 2q36.3-q37.1 |
| IGFBP1 | insulin-like growth factor binding protein 1 | HGNC: 5469 | 7p13-p12 |
| IL15 | interleukin 15 | HGNC: 5977 | 4q31 |
| IL1B | interleukin 1, beta | HGNC: 5992 | 2q14 |
| IL1RL1 | interleukin 1 receptor-like 1 | HGNC: 5998 | 2q12 |
| IL2RB | interleukin 2 receptor, beta | HGNC: 6009 | 22q13 |
| LAMA4 | laminin, alpha 4 | HGNC: 6484 | 6q21 |
| LIPH | lipase, member H | HGNC: 18483 | 3q27 |
| LSS | lanosterol synthase (2,3-oxidosqualene-lanosterolcyclase) | HGNC: 6708 | 21q22.3 |
| MAOB | monoamine oxidase B | HGNC: 6834 | Xp11.4-p11.3 |
| MAP3K5 | mitogen-activated protein kinase kinase kinase 5 | HGNC: 6857 | 6q22.33 |
| MUC15 | mucin 15, cell surface associated | HGNC: 14956 | 11p14.3 |
| NDP | Norrie disease (pseudoglioma) | HGNC: 7678 | Xp11.4-p11.3 |
| NOG | noggin | HGNC: 7866 | 17q22 |
| P4HA3 | prolyl 4-hydroxylase, alpha polypeptide III | HGNC: 30135 | 11q13 |
| PPP1R3C | protein phosphatase 1, regulatory subunit 3C | HGNC: 9293 | 10q23-q24 |
| PRG2 | proteoglycan 2, bone marrow (natural killer cell activator, eosinophil granule major basic protein) | HGNC: 9362 | 11q12 |
| PRKAB2 | protein kinase, AMP-activated, beta 2 non-catalytic subunit | HGNC: 9379 | 1q21.2 |
| PRL | prolactin | HGNC: 9445 | 6p22.3 |
| PVR | poliovirus receptor | HGNC: 9705 | 19q13.2 |
| RBP4 | retinol binding protein 4, plasma | HGNC: 9922 | 10q23-q24 |
| RNF14 | ring finger protein 14 | HGNC: 10058 | 5q23.3-q31.1 |
| RORB | RAR-related orphan receptor B | HGNC: 10259 | 9q22 |
| SCARA5 | scavenger receptor class A, member 5 (putative) | HGNC: 28701 | 8p21.1 |
| SERPINA3 | serpin peptidase inhibitor, clade A (alpha-1 antiproteinase, antitrypsin), member 3 | HGNC: 16 | 14q32.1 |
| SLC16A6 | solute carrier family 16, member 6 | HGNC: 10927 | 17q24.2 |
| SNX25 | sorting nexin 25 | HGNC: 21883 | 4q35.1 |
| SPOCK1 | sparc/osteonectin, cwcv and kazal-like domains proteoglycan (testican) 1 | HGNC: 11251 | 5q31.2 |
| TLN2 | talin 2 | HGNC: 15447 | 15q15-q21 |
| WT1 | Wilms tumor 1 | HGNC: 12796 | 11p13 |

TABLE 15

Overlap of DEG down-regulated in PE-CVS and up-regulated in intDEC-IUP and intDEC-EP (FIG. 12C)

| Approved symbol | Approved name | HGNC ID | Location |
|---|---|---|---|
| AIF1L | allograft inflammatory factor 1-like | HGNC: 28904 | 9q34.13-q34.3 |
| CHRDL1 | chordin-like 1 | HGNC: 29861 | Xq23 |
| CHST2 | carbohydrate (N-acetylglucosamine-6-O) sulfotransferase 2 | HGNC: 1970 | 3q24 |
| COTL1 | coactosin-like 1 (*Dictyostelium*) | HGNC: 18304 | 16q24.1 |
| DNAJC6 | DnaJ (Hsp40) homolog, subfamily C, member 6 | HGNC: 15469 | 1p31.3 |
| ELL2 | elongation factor, RNA polymerase II, 2 | HGNC: 17064 | 5q15 |
| EPAS1 | endothelial PAS domain protein 1 | HGNC: 3374 | 2p21-p16 |
| F2R | coagulation factor II (thrombin) receptor | HGNC: 3537 | 5q13 |
| GNG4 | guanine nucleotide binding protein (G protein), gamma 4 | HGNC: 4407 | 1q42.3 |

TABLE 15-continued

Overlap of DEG down-regulated in PE-CVS and up-regulated in intDEC-IUP and intDEC-EP (FIG. 12C)

| Approved symbol | Approved name | HGNC ID | Location |
|---|---|---|---|
| GNLY | granulysin | HGNC: 4414 | 2p12-q11 |
| GZMB | granzyme B (granzyme 2, cytotoxic T-lymphocyte-associated serine esterase 1) | HGNC: 4709 | 14q11.2 |
| HTR2B | 5-hydroxytryptamine (serotonin) receptor 2B, G protein-coupled | HGNC: 5294 | 2q36.3-q37.1 |
| IGFBP1 | insulin-like growth factor binding protein 1 | HGNC: 5469 | 7p13-p12 |
| IL15 | interleukin 15 | HGNC: 5977 | 4q31 |
| IL1RL1 | interleukin 1 receptor-like 1 | HGNC: 5998 | 2q12 |
| IL2RB | interleukin 2 receptor, beta | HGNC: 6009 | 22q13 |
| LAMA4 | laminin, alpha 4 | HGNC: 6484 | 6q21 |
| LIPH | lipase, member H | HGNC: 18483 | 3q27 |
| MAOB | monoamine oxidase B | HGNC: 6834 | Xp11.4-p11.3 |
| MAP3K5 | mitogen-activated protein kinase kinase kinase 5 | HGNC: 6857 | 6q22.33 |
| MUC15 | mucin 15, cell surface associated | HGNC: 14956 | 11p14.3 |
| NDP | Norrie disease (pseudoglioma) | HGNC: 7678 | Xp11.4-p11.3 |
| P4HA3 | prolyl 4-hydroxylase, alpha polypeptide III | HGNC: 30135 | 11q13 |
| PPP1R3C | protein phosphatase 1, regulatory subunit 3C | HGNC: 9293 | 10q23-q24 |
| PRL | prolactin | HGNC: 9445 | 6p22.3 |
| RBP4 | retinol binding protein 4, plasma | HGNC: 9922 | 10q23-q24 |
| SCARA5 | scavenger receptor class A, member 5 (putative) | HGNC: 28701 | 8p21.1 |
| SLC25A15 | solute carrier family 25 (mitochondrial carrier; ornithine transporter) member 15 | HGNC: 10985 | 13q14 |
| SNX25 | sorting nexin 25 | HGNC: 21883 | 4q35.1 |
| SPOCK1 | sparc/osteonectin, cwcv and kazal-like domains proteoglycan (testican) 1 | HGNC: 11251 | 5q31.2 |

TABLE 16

PE-CVS down-regulated genes linked to decidualization

| Approved symbol | Approved name | HGNC ID | Location | LSE | intDEC-EP | intDEC-IUP | confDEC-IUP | Pubmed DEC |
|---|---|---|---|---|---|---|---|---|
| ACOT1 /// ACOT2 | acyl-CoA thioesterase 1 /// 2 | HGNC: 33128 /// HGNC: 18431 | 14q24.3 | | | ✓ | ✓ | |
| AIF1L | allograft inflammatory factor 1-like | HGNC: 28904 | 9q34.13-q34.3 | | ✓ | ✓ | ✓ | |
| BAIAP2L1 | BAI1-associated protein 2-like 1 | HGNC: 21649 | 7q22.1 | ✓ | | | | |
| BDKRB2 | bradykinin receptor B2 | HGNC: 1030 | 14q32.1-q32.2 | ✓ | | | | |
| BLNK | B-cell linker | HGNC: 14211 | 10q23.2-q23.33 | ✓ | | | | |
| C12orf75 | chromosome 12 open reading frame 75 | HGNC: 35164 | 12q23.3 | ✓ | | | | |
| C3 | complement component 3 | HGNC: 1318 | 19p13.3-p13.2 | ✓ | | | | ✓ |
| C4BPA | complement component 4 binding protein, alpha | HGNC: 1325 | 1q32 | ✓ | | | | |
| CA12 | carbonic anhydrase XII | HGNC: 1371 | 15q22 | ✓ | | | | |
| CFH /// CFHR1 | complement factor H /// complement factor H-related 1 | HGNC: 4883 /// HGNC: 4888 | 1q32 | | | ✓ | ✓ | |
| CHRDL1 | chordin-like 1 | HGNC: 29861 | Xq23 | | ✓ | ✓ | ✓ | |
| CHST2 | carbohydrate (N-acetylglucosamine-6-O) sulfotransferase 2 | HGNC: 1970 | 3q24 | ✓ | ✓ | ✓ | ✓ | |
| CMAHP | cytidine monophospho-N-acetylneuraminic acid hydroxylase, pseudogene | HGNC: 2098 | 6p23-p22 | ✓ | | | | |
| COTL1 | coactosin-like F-actin binding protein 1 | HGNC: 18304 | 16q24.1 | | ✓ | ✓ | ✓ | |
| CPXM2 | carboxypeptidase X (M14 family), member 2 | HGNC: 26977 | 10q26 | | | ✓ | ✓ | |
| DNAJC6 | DnaJ (Hsp40) homolog, subfamily C, member 6 | HGNC: 15469 | 1p31.3 | ✓ | ✓ | ✓ | ✓ | |
| DSC2 | desmocollin 2 | HGNC: 3036 | 18q12.1 | ✓ | | | | |
| EFCAB2 | EF-hand calcium binding domain 2 | HGNC: 28166 | 1q44 | | | | ✓ | |
| ELL2 | elongation factor, RNA polymerase II, 2 | HGNC: 17064 | 5q15 | ✓ | ✓ | ✓ | ✓ | |
| EPAS1 | endothelial PAS domain protein 1 | HGNC: 3374 | 2p21- | ✓ | ✓ | ✓ | ✓ | |

TABLE 16-continued

PE-CVS down-regulated genes linked to decidualization

| Approved symbol | Approved name | HGNC ID | Location | LSE | DEG down-regulated in PE-CVS and up-regulated in: intDEC-EP | intDEC-IUP | confDEC-IUP | Pubmed DEC |
|---|---|---|---|---|---|---|---|---|
| ERO1L | ERO1-like (S. cerevisiae) | HGNC: 13280 | 14q22.1 p16 | ✓ | | | ✓ | ✓ |
| F2R | coagulation factor II (thrombin) receptor | HGNC: 3537 | 5q13 | | ✓ | ✓ | ✓ | ✓ |
| FSTL3 | follistatin-like 3 (secreted glycoprotein) | HGNC: 3973 | 19p13 | | | | ✓ | ✓ |
| GNG4 | guanine nucleotide binding protein (G protein), gamma 4 | HGNC: 4407 | 1q42.3 | ✓ | ✓ | ✓ | ✓ | |
| GNLY | granulysin | HGNC: 4414 | 2p12-q11 | ✓ | ✓ | ✓ | ✓ | ✓ |
| GTPBP2 | GTP binding protein 2 | HGNC: 4670 | 6p21 | ✓ | | | | ✓ |
| GZMB | granzyme B (granzyme 2, cytotoxic T-lymphocyte-associated serine esterase 1) | HGNC:4709 | 14q11.2 | ✓ | ✓ | ✓ | ✓ | ✓ |
| HPS3 | Hermansky-Pudlak syndrome 3 | HGNC: 15597 | 3q24 | ✓ | | | | |
| HTR2B | 5-hydroxytryptamine (serotonin) receptor 2B, G protein-coupled | HGNC: 5294 | 2q36.3-q37.1 | | ✓ | ✓ | ✓ | |
| IGFBP1 | insulin-like growth factor binding protein 1 | HGNC: 5469 | 7p13-p12 | ✓ | ✓ | ✓ | ✓ | ✓ |
| IL15 | interleukin 15 | HGNC: 5977 | 4q31 | ✓ | ✓ | ✓ | ✓ | ✓ |
| IL1B | interleukin 1, beta | HGNC: 5992 | 2q14 | ✓ | | | ✓ | ✓ |
| IL1RL1 | interleukin 1 receptor-like 1 | HGNC: 5998 | 2q12 | | ✓ | ✓ | ✓ | ✓ |
| IL2RB | interleukin 2 receptor, beta | HGNC: 6009 | 22q13 | ✓ | ✓ | ✓ | ✓ | ✓ |
| INPP4B | inositol polyphosphate-4-phosphatase, type II, 105 kDa | HGNC: 6075 | 4q31.1 | ✓ | | | | |
| ITGB6 | integrin, beta 6 | HGNC: 6161 | 2q24.2 | ✓ | | | | |
| LAMA4 | laminin, alpha 4 | HGNC: 6484 | 6q21 | ✓ | ✓ | ✓ | ✓ | |
| LIPH | lipase, member H | HGNC: 18483 | 3q27 | | ✓ | ✓ | ✓ | |
| LSS | lanosterol synthase (2,3-oxidosqualene-lanosterol cyclase) | HGNC: 6708 | 21q22.3 | | | ✓ | ✓ | |
| MAOB | monoamine oxidase B | HGNC: 6834 | Xp11.4-p11.3 | ✓ | ✓ | ✓ | ✓ | |
| MAP3K5 | mitogen-activated protein kinase kinase kinase 5 | HGNC: 6857 | 6q22.33 | ✓ | ✓ | ✓ | | |
| MUC15 | mucin 15, cell surface associated | HGNC: 14956 | 11p14.3 | | ✓ | ✓ | ✓ | ✓ |
| NDP | Norrie disease (pseudoglioma) | HGNC: 7678 | Xp11.4-p11.3 | | ✓ | ✓ | ✓ | ✓ |
| NOG | noggin | HGNC: 7866 | 17q22 | | ✓ | | ✓ | ✓ |
| P4HA3 | prolyl 4-hydroxylase, alpha polypeptide III | HGNC: 30135 | 11q13 | | ✓ | ✓ | ✓ | |
| PAEP | progestagen-associated endometrial protein | HGNC: 8573 | 9q34 | ✓ | | | | ✓ |
| PPP1R3C | protein phosphatase 1, regulatory subunit 3C | HGNC: 9293 | 10q23-q24 | | ✓ | ✓ | ✓ | |
| PRG2 | proteoglycan 2, bone marrow (natural killer cell activator, eosinophil granule major basic protein) | HGNC: 9362 | 11q12 | | | ✓ | ✓ | |
| PRKAB2 | protein kinase, AMP-activated, beta 2 non-catalytic subunit | HGNC: 9379 | 1q21.2 | | | ✓ | ✓ | |
| PRL | prolactin | HGNC: 9445 | 6p22.3 | | ✓ | ✓ | ✓ | ✓ |
| PVR | poliovirus receptor | HGNC: 9705 | 19q13.2 | ✓ | | | ✓ | |
| RBP4 | retinol binding protein 4, plasma | HGNC: 9922 | 10q23.33 | ✓ | ✓ | ✓ | ✓ | |
| RNF14 | ring finger protein 14 | HGNC: 10058 | 5q23.3-q31.1 | | | | ✓ | |
| RORB | RAR-related orphan receptor B | HGNC: 10259 | 9q22 | | | | ✓ | |
| RUFY3 | RUN and FYVE domain containing 3 | HGNC: 30285 | 4q13.3 | ✓ | | | | |
| SCARA5 | scavenger receptor class A, member 5 (putative) | HGNC: 28701 | 8p21.1 | ✓ | ✓ | ✓ | ✓ | ✓ |
| SERPINA3 | serpin peptidase inhibitor, clade A (alpha-1 antiproteinase, antitrypsin), member 3 | HGNC: 16 | 14q32.1 | | | | ✓ | ✓ |
| SLC16A6 | solute carrier family 16, member 6 | HGNC: 10927 | 17q24.2 | | | ✓ | ✓ | |
| SLC25A15 | solute carrier family 25 (mitochondrial carrier; ornithine transporter) member 15 | HGNC: 10985 | 13q14 | | ✓ | ✓ | | |
| SLCO4A1 | solute carrier organic anion transporter family, member 4A1 | HGNC: 10953 | 20q13.1 | ✓ | | | | |
| SNX25 | sorting nexin 25 | HGNC: 21883 | 4q35.1 | | ✓ | ✓ | ✓ | |
| SPOCK1 | sparc/osteonectin, cwcv and kazal-like domains proteoglycan (testican) 1 | HGNC: 11251 | 5q31.2 | ✓ | ✓ | ✓ | ✓ | |
| TES | testis derived transcript (3 LIM domains) | HGNC: 14620 | 7q31.2 | ✓ | | | | |

TABLE 16-continued

PE-CVS down-regulated genes linked to decidualization

| Approved symbol | Approved name | HGNC ID | Location | LSE | DEG down-regulated in PE-CVS and up-regulated in: | | | |
|---|---|---|---|---|---|---|---|---|
| | | | | | intDEC-EP | intDEC-IUP | confDEC-IUP | Pubmed DEC |
| TIAM1 | T-cell lymphoma invasion and metastasis 1 | HGNC: 11805 | 21q22.1 | ✓ | | | | |
| TLN2 | talin 2 | HGNC: 15447 | 15q15-q21 | | ✓ | | ✓ | |
| WT1 | Wilms tumor 1 | HGNC: 12796 | 11p13 | | | | ✓ | ✓ |
| ZNF165 | zinc finger protein 165 | HGNC: 12953 | 6p21 | ✓ | | | | |

TABLE 17

Overlap of DEG up-regulated in dbNK and LSE plus intDEC-EP and intDEC-IUP plus confDEC-IUP (74 genes)

| Approved symbol | Approved name | HGNC ID | Location |
|---|---|---|---|
| ADCY3 | adenylate cyclase 3 | HGNC: 234 | 2p23.3 |
| ADM | adrenomedullin | HGNC: 259 | 11p15.4 |
| APOBEC3G | apolipoprotein B mRNA editing enzyme, catalytic polypeptide-like 3G | HGNC: 17357 | 22q13.1-q13.2 |
| APOC2 | apolipoprotein C-II | HGNC: 609 | 19q13.2 |
| APOD | apolipoprotein D | HGNC: 612 | 3q29 |
| ARHGEF6 | Rac/Cdc42 guanine nucleotide exchange factor (GEF) 6 | HGNC: 685 | Xq26 |
| C19orf10 | chromosome 19 open reading frame 10 | HGNC: 16948 | 19p13.3 |
| C1R | complement component 1, r subcomponent | HGNC: 1246 | 12p13.31 |
| CAMK1 | calcium/calmodulin-dependent protein kinase I | HGNC: 1459 | 3p25.3 |
| CAPG | capping protein (actin filament), gelsolin-like | HGNC: 1474 | 2p11.2 |
| CCR1 | chemokine (C—C motif) receptor 1 | HGNC: 1602 | 3p21 |
| CD38 | CD38 molecule | HGNC: 1667 | 4p15.32 |
| CD3E | CD3e molecule, epsilon (CD3-TCR complex) | HGNC: 1674 | 11q23 |
| CD59 | CD59 molecule, complement regulatory protein | HGNC: 1689 | 11p13 |
| CD96 | CD96 molecule | HGNC: 16892 | 3p13-q13.2 |
| CDHR1 | cadherin-related family member 1 | HGNC: 14550 | 10q23.1 |
| CLU | clusterin | HGNC: 2095 | 8p21-p12 |
| CORO1A | coronin, actin binding protein, 1A | HGNC: 2252 | 16p11.2 |
| CRYAB | crystallin, alpha B | HGNC: 2389 | 11q22.3-q23.1 |
| CTSA | cathepsin A | HGNC: 9251 | 20q13.12 |
| CTSL | cathepsin L | HGNC: 2537 | 9q21.33 |
| DLEU1 | deleted in lymphocytic leukemia 1 (non-protein coding) | HGNC: 13747 | 13q14.3 |
| DOCK10 | dedicator of cytokinesis 10 | HGNC: 23479 | 2q36.3 |
| DPYSL2 | dihydropyrimidinase-like 2 | HGNC: 3014 | 8p22-p21 |
| EPAS1 | endothelial PAS domain protein 1 | HGNC: 3374 | 2p21-p16 |
| FAM49A | family with sequence similarity 49, member A | HGNC: 25373 | 2p24.3 |
| FASLG | Fas ligand (TNF superfamily, member 6) | HGNC: 11936 | 1q23 |
| FCER1G | Fc fragment of IgE, high affinity I, receptor for; gamma polypeptide | HGNC: 3611 | 1q23 |
| FGR | feline Gardner-Rasheed sarcoma viral oncogene homolog | HGNC: 3697 | 1p36.2-p36.1 |
| FKBP1A | FK506 binding protein 1A, 12 kDa | HGNC: 3711 | 20p13 |
| GADD45A | growth arrest and DNA-damage-inducible, alpha | HGNC: 4095 | 1p31.2 |
| GAS1 | growth arrest-specific 1 | HGNC: 4165 | 9q21.3-q22 |
| GLUL | glutamate-ammonia ligase | HGNC: 4341 | 1q31 |
| GNLY | granulysin | HGNC: 4414 | 2p12-q11 |
| GPX3 | glutathione peroxidase 3 (plasma) | HGNC: 4555 | 5q23 |
| GZMA | granzyme A (granzyme 1, cytotoxic T-lymphocyte-associated serine esterase 3) | HGNC: 4708 | 5q11-q12 |
| HOPX | HOP homeobox | HGNC: 24961 | 4q12 |
| IGFBP1 | insulin-like growth factor binding protein 1 | HGNC: 5469 | 7p13-p12 |
| IGFBP2 | insulin-like growth factor binding protein 2, 36 kDa | HGNC: 5471 | 2q33-q34 |
| IL1B | interleukin 1, beta | HGNC: 5992 | 2q14 |
| ITGA1 | integrin, alpha 1 | HGNC: 6134 | 5q11.1 |
| ITGAD | integrin, alpha D | HGNC: 6146 | 16p13.1-p11 |
| ITM2A | integral membrane protein 2A | HGNC: 6173 | Xq13.3-q21.2 |
| KIR3DL1 | killer cell immunoglobulin-like receptor, three domains, long cytoplasmic tail, 1 | HGNC: 6338 | 19q13.4 |
| KIR3DL2 | killer cell immunoglobulin-like receptor, three domains, long cytoplasmic tail, 2 | HGNC: 6339 | 19q13.4 |
| LCP2 | lymphocyte cytosolic protein 2 (SH2 domain containing leukocyte protein of 76 kDa) | HGNC: 6529 | 5q35.1 |
| LILRP2 | leukocyte immunoglobulin-like receptor pseudogene 2 | HGNC: 15497 | 19q13.4 |
| MDFIC | MyoD family inhibitor domain containing | HGNC: 28870 | 7q31.1-q31.2 |

TABLE 17-continued

Overlap of DEG up-regulated in dbNK and LSE plus intDEC-EP and intDEC-IUP plus confDEC-IUP (74 genes)

| Approved symbol | Approved name | HGNC ID | Location |
|---|---|---|---|
| MIR22HG | MIR22 host gene (non-protein coding) | HGNC: 28219 | 17p13.3 |
| MTHFD2 | methylenetetrahydrofolate dehydrogenase (NADP+ dependent) 2, methenyltetrahydrofolate cyclohydrolase | HGNC: 7434 | 2p13.1 |
| MYL9 | myosin, light chain 9, regulatory | HGNC: 15754 | 20q11.23 |
| NCAM1 | neural cell adhesion molecule 1 | HGNC: 7656 | 11q23.2 |
| NUCB2 | nucleobindin 2 | HGNC: 8044 | 11p15.1 |
| NUPR1 | nuclear protein, transcriptional regulator, 1 | HGNC: 29990 | 16p11.2 |
| OSTF1 | osteoclast stimulating factor 1 | HGNC: 8510 | 9q13-q21.2 |
| PECAM1 | platelet/endothelial cell adhesion molecule 1 | HGNC: 8823 | 17q23.3 |
| PLCG2 | phospholipase C, gamma 2 (phosphatidylinositol-specific) | HGNC: 9066 | 16q24.1 |
| PNP | purine nucleoside phosphorylase | HGNC: 7892 | 14q11.2 |
| PSTPIP1 | proline-serine-threonine phosphatase interacting protein 1 | HGNC: 9580 | 15q24-q25.1 |
| PTGIS | prostaglandin I2 (prostacyclin) synthase | HGNC: 9603 | 20q13 |
| PTPN6 | protein tyrosine phosphatase, non-receptor type 6 | HGNC: 9658 | 12p13.31 |
| RRAS2 | related RAS viral (r-ras) oncogene homolog 2 | HGNC: 17271 | 11p15.2 |
| SEPT11 | septin 11 | HGNC: 25589 | 4q21.1 |
| SERPING1 | serpin peptidase inhibitor, clade G (C1 inhibitor), member 1 | HGNC: 1228 | 11q12.1 |
| SKAP2 | src kinase associated phosphoprotein 2 | HGNC: 15687 | 7p15.2 |
| SLA | Src-like-adaptor | HGNC: 10902 | 8q24.22 |
| SPINK2 | serine peptidase inhibitor, Kazal type 2 (acrosin-trypsin inhibitor) | HGNC: 11245 | 4q12 |
| SPTSSA | serine palmitoyltransferase, small subunit A | HGNC: 20361 | 14q13.1 |
| TGM2 | transglutaminase 2 | HGNC: 11778 | 20q12 |
| TIMP3 | TIMP metallopeptidase inhibitor 3 | HGNC: 11822 | 22q12.3 |
| TRAF3IP3 | TRAF3 interacting protein 3 | HGNC: 30766 | 1q32.3-q41 |
| TRD | T cell receptor delta locus | HGNC: 12252 | 14q11.2 |
| TRGC2 | T cell receptor gamma constant 2 | HGNC: 12276 | 7p14 |
| TSPAN5 | tetraspanin 5 | HGNC: 17753 | 4q22.3 |

I claim:

1. A method for treating a placental syndrome in a woman comprising the steps of: (a) identifying a woman who has experienced a placental syndrome during a previous pregnancy; (b) determining the late secretory/luteal (LS) phase of the menstrual cycle of the woman from step (a); and (c) administering a therapeutically effective amount of relaxin to the woman from step (a) only during the LS phase of the menstrual cycle to treat the placental syndrome, wherein the LS phase of the menstrual cycle refers to the phase that commences several days following ovulation in the woman.

2. The method according to claim 1, wherein the relaxin is an RXFP-1 agonist or mimetic.

3. The method according to claim 1, wherein determination of the LS phase of the menstrual cycle is performed using a kit that is able to detect LH surge.

4. The method according to claim 1, wherein the therapeutically effective amount of relaxin is 0.1 to about 100 µg/kg of subject body weight per day.

5. The method according to claim 4, wherein the administration of the relaxin results in serum concentrations of relaxin of about 0.1-10.0 ng/ml during the LS phase of the menstrual cycle.

6. The method according to claim 4, wherein administration of the relaxin results in serum concentrations of relaxin of about 0.1-3.0 ng/ml during the LS phase of the menstrual cycle.

7. The method according to claim 1, further comprising the step of (d) determining whether the woman is pregnant and (e) if the woman is determined to be pregnant following step (d), administering a therapeutically effective amount of relaxin to the woman through the $1^{st}$ trimester of pregnancy.

8. The method according to claim 7, wherein the relaxin is an RXFP-1 agonist or mimetic.

9. The method according to claim 1, wherein the placental syndrome is preeclampsia.

10. A method for treating a placental syndrome in a woman comprising the steps of: (a) determining that a woman has a propensity for developing a placental syndrome; (b) determining the late secretory/luteal (LS) phase of the menstrual cycle of the woman from step (a); and (c) administering a therapeutically effective amount of a relaxin to the woman of step (a) only during the LS phase of the menstrual cycle,
wherein the LS phase of the menstrual cycle refers to the phase that commences several days following ovulation in the woman.

11. The method according to claim 10, wherein the relaxin is an RXFP-1 agonist or mimetic.

12. The method according to claim 10, wherein determination of the LS phase of the menstrual cycle is performed using a kit that is able to detect LH surge.

13. The method according to claim 10, wherein the therapeutically effective amount of relaxin is 0.1 to about 100 µg/kg of subject body weight per day.

14. The method according to claim 13, wherein administration of the relaxin results in serum concentrations of relaxin of about 0.1-10.0 ng/ml during the LS phase of the menstrual cycle.

15. The method according to claim 13, wherein administration of the relaxin results in serum concentrations of relaxin of about 0.1-3.0 ng/ml during the LS phase of the menstrual cycle.

16. The method according to claim 10, further comprising the step of (d) determining whether the woman is pregnant and (e) if the woman is determined to be pregnant following step (d), administering a therapeutically effective amount of relaxin (or RXFP-1 agonist or mimetic) to the woman through the $1^{st}$ trimester of pregnancy.

17. The method according to claim 10, wherein the placental syndrome is preeclampsia.

18. The method according to claim 17, wherein step (a) comprises:
obtaining a biological sample from the woman during the LS phase;
performing analysis of the biological sample to determine whether the following one or more genes are downregulated: ALDH1L2; RORB; EPAS1; DLGAP1; SPOCK1; MAOB; GZMB; IL2RB; GNLY; NOG; TRA@; MUC15; KLRC2; IL15; CHRDL1; PRL; SCARA5; CHST6; NTN1; CPM; IL1B; ITGB6; MMP12; BDKRB2; SLC16A6; FN1; PP14; FSTL3; WT1; IGFBP1; CFH/CFHR1; C3; C4BPA; Flt-4; HTR2B; and ERAP2; and
performing analysis of the biological sample to determine whether the following one or more genes are upregulated: ACOT8; BICD1; ADCYAP1R1; DPYSL4; COL5A1; FOSB; CR1; and S100A8.

19. The method according to claim 18, wherein step (a) further comprises the use of an immunoassay for (i) binding one or more polypeptide species in the biological sample to an antibody and quantitatively determining the amount of said one or more polypeptide species in said biological sample to determine downregulation or upregulation of the one or more genes, and (ii) comparing the amount of the polypeptide species from step (i) to a standard control representing the amount of the polypeptide species in the corresponding sample from an average non-preeclamptic woman, wherein an increase or a decrease in the amount of the polypeptide species from the standard control indicates upregulation or downregulation of the one or more genes.

20. The method according to claim 19, wherein said immunoassay is selected from the group consisting of: a radioimmunoassay, ELISA (enzyme-linked immunosorbant assay), sandwich immunoassay, immunoradiometric assay and Western blot.

21. The method according to claim 18, wherein the biological sample can be blood, washing from the reproductive tract, urine, saliva, or endometrial biopsy.

22. The method according to claim 17, wherein step (a) comprises:
obtaining a biological sample from the woman during the LS phase;
quantitatively determining the amount of endogenous relaxin in the biological sample; and
comparing the amount of the quantified amount of endogenous relaxin to a standard control representing the amount of the endogenous relaxin in the corresponding sample from a woman without symptoms of placental syndromes; wherein an increase and decrease in the amount of the endogenous relaxin in the biological sample as compared to the standard control indicates an increased risk of developing preeclampsia.

23. The method according to claim 22, wherein the step of quantitatively determining the amount of endogenous relaxin in the biological sample comprises determining the amount of one or more nucleic acid species in the biological sample that hybridizes with any one or more probe set for RLN-1, RLN-2, RLN-3 and RXFP1.

* * * * *

UNITED STATES PATENT AND TRADEMARK OFFICE
CERTIFICATE OF CORRECTION

PATENT NO. : 9,907,833 B2  
APPLICATION NO. : 14/340858  
DATED : March 6, 2018  
INVENTOR(S) : Kirk P. Conrad Page 1 of 1

It is certified that error appears in the above-identified patent and that said Letters Patent is hereby corrected as shown below:

In the Specification

Column 29,  
Line 35, "FIG. C). As" should read -- Figure 12C). As --.

Column 30,  
Line 15, "(PrE; DEG)." should read -- (PrE; 20 DEG). --.

Signed and Sealed this  
Third Day of July, 2018

Andrei Iancu  
*Director of the United States Patent and Trademark Office*